(12) United States Patent
Tang et al.

(10) Patent No.: US 11,059,815 B2
(45) Date of Patent: Jul. 13, 2021

(54) SYNTHESIS OF SMALL MOLECULE HISTONE DEACETYLASE 6 DEGRADERS, COMPOUNDS FORMED THEREBY, AND PHARMACEUTICAL COMPOSITIONS CONTAINING THEM

(71) Applicant: Wisconsin Alumni Research Foundation, Madison, WI (US)

(72) Inventors: Weiping Tang, Middleton, WI (US); Ka Yang, Madison, WI (US); Hao Wu, Madison, WI (US); Zhongrui Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/800,514

(22) Filed: Feb. 25, 2020

(65) Prior Publication Data
US 2020/0190079 A1    Jun. 18, 2020

Related U.S. Application Data

(63) Continuation-in-part of application No. 16/517,943, filed on Jul. 22, 2019.

(60) Provisional application No. 62/844,784, filed on May 8, 2019, provisional application No. 62/831,817, filed on Apr. 10, 2019, provisional application No. 62/701,892, filed on Jul. 23, 2018.

(51) Int. Cl.
C07D 417/14 (2006.01)
C07D 401/14 (2006.01)

(52) U.S. Cl.
CPC ......... C07D 417/14 (2013.01); C07D 401/14 (2013.01)

(58) Field of Classification Search
CPC .................................................. C07D 417/14
See application file for complete search history.

(56) References Cited

PUBLICATIONS

An et al. "Developing Potent PROTACs Tools for Selective Degradation of HDAC6 Protein" Protein Cell 2019, 10(8), 606-609.
Bassi et al. "Modulating PCAF/GCN5 Immune Cell Function through a PROTAC Approach" ACS Chem. Biol. 2018, 13 (10), 2862-2867.
Batchu et al. "The Therapeutic Hope for Hdac6 Inhibitors in Malignancy and Chronic Disease" Clin. Sci. 2016, 130, 987.
Bergman et al. "Selective Histone Deacetylase 6 Inhibitors Bearing Substituted Urea Linkers Inhibit Melanoma Cell Growth" J. Med. Chem. 2012, 55 (22), 9891-9899.
Bondeson et al. "Catalytic in Vivo Protein Knockdown by Small-Molecule Protacs" Nat. Chem. Biol. 2015, 11, 611-617.
Bondeson et al. "Lessons in PROTAC Design from Selective Degradation with a Promiscuous Warhead" Cell Chem. Biol. 2018, 25 (1), 78-87.
Bradbury et al. "Histone Deacetylases in Acute Myeloid Leukaemia Show a Distinctive Pattern of Expression That Changes Selectively in Response to Deacetylase Inhibitors" Leukemia 2005, 19, 1751-1759.
Bradner et al. "Chemical Phylogenetics of Histone Deacetylases" Nat. Chem. Biol. 2010, 6, 238.
Buckley et al. Small-Molecule Control of Intracellular Protein Levels through Modulation of the Ubiquitin Proteasome System. Angew. Chemie—Int. Ed. 2014, 53 (9), 2312-2330.
Burslem et al. "The Advantages of Targeted Protein Degradation Over Inhibition: An RTK Case Study" Cell Chem. Biol. 2018, 25 (1), 67-77.
Chamberlain et al. "Structure of the Human Cereblon-DDB1-Lenalidomide Complex Reveals Basis for Responsiveness to Thalidomide Analogs" Nat. Struct. Mol. Biol. 2014, 21 (9), 803-809.
Cosenza et al. "Ricolinostat (Acy-1215), a Selective HDAC6 Inhibitor, Alone and in Combination with Bendamustine is Effective in Preclinical Studies in Lymphoma Cell Lines" Blood 2016, 128.
Cosenza et al, Ricolinostat, a selective HDAC6 inhibitor, shows anti-lymphoma cell activity alone and in combination with bendamustine, Apoptosis, 2017 22:827-840.
De Vreese et al. "Synthesis and SAR Assessment of Novel Tubathian Analogs in the Pursuit of Potent and Selective Hdac6 Inhibitors" Org. Biomol. Chem. 2016, 14, 2537-2549.
De Vreese et al. "Synthesis of Potent and Selective HDAC6 Inhibitors Bearing a Cyclohexane- or Cycloheptane-Annulated 1,5-Benzothiazepine Scaffold" Chem. Eur. J. 2017, 23, 128-136.
Demizu et al. "Design and Synthesis of Estrogen Receptor Degradation Inducer Based on a Protein Knockdown Strategy" Bioorg. Med. Chem. Lett. 2012, 22 (4), 1793-1796.
Douglass et al.. "A Comprehensive Mathematical Model for Three-Body Binding Equilibria" J. Am. Chem. Soc. 2013, 135(16), 6092-6099.
Erb et al. "Transcription Control by the ENL Yeats Domain in Acute Leukaemia" Nature 2017, 543(7644), 270-274.
Falkenberg et al. "Histone Deacetylases and Their Inhibitors in Cancer, Neurological Diseases and Immune Disorders" Nat. Rev. Drug Discovery 2014, 13, 673-691.
Fass et al. "Crebinostat: A Novel Cognitive Enhancer That Inhibits Histone Deacetylase Activity and Modulates Chromatin-Mediated Neuroplasticity" Neuropharmacology 2013, 64, 81-96.
Fischer et al. "Structure of the DDB1-CRBN E3 Ubiquitin Ligase in Complex with Thalidomide" Nature 2014, 512 (7512), 49-53.
Gadd et al. "Structural Basis of PROTAC Cooperative Recognition for Selective Protein Degradation" Nat. Chem. Biol. 2017, 13 (5), 514-521.
Goracci et al. "A Rational Approach for the Identification of Non-Hydroxamate HDAC6-Selective Inhibitors" Sci. Rep. 2016, 6-12.
Hideshima et al. "Rational Combination Treatment with Histone Deacetylase Inhibitors and Immunomodulatory Drugs in Multiple Myeloma" Blood Cancer J. 2015, 5 (5), e312-e312.

(Continued)

Primary Examiner — Emily A Bernhardt
(74) Attorney, Agent, or Firm — Joseph T. Leone, Esq.; DeWitt LLP

(57) ABSTRACT

Histone deacetylase ("HDAC")-selective inhibitors covalently bonded to a linker covalently bonded to an E3 ubiquitin ligase ligand, and salts thereof; pharmaceutical compositions containing them; methods of using the composition to inhibit neoplastic cell growth in mammals, including humans.

14 Claims, 23 Drawing Sheets

(56) References Cited

PUBLICATIONS

Hideshima et al. "Discovery of Selective Small-Molecule HDAC6 Inhibitor for Overcoming Proteasome Inhibitor Resistance in Multiple Myeloma" *Proc. Natl. Acad. Sci. USA* 2016, 113, 13162-13167.

Ito et al. "Identification of a Primary Target of Thalidomide Teratogenicity" *Science* 2010, 327, 1345-1350.

Jang et al. "Novel Analogs Targeting Histone Deacetylase Suppress Aggressive Thyroid Cancer Cell Growth and Induce Re-Differentiation" *Cancer Gene Ther.* 2015, 22 (8), 410-416.

Jaskula-Sztul et al. "Tumor-Suppressor Role of Notch3 in Medullary Thyroid Carcinoma Revealed by Genetic and Pharmacological Induction" *Mol. Cancer Ther.* 2015, 14 (2), 499-512.

Johnstone, R. W. "Histone-Deacetylase Inhibitors: Novel Drugs for the Treatment of Cancer" *Nat. Rev. Drug Discovery* 2002, 1, 287-299.

Kalin et al. "Development and Therapeutic Implications of Selective Histone Deacetylase 6 Inhibitors" *J. Med. Chem.* 2013, 56, 6297-6313.

Kronke et al. "Lenalidomide Causes Selective Degradation of IKZF1 and IKZF3 in Multiple Myeloma Cells" *Science* 2014, 343(6168), 301-305.

Lai et al. "Modular PROTAC Design for the Degradation of Oncogenic BCR-ABL" *Angew. Chemie—Int. Ed.* 2016, 55 (2), 807-810.

Lai et al. "Induced Protein Degradation: An Emerging Drug Discovery Paradigm" *Nat. Rev. Drug Discovery* 2017, 16, 101-114.

Li et al. "Discovery of MD-224 as a First-in-Class, Highly Potent, and Efficacious Proteolysis Targeting Chimera Murine Double Minute 2 Degrader Capable of Achieving Complete and Durable Tumor Regression" *J. Med. Chem.* 2019, 62 (2), 448-466.

Lin et al. "Design and Synthesis of Orally Bioavailable Aminopyrrolidinone Histone Deacetylase 6 Inhibitors" *J. Med. Chem.* 2015, 58, 2809-2820.

Livak et al. "Analysis of Relative Gene Expression Data Using Real-Time Quantitative PCR and the $2^{-\Delta\Delta C_T}$ Method" *METHODS* 2001, 25, 402-408.

Lu et al. "The Myeloma Drug Lenalidomide Promotes the Cereblon-Dependent Destruction of Ikaros Proteins" *Science* 2014, 343(6168), 305-309.

Lu et al. "Hijacking the E3 Ubiquitin Ligase Cereblon to Efficiently Target BRD4" *Chem. Biol.* 2015, 22(6), 755-763.

Matyskiela et al. "A Novel Cereblon Modulator Recruits GSPT1 to the CRL4$^{(CRBN)}$ Ubiquitin Ligase" *Nature* 2016, 535, 252.

Miyake et al. "Structural Insights into HDAC6 Tubulin Deacetylation and its Selective Inhibition" *Nat. Chem. Biol.* 2016, 12 (9), 748-754.

Nabet et al. "The dTAG System for Immediate and Target-Specific Protein Degradation" *Nat. Chem. Biol.* 2018, 14 (5), 431-441.

Niesvizky et al. "Selective HDAC6 Inhibitor ACY-241, an Oral Tablet, Combined with Pomalidomide and Dexamethasone: Safety and Efficacy of Escalation and Expansion Cohorts in Patients with Relapsed or Relapsed-and-Refractory Multiple Myeloma (ACE-MM-200 Study)" *Blood* 2016, 128 (22), 3307.

Olson et al. "Pharmacological Perturbation of CDK9 Using Selective CDK9 Inhibition or Degradation" *Nat. Chem. Biol.* 2018, 14, 163-170.

Ottis et al. "Proteolysis-Targeting Chimeras: Induced Protein Degradation as a Therapeutic Strategy" *ACS Chem. Biol.* 2017, 12 (4), 892-898.

Papadas A., Asimakopoulos F. (2017) "Mechanisms of Resistance in Multiple Myeloma." In: Mandalà M., Romano E. (eds) Mechanisms of Drug Resistance in Cancer Therapy. Handbook of Experimental Pharmacology, vol. 249. © 2017 Springer, Cham, ISBN 978-3-030-10507-5.

Qin et al. "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression" *J. Med. Chem.* 2018, 61 (15), 6685-6704.

Raina et al. "Protac-Induced Bet Protein Degradation as a Therapy for Castration-Resistant Prostate Cancer" *Proc. Natl. Acad. Sci. USA* 2016, 113, 7124.

Ray et al. "Combination of a Novel HDAC6 Inhibitor ACY-241 and Anti-PD-L1 Antibody Enhances Anti-Tumor Immunity and Cytotoxicity in Multiple Myeloma" *Leukemia* 2018, 32 (3), 843-846.

Remillard et al. "Degradation of the BAF Complex Factor BRD9 by Heterobifunctional Ligands" *Angew. Chem. Int. Ed.* 2017, 56, 5738-5743.

Sakamoto et al. "Protacs: Chimeric Molecules That Target Proteins to the Skp1-Cullin-F Box Complex for Ubiquitination and Degradation" *Proc. Natl. Acad. Sci. USA* 2001, 98, 8554-8559.

Santo et al. "Preclinical Activity, Pharmacodynamic, and Pharmacokinetic Properties of a Selective HDAC6 Inhibitor, ACY-1215, in Combination with Bortezomib in Multiple Myeloma" *Blood* 2012, 119 (11), 2579-2589.

Schiedel et al. "Chemically Induced Degradation of Sirtuin 2 (Sirt2) by a Proteolysis Targeting Chimera (PROTAC) Based on Sirtuin Rearranging Ligands (SirReals)" *J. Med. Chem.* 2018, 61 (2), 482-491.

Senger et al. "Synthesis and Biological Investigation of Oxazole Hydroxamates as Highly Selective Histone Deacetylase 6 (Hdac6) Inhibitors" *J. Med. Chem.* 2016, 59, 1545-1555.

Shen, et al. "Bicyclic-Capped Histone Deacetylase 6 Inhibitors with Improved Activity in a Model of Axonal Charcot-Marie-Tooth Disease" *ACS Chem. Neurosci.* 2016, 7(2), 240-258.

Tahtouh et al. "Selectivity Cocrystal Structures, and Neuroprotective Properties of Leucettines, a Family of Protein Kinase Inhibitors Derived from the Marine Sponge Alkaloid Leucettamine" B, *J. Med. Chem.* 2012, 55, 9312-9330.

Tang et al. "Discovery of Histone Deacetylase 8 Selective Inhibitors" *Bioorg. Med. Chem. Lett.* 2011, 21 (9), 2601-2605.

Wang et al. "Boiling Water-Catalyzed Neutral and Selective N-Boc Deprotection" *Chem. Commun.* 2009, 0 (34), 5144-5146.

Winter et al. "Phthalimide Conjugation as a Strategy for in Vivo Target Protein Degradation" *Science* 2015, 348 (6241), 1376-1381.

Yang et al. "Discovery of Selective Histone Deacetylase 6 Inhibitors Using the Quinazoline as the Cap for the Treatment of Cancer" *J. Med. Chem.* 2016, 59, 1455-1470.

Yang et al. "Development of the First Small Molecule Histone Deacetylase 6 (HDAC6) Degraders" *Bioorg. Med. Chem. Lett.* 2018, 28 (14), 2493-2497.

Yee et al. "Ricolinostat (Acy-1215), the First Selective HDAC6 Inhibitor, in Combination with Lenalidomide and Dexamethasone in Patients with Relapsed and Relapsed -and Refractory Multiple Myeloma: Phase 1b Results (Ace-Mm-101 Study)" *Blood* 2015, 126, 3055.

Zengerle et al. "Selective Small Molecule Induced Degradation of the Bet Bromodomain Protein BRD4" *ACS Chem. Biol.* 2015, 10, 1770-177.

Zhang et al. "Degradation of Target Protein in Living Cells by Small-Molecule Proteolysis Inducer" *Bioorg. Med. Chem. Lett.* 2004, 14, 645-648.

Zhang et al. "Mice Lacking Histone Deacetylase 6 Have Hyperacetylated Tubulin but are Viable and Develop Normally" *Mol. Cell Biol.* 2008, 28, 1688-1701.

Zhou et al. "Discovery of a Small-Molecule Degrader of Bromodomain and Extra-Terminal (BET) Proteins with Picomolar Cellular Potencies and Capable of Achieving Tumor Regression" *J. Med. Chem.* 2018, 61 (2), 462-481.

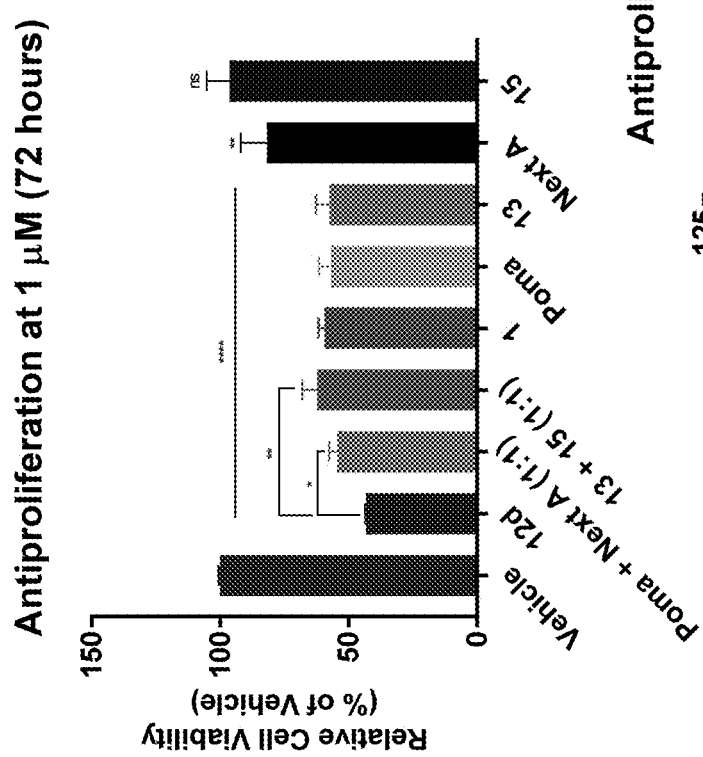
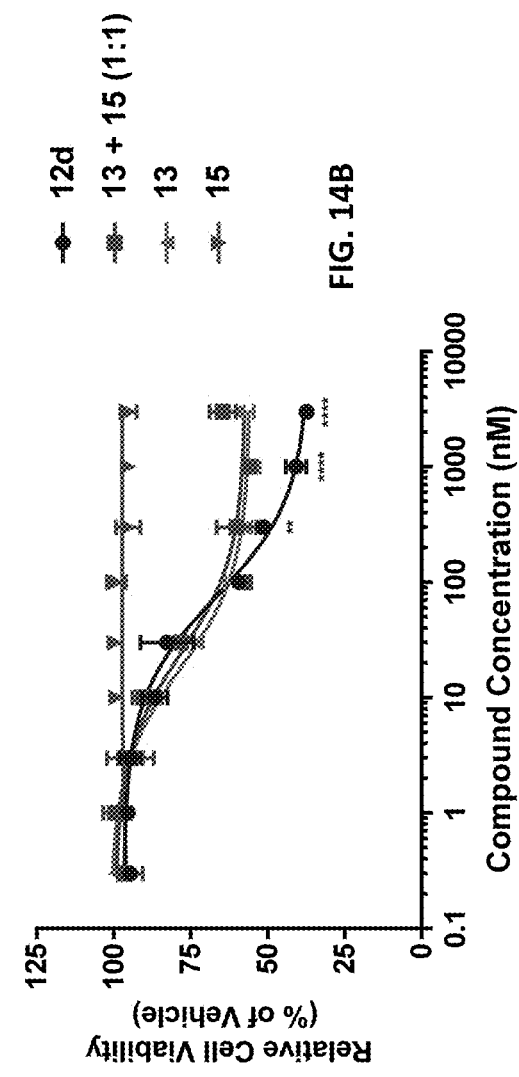
FIG. 14A
FIG. 14B

SYNTHESIS OF SMALL MOLECULE HISTONE DEACETYLASE 6 DEGRADERS, COMPOUNDS FORMED THEREBY, AND PHARMACEUTICAL COMPOSITIONS CONTAINING THEM

CROSS-REFERENCE TO RELATED APPLICATIONS

This is a continuation-in-part of co-pending application Ser. No. 16/517,943, filed Jul. 22, 2019, which claims priority to provisional application Ser. No. 62/844,784, filed May 8, 2019, provisional application Ser. No. 62/831,817, filed Apr. 10, 2019, and provisional application Ser. No. 62/701,892, filed Jul. 23, 2018, all of which are incorporated herein by reference.

FEDERAL FUNDING STATEMENT

This invention was made with government support under GM120357 and CA014520 awarded by the National Institutes of Health. The government has certain rights in the invention.

BACKGROUND

Targeted protein degradation is emerging as an exciting therapeutic option to confront diseases involving aberrantly expressed or mutated disease-causing proteins. At the heart of the approach is to engage the body's own natural protein disposal system to destroy the pathogenic protein. (Lai, A. C.; Crews, C. M. "Induced Protein Degradation: An Emerging Drug Discovery Paradigm" Nat. Rev. Drug Discovery 2017, 16, 101.) Typically, targeted protein degradation uses heterobifunctional small molecules bonded together via an appropriate linker. (Sakamoto, K. M.; Kim, K. B.; Kumagai, A.; Mercurio, F.; Crews, C. M.; Deshaies, R. J. "Protacs: Chimeric Molecules That Target Proteins to the Skp1-Cullin-F Box Complex for Ubiquitination and Degradation" Proc. Natl. Acad. Sci. USA 2001, 98, 8554.) Early studies used peptides as an E3 ligase ligand. The resulting degraders, however, generally showed low cellular potency, partially due to their low permeability and stability. (See, for example, Zhang, D.; Baek, S. H.; Ho, A.; Kim, K. "Degradation of Target Protein in Living Cells by Small-Molecule Proteolysis Inducer" Bioorg. Med. Chem. Lett. 2004, 14, 645.) Potent, small-molecule E3 ligase ligands have been used for targeted protein degradation and this has led to the development of a number of small molecule degraders having high potency in cells and impressive efficacy in animal models. See Winter, G. E.; Buckley, D. L.; Paulk, J.; Roberts, J. M.; Souza, A.; Dhe-Paganon, S.; Bradner, J. E. "Phthalimide Conjugation as a Strategy for in Vivo Target Protein Degradation" Science 2015, 348, 1376. Bondeson, D. P.; Mares, A.; Smith, I. E. D.; Ko, E.; Campos, S.; Miah, A. H.; Mulholland, K. E.; Routly, N.; Buckley, D. L.; Gustafson, J. L.; Zinn, N.; Grandi, P.; Shimamura, S.; Bergamini, G.; Faelth-Savitski, M.; Bantscheff, M.; Cox, C.; Gordon, D. A.; Willard, R. R.; Flanagan, J. J.; Casillas, L. N.; Votta, B. J.; den Besten, W.; Famm, K.; Kruidenier, L.; Carter, P. S.; Harling, J. D.; Churcher, I.; Crews, C. M. "Catalytic in Vivo Protein Knockdown by Small-Molecule Protacs" Nat. Chem. Biol. 2015, 11, 611. Lu, J.; Qian, Y. M.; Altieri, M.; Dong, H. Q.; Wang, J.; Raina, K.; Hines, J.; Winkler, J. D.; Crew, A. P.; Coleman, K.; Crews, C. M. "Hijacking the E3 Ubiquitin Ligase Cereblon to Efficiently Target Brd4" Chem. Biol. 2015, 22, 755. Zengerle, M.; Chan, K. H.; Ciulli, A. "Selective Small Molecule Induced Degradation of the Bet Bromodomain Protein Brd4" ACS Chem. Biol. 2015, 10, 1770. Matyskiela, M. E.; Lu, G.; Ito, T.; Pagarigan, B.; Lu, C. C.; Miller, K.; Fang, W.; Wang, N. Y.; Nguyen, D.; Houston, J.; Carmel, G.; Tran, T.; Riley, M.; Nosaka, L.; Lander, G. C.; Gaidarova, S.; Xu, S. C.; Ruchelman, A. L.; Handa, H.; Carmichael, J.; Daniel, T. O.; Cathers, B. E.; Lopez-Girona, A.; Chamberlain, P. P. "A Novel Cereblon Modulator Recruits Gsptl to the Crl4(Crbn) Ubiquitin Ligase" Nature 2016, 535, 252. Lai, A. C.; Toure, M.; Hellerschmied, D.; Salami, J.; Jaime-Figueroa, S.; Ko, E.; Hines, J.; Crews, C. M. "Modular Protac Design for the Degradation of Oncogenic Bcr-Abl" Angew. Chem. Int. Ed. 2016, 55, 807. Raina, K.; Lu, J.; Qian, Y. M.; Altieri, M.; Gordon, D.; Rossi, A. M. K.; Wang, J.; Chen, X.; Dong, H. Q.; Siu, K.; Winkler, J. D.; Crew, A. P.; Crews, C. M.; Coleman, K. G. "Protac-Induced Bet Protein Degradation as a Therapy for Castration-Resistant Prostate Cancer" Proc. Natl. Acad. Sci. USA 2016, 113, 7124. Erb, M. A.; Scott, T. G.; Li, B. E.; Xie, H. F.; Paulk, J.; Seo, H. S.; Souza, A.; Roberts, J. M.; Dastjerdi, S.; Buckley, D. L.; Sanjana, N. E.; Shalem, O.; Nabet, B.; Zeid, R.; Offei-Addo, N. K.; Dhe-Paganon, S.; Zhang, F.; Orkin, S. H.; Winter, G. E.; Bradner, J. E. "Transcription Control by the Enl Yeats Domain in Acute Leukaemia" Nature 2017, 543, 270. Remillard, D.; Buckley, D. L.; Paulk, J.; Brien, G. L.; Sonnett, M.; Seo, H. S.; Dastjerdi, S.; Wuhr, M.; Dhe-Paganon, S.; Armstrong, S. A.; Bradner, J. E. "Degradation of the Baf Complex Factor Brd9 by Heterobifunctional Ligands" Angew. Chem. Int. Ed. 2017, 56, 5738. Olson, C. M.; Jiang, B. S.; Erb, M. A.; Liang, Y. K.; Doctor, Z. M.; Zhang, Z. N.; Zhang, T. H.; Kwiatkowski, N.; Boukhali, M.; Green, J. L.; Haas, W.; Nomanbhoy, T.; Fischer, E. S.; Young, R. A.; Bradner, J. E.; Winter, G. E.; Gray, N. S. "Pharmacological Perturbation of Cdk9 Using Selective Cdk9 Inhibition or Degradation" Nat. Chem. Biol. 2018, 14, 163.

Most members of histone deacetylases (HDACs) repress gene transcription by modulating chromatin structures in the nucleus. Altered expression of HDAC enzymes is detected in the clinical presentation of many cancers. A number of HDAC inhibitors have been approved by FDA for treating cancers in humans. (Falkenberg, K. J.; Johnstone, R. W. "Histone Deacetylases and Their Inhibitors in Cancer, Neurological Diseases and Immune Disorders" Nat. Rev. Drug Discovery 2014, 13, 673. Johnstone, R. W. "Histone-Deacetylase Inhibitors: Novel Drugs for the Treatment of Cancer" Nat. Rev. Drug Discovery 2002, 1, 287. However, all of the approved HDAC inhibitors target HDACs non-selectively and thus exhibit significant toxicity. (Bradner, J. E.; West, N.; Grachan, M. L.; Greenberg, E. F.; Haggarty, S. J.; Warnow, T.; Mazitschek, R. "Chemical Phylogenetics of Histone Deacetylases" Nat. Chem. Biol. 2010, 6, 238.) Development of selective HDAC inhibitors is a long-felt and unmet need that could increase the effectiveness of the compounds to inhibit neoplastic cell growth, while simultaneously reducing their toxicity.

Additionally, most HDAC's function inside the nucleus of eukaryotes. HDAC6, however, is primarily located in the cytoplasm. It is aberrantly active and overexpressed in many diseases such as cancers, neurodegenerative diseases, and autoimmune disorders. (Kalin, J. H.; Bergman, J. A. "Development and Therapeutic Implications of Selective Histone Deacetylase 6 Inhibitors" J. Med. Chem. 2013, 56, 6297.) For example, HDAC6 is overexpressed in oral squamous cell carcinoma, acute myeloid leukemia, ovarian cancer, and hepatocellular carcinomas. HDAC6 concentration is clinically significant because it indicates advanced staging of the disease and correlates with higher rates of metastatic events and lower survival rates. ((23) Bradbury, C.; Khanim, F.; Hayden, R.; Bunce, C. M.; White, D. A.; Drayson, M. T.; Craddock, C.; Turner, B. M. "Histone Deacetylases in Acute Myeloid Leukaemia Show a Distinctive Pattern of Expression That Changes Selectively in Response to Deacetylase Inhibitors" *Leukemia* 2005, 19, 1751.) The HDAC6 selective inhibitor Ricolinostat (ACY-1215) is currently being tested in multiple human clinical trials for the treatment of cancers including multiple myeloma, metastatic breast cancer, and lymphoma. (Cosenza, M.; Civallero, M.; Quayle, S. N.; Sacchi, S.; Pozzi, S. "Ricolinostat (Acy-1215), a Selective Hdac6 Inhibitor, Alone and in Combination with Bendamustine Is Effective in Preclinical Studies in Lymphoma Cell Lines" *Blood* 2016, 128.)

The HDAC6 selective inhibitors are often combined with other reagents including thalidomide analogues. See, for example, Yee, A. J.; Bensinger, W.; Voorhees, P. M.; Berdeja, J. G.; Richardson, P. G.; Supko, J.; Tamang, D.; Jones, S. S.; Wheeler, C.; Markelewicz, R. J., Jr.; Raje, N. S. "Ricolinostat (Acy-1215), the First Selective Hdac6 Inhibitor, in Combonation with Lenalidomide and Dexamethasone in Patients with Relapsed and Relapsed—and Refractory Multiple Myeloma: Phase Lb Results (Ace-Mm-101 Study)" *Blood* 2015, 126.

SUMMARY

Disclosed herein are compounds comprising a histone deacetylase 6 ("HDAC6")-selective inhibitor covalently bonded to a linker, covalently bonded to an E3 ubiquitin ligase ligand:

HDAC6-Selective Inhibitor-Linker-E3 Ubiquitin Ligase Ligand

The HDAC6-selective inhibitor portion of the compound is selected from the group consisting of:

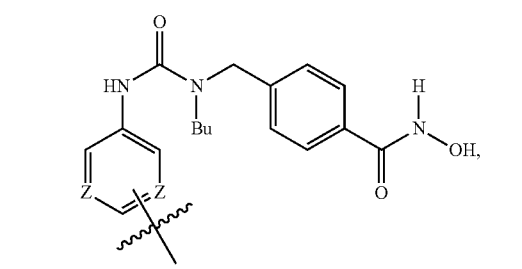

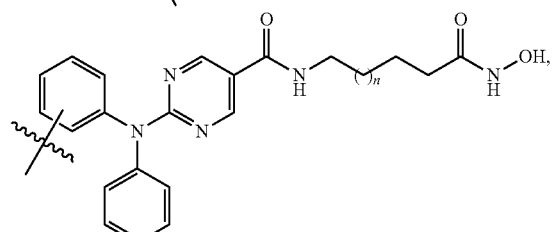

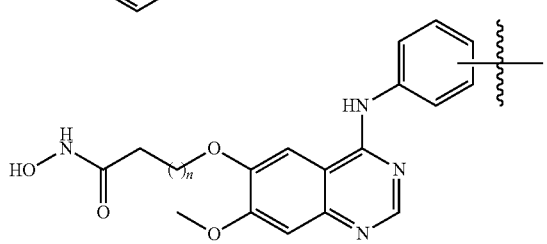

-continued

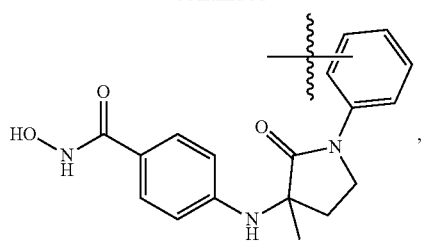

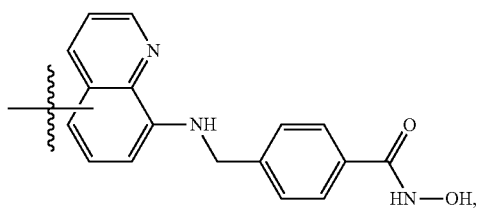

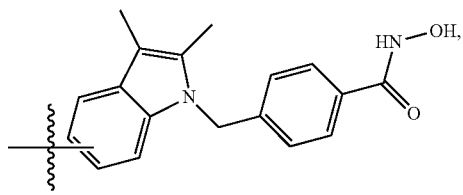

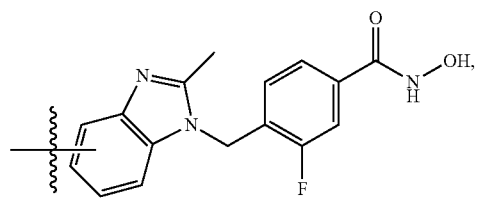

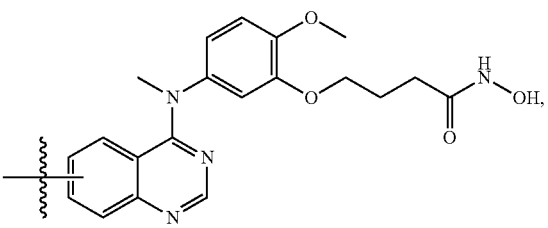

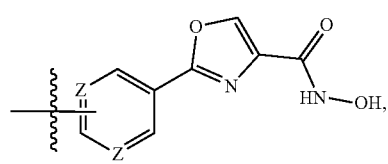

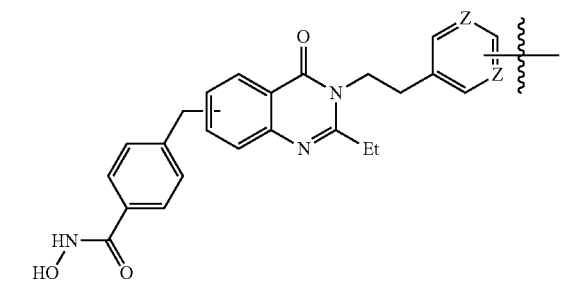

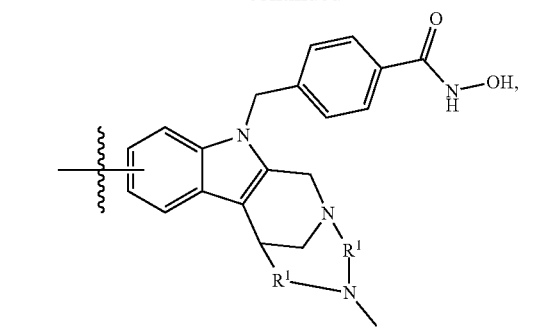
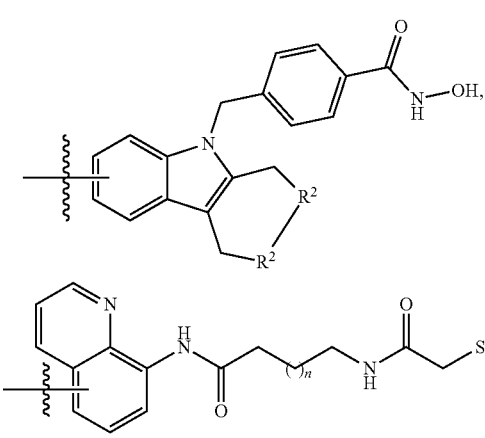
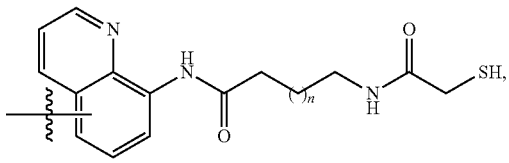
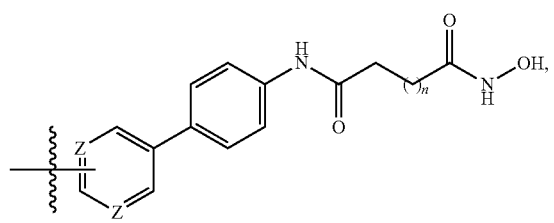
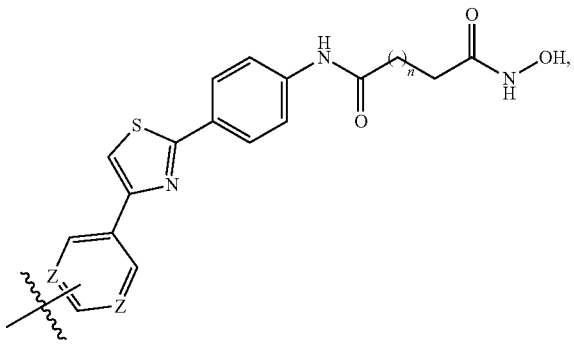
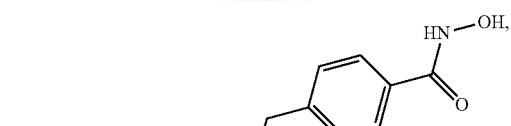
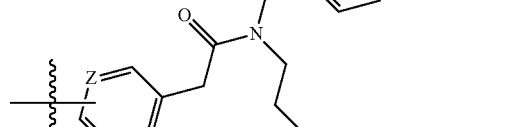
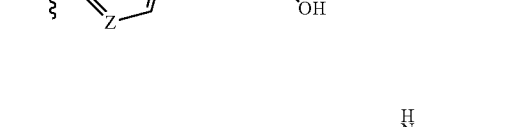
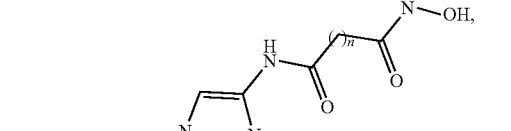
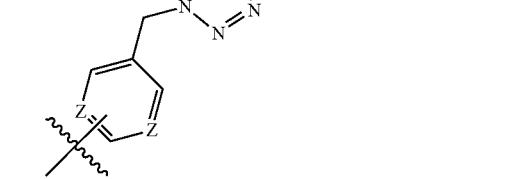
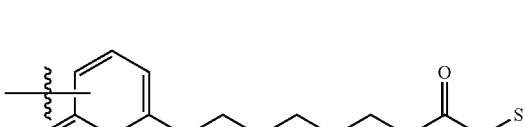

-continued

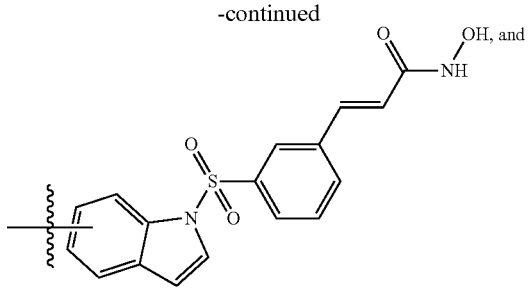

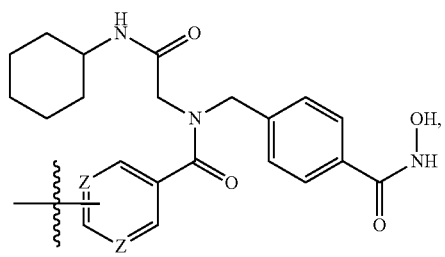

wherein each R$^1$ is independently selected from —O— or —(NH)—, each R$^2$ is independently selected from —(CH$_2$)— or —(NH)—, each Z is independently selected from —N— or —(CH)—, and each "n" is an integer of from 1 to 12.

The linker portion of the compound is a C$_1$-C$_{12}$ linear or branched alkylene, alkenylene, or alkynylene, —O—(CH$_2$)$_m$—, or —NH—(CH$_2$)$_m$, wherein "m" is an integer of from 1 to 12.

The E3 ubiquitin ligase ligand portion of the compound is selected from:

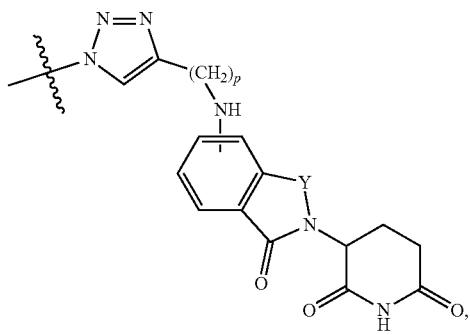

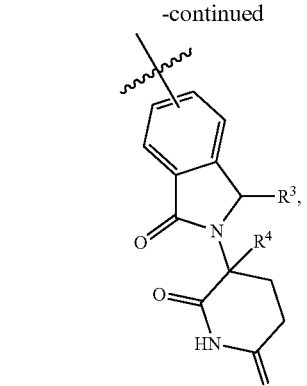

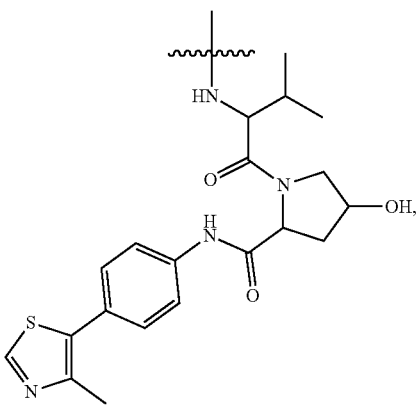

the E3 ubiquitin ligase ligand is selected from:

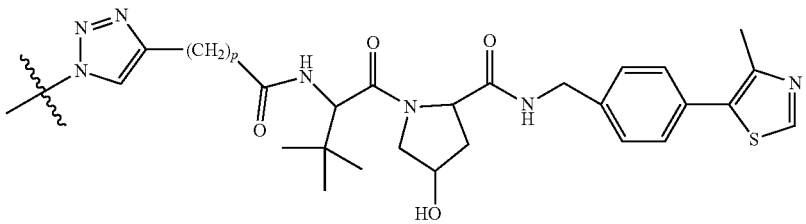

wherein R$^3$ is hydrogen, C$_1$-C$_6$-alkyl, or =O, R$^4$ is hydrogen or halogen, Y is —(C=O)— or —(CH$_2$)—, and "p" is an integer of from 1 to 12; and
salts thereof.

In preferred versions, the HDAC6-selective inhibitor portion of the compound is:

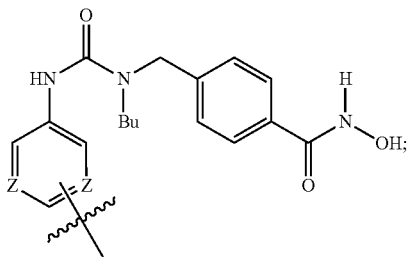

and the E3 ubiquitin ligase ligand portion of the compound is selected from:

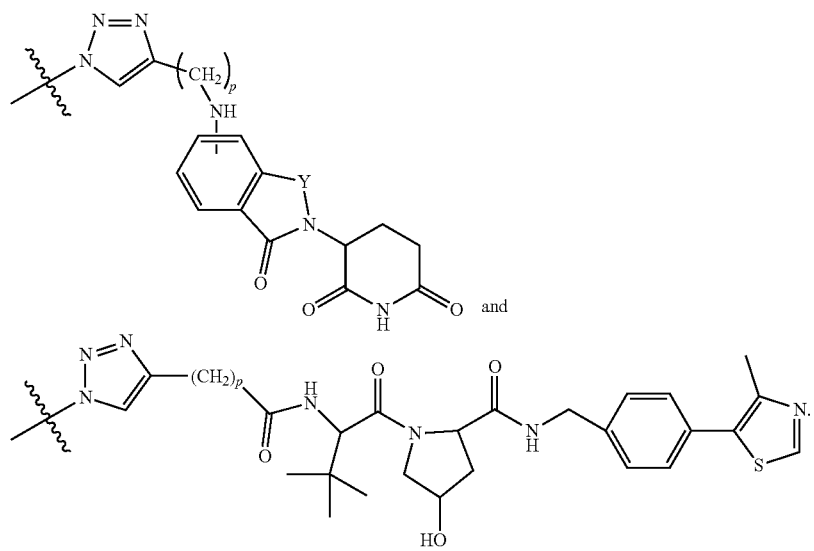

wherein "p" is an integer of from 1 to 6; and salts thereof.

In these preferred compounds, the HDAC6-selective inhibitor portion of the compound can have a C4 positional link:

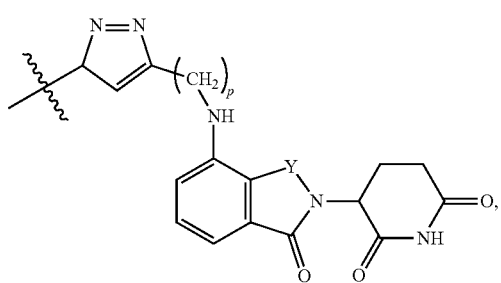

or a C5 positional link:

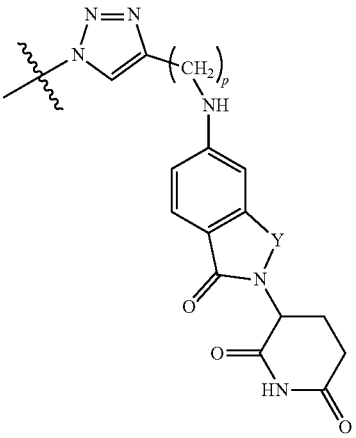

See Scheme 1, below

Also disclosed herein is a method to inhibit neoplastic cell growth. The method comprising contacting a cell with one or more of the compounds disclosed herein.

Additionally, the method may comprise administering to a subject a neoplastic cell growth inhibiting-effective amount of one or more of the compounds disclosed herein.

Lastly, also disclosed herein is a pharmaceutical composition comprising an amount of one or more compounds as recited in Claim 1, in combination with a pharmaceutically suitable carrier. The pharmaceutical composition is useful for inhibiting neoplastic cell growth in mammals (including humans), as well as non-mammalian animals.

BRIEF DESCRIPTION OF THE DRAWINGS

FIG. 12A shows dose response of 12d at a concentration from 0.3 nM to 10 µM. FIG. 12B shows time-course change of protein expression under treatment of 12d at 100 nM. FIG. 12C shows a comparison of HDAC6 degraders and HDAC inhibitors.

FIGS. 14A and 14B demonstrate the antiproliferative action of 12d in multiple myeloma. FIG. 14A is a histogram depicting cell viability of MM1S cells treated with compounds at 1 µM for 72 h. FIG. 14B is a graph showing cell viability of MM1S cells treated with compounds at concentrations from 0.3 nM to 3 µM for 72 h. All data were normalized to vehicle (DMSO)-treated group and dot plot represented as mean of relative viability (n=3) with ±SD as error bar. For the curve in FIG. 14B, nonlinear fitting of inhibitor concentration vs. response (three parameters) was generated by GraphPad Prism with $R^2$ from 0.92 to 0.97. Statistical significance was analyzed by one-way ANOVA for FIG. 14A and two-way ANOVA for FIG. 14B. Not significant (ns) P>0.05, *P≤0.05, P≤0.01, *P≤0.001, ****P≤0.0001.

DETAILED DESCRIPTION

Abbreviations and Definitions

Figure 1:
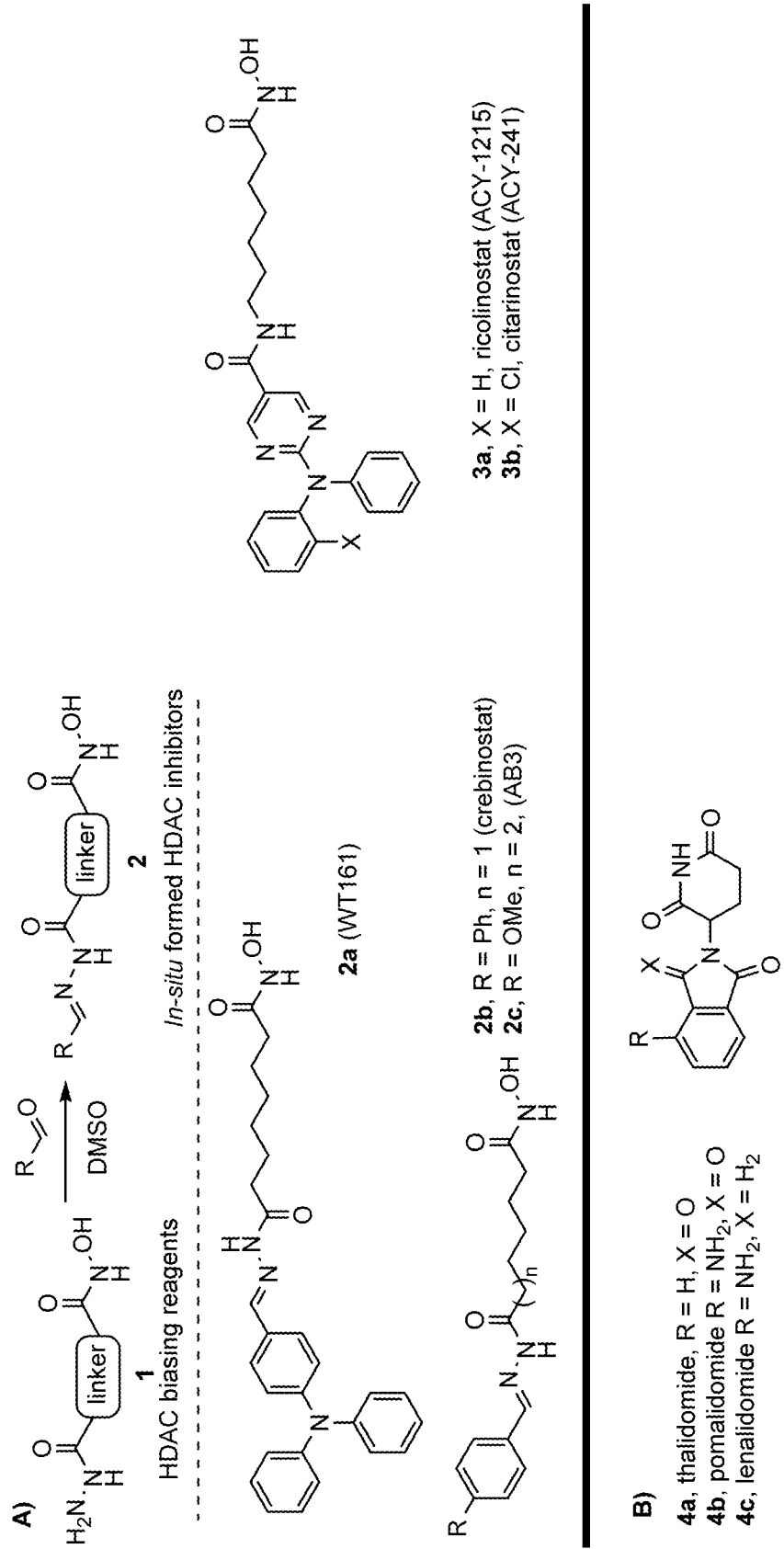
FIG. 1: Panel A depicts a prior art strategy for generating HDAC inhibitors. Panel B depicts the prior art CRBN R3 ubiquitin ligase ligands thalidomide, pomalidomide (sold in the U.S. under the trademark "POMALYST" ® and in Europe under the trademark "Imnovid" by Celegene Corporation, Summit, N.J.) and lenalidomide (sold in the U.S. under the trademark "REVLIMID" ®; Celgene, Corporation).

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage. For example, "one or more" substituents on a phenyl ring designates one to five substituents.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

The term "contacting" refers to the act of touching, making contact, or of bringing to immediate or close proximity, including at the molecular level, for example, to bring about a chemical reaction, or a physical change, e.g., in a solution or in a reaction mixture.

CRBN=Cereblon.
DCM=dichloromethane.
DIPEA=N,N-Diisopropylethylamine.
DMF=Dimethylformamide.
DMSO=Dimethyl sulfoxide.
ELISA=Enzyme-linked Immunosorbent Assay.
IAP=Inhibitor of Apoptosis Protein.
HDAC6=Histone deacetylase 6.
IMiD=immunomodulatory drug.
IKZF=Ikaros family of zinc fingers.
MM1S (also known as MM.1S) is a human B lymphoblast cell line. It is available from ATCC under accession number ATCC CRL-2974. (American Type Culture Collection, Manassas, Va., USA.)
PARP=poly-ADP ribose polymerase.
Poma=Pomalidomide.
PROTAC=proteolysis targeting chimeras.
SAHA, Suberoylanilide hydroxamic acid (Vorinostat)
SD=Standard Deviation.
TBTA=Tris((1-benzyl-4-triazolyl)methyl)amine.
tBuOH=tert-butyl alcohol.
VHL, Von Hippel-Lindau tumor suppressor (a type of E3 ubiquitin ligase).

An "effective amount" refers to an amount of a chemical or reagent effective to facilitate a chemical reaction between two or more reaction components, and/or to bring about a recited effect. Thus, an "effective amount" generally means an amount that provides the desired effect.

"E3 ligase" (also known as "ubiquitin ligase," "ubiquitin-protein ligase," and "E3 ubiquitin ligase") refers to enzymes falling within Enzyme Commission/Classification ("EC") 6.3.2.1. These enzymes function to recruit an E2 ubiquitin-conjugating enzyme that has been loaded with ubiquitin, recognizes a protein substrate, and assists or directly catalyzes the transfer of ubiquitin from the E2 to the protein substrate. The three substrates of an E3 ligase are ATP, ubiquitin, and a lysine residue on a protein; the three products of the reaction are AMP, diphosphate, and protein N-ubiquityl-lysine. Canonical ubiquitylation creates an isopeptide bond between a lysine residue on a target protein and the ubiquitin C-terminal Gly-76. In humans, E3 ligases regulate homeostasis, cell cycle, and DNA repair pathways. As a result, defects in certain E3 ligases have been implicated in a variety of cancers, including MDM2, BRCA1, and Von Hippel-Lindau tumor suppressor.

"Histone Deacetylase," abbreviated herein as "HDAC" refers to enzymes falling within EC 3.5.1.98 and generally assigned CAS No. 9076-57-7. Histone deacetylases are a class of enzymes that remove acetyl groups, —(O=C)—CH$_3$, from an e-N-acetyl lysine amino acid residue in a histone protein. The action of HDAC's is crucial to normal cell function because DNA in vivo is wrapped around histones and DNA expression is regulated by acetylation and de-acetylation. The action of HDACs is opposite to that of histone acetyltransferases, which acetylate a histone substrate. As used herein "histone deacetylase" is synonymous with the newer term "lysine deacetylase," which is typically abbreviated "KDAC." Histone deacetylases are divided into five (5) classes (I, IIA, IIB, III, and IV) based on sequence homology to the HDAC found in yeast, and further subdivided into sub-classes HDAC1 through HDAC10 and SIRT1 through SIRT7, based on the substrate upon which the HDAC enzyme acts. HDAC6, for example, falls within class IIB and typically acts upon c-tubulin, heat shock protein 90 ("HSP90"), nuclear receptor subfamily 0, group B, member 2 protein ("NR0B2" or "SHP"—small heterodimer partner), and mothers against decapentaplegic homolog 7 protein ("SMAD7").

As used herein "ligand" means a moiety that forms a complex with a biomolecule, typical a proteinaceous receptor, to serve a biological purpose. In protein-ligand binding, the ligand is a molecule or part of a molecule which produces a signal by binding to a site on a target protein. The binding typically results in a change of conformational isomerism (conformation) of the target protein. The term "ligand" is defined broadly herein to designate any organic compound or moiety thereof for which a receptor naturally exists or can be prepared.

A "pharmaceutically suitable salt" is any acid or base addition salt whose counter-ions are non-toxic to a patient (including a veterinary patient) in pharmaceutical doses of the salts, so that the beneficial pharmacological effects inherent in the free base or free acid are not vitiated by side effects ascribable to the counter-ions. A host of pharmaceutically suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis-b-hydroxynaphthoates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. See P. Heinrich Stahl and Camille G. Wermuth, Eds. "Handbook of Pharmaceutical Salts: Properties, Selection, and Use; 2nd Revised Edition," © 2011, Wiley-VCH (Hoboken, N.J.), ISBN 978-3906390512.

The Approach:

In order to develop small molecules for targeted protein destruction, one generally needs to address three issues:

1) identify the ligand for the protein of interest and the solvent-exposing sites of this ligand;

2) identify the solvent exposing sites of the E3 ligase ligands; and 3) find an appropriate linker length between the protein of interest ligand and the E3 ligase ligand to allow the exposure of appropriate lysine residues on the protein of interest to the ubiquitin ligase.

Using this approach, disclosed herein are first-in-class HDAC6-selective degraders comprising an HDAC inhibitor covalently linked via a linker to an E3 ubiquitin ligase ligand. Specifically regarding degradation of HDAC6 activity, it is notable that genetic knockout mutations of most HDACs are lethal. However, HDAC6 knockout mice are viable and develop normally. See Zhang, Y.; Kwon, S.; Yamaguchi, T.; Cubizolles, F.; Rousseaux, S.; Kneissel, M.; Cao, C.; Li, N.; Cheng, H. L.; Chua, K.; Lombard, D.; Mizeracki, A.; Matthias, G.; Alt, F. W.; Khochbin, S.; Matthias, P. "Mice Lacking Histone Deacetylase 6 Have Hyperacetylated Tubulin but Are Viable and Develop Normally" *Mol. Cell Biol.* 2008, 28, 1688, and Batchu, S. N.; Brijmohan, A. S.; Advani, A. "The Therapeutic Hope for Hdac6 Inhibitors in Malignancy and Chronic Disease" *Clin. Sci.* 2016, 130, 987. The HDAC6 degraders are attractive drug candidates because mammals remain viable even when they are completely lacking in HDAC6 activity.

The bifunctional structure of the disclosed compounds is characterized by one end of the molecule being structured to bind with high selectivity to an E3 ubiquitin ligase while the other end is structured to bind to an HDAC generally and an HDAC6 specifically. As the binding events unfold, the exposed lysine residues of the HDAC are brought in close contact to the E3 ligase complex, are poly-ubiquitinated, and thus are targeted for degradation by proteasomes. The bifunctional degrader is released by the degradation of the HDAC to continue its catalytic activity for the degradation of additional HDAC molecules.

The HDAC-Specific Degraders:

A series of building blocks 1 (see FIG. 1) was developed to provide quick access to a library of diverse histone deacetylase inhibitors 2. (Tang, W.; Luo, T.; Greenberg, E. F.; Bradner, J. E.; Schreiber, S. L. "Discovery of Histone Deacetylase 8 Selective Inhibitors" *Bioorg. Med. Chem. Lett.* 2011, 21, 2601. PMCID3403710) One member of the library, 2a (WT161), is highly effective for treating bortezomib-resistant multiple myeloma in cells and mouse models when combined with bortezomib. Hideshima, T.; Qi, J.; Paranal, R. M.; Tang, W.; Greenberg, E.; West, N.; Colling, M. E.; Estiu, G.; Mazitschek, R.; Perry, J. A.; Ohguchi, H.; Cottini, F.; Mimura, N.; Gorgun, G.; Tai, Y. T.; Richardson, P. G.; Carrasco, R. D.; Wiest, O.; Schreiber, S. L.; Anderson, K. C.; Bradner, J. E. "Discovery of Selective Small-Molecule Hdac6 Inhibitor for Overcoming Proteasome Inhibitor Resistance in Multiple Myeloma" *Proc. Natl. Acad. Sci. USA* 2016, 113, 13162. WT161 is currently sold by several companies as a chemical probe for selectively inhibiting HDAC6, and it is also the prototype compound for clinical candidates 3a and 3b. The Hideshima et al. study (supra) on WT-161 established the foundation for the treatment of multiple myeloma and other cancers by 3a and 3b in several human clinical trials. See also, for example, Cosenza et al. 2016, supra. WT-161 and its analogues were licensed to Acetylon, which was recently acquired by Celgene Corporation (Summit, N.J.). Thalidomide 4a, pomalidomide 4b, lenalidomide 4c, and their related analogues are ligands of the cereblon (CRBN) E3 ubiquitin ligase, and they are currently used clinically for the treatment of multiple myeloma. See Ito, T.; Ando, H.; Suzuki, T.; Ogura, T.; Hotta, K.; Imamura, Y.; Yamaguchi, Y.; Handa, H. "Identification of a Primary Target of Thalidomide Teratogenicity" *Science* 2010, 327, 1345, Kronke, J.; Udeshi, N. D.; Narla, A.; Grauman, P.; Hurst, S. N.; McConkey, M.; Svinkina, T.; Heckl, D.; Comer, E.; Li, X. Y.; Ciarlo, C.; Hartman, E.; Munshi, N.; Schenone, M.; Schreiber, S. L.; Carr, S. A.; Ebert, B. L. "Lenalidomide Causes Selective Degradation of Ikzf1 and Ikzf3 in Multiple Myeloma Cells" *Science* 2014, 343, 301, and Lu, G.; Middleton, R. E.; Sun, H. H.; Naniong, M.; Ott, C. J.; Mitsiades, C. S.; Wong, K. K.; Bradner, J. E.; Kaelin, W. G. "The Myeloma Drug Lenalidomide Promotes the Cereblon-Dependent Destruction of Ikaros Proteins" *Science* 2014, 343, 305. Another member of the library, 2b (crebinostat), increased the density of synapsin-1 punctae along dendrites in cultured neurons and enhanced memory in mouse models. (Fass, D. M.; Reis, S. A.; Ghosh, B.; Hennig, K. M.; Joseph, N. F.; Zhao, W. N.; Nieland, T. J. F.; Guan, J. S.; Kuhnle, C. E. G.; Tang, W. P.; Barker, D. D.; Mazitschek, R.; Schreiber, S. L.; Tsai, L. H.; Haggarty, S. J. "Crebinostat: A Novel Cognitive Enhancer That Inhibits Histone Deacetylase Activity and Modulates Chromatin-Mediated Neuroplasticity" *Neuropharmacology* 2013, 64, 81.) Another member of the library, compound 2c, suppresses aggressive thyroid cancer in cells and in animal models. Jaskula-Sztul, R.; Eide, J.; Tesfazghi, S.; Dammalapati, A.; Harrison, A. D.; Yu, X.-M.; Scheinebeck, C.; Winston-McPherson, G.; Kupcho, K. R.; Robers, M. B.; Hundal, A. K.; Tang, W.; Chen, H. "Tumor-Suppressor Role of Notch3 in Medullary Thyroid Carcinoma Revealed by Genetic and Pharmacological Induction" *Mol. Cancer Ther.* 2015, 14, 499, and Jang, S.; Yu, X. M.; Odorico, S.; Clark, M.; Jaskula-Sztul, R.; Schienebeck, C. M.; Kupcho, K. R.; Harrison, A. D.; Winston-McPherson, G. N.; Tang, W.; Chen, H. "Novel Analogs Targeting Histone Deacetylase Suppress Aggressive Thyroid Cancer Cell Growth and Induce Re-Differentiation" *Cancer Gene Ther.* 2015, 22, 410.

Figure 2:
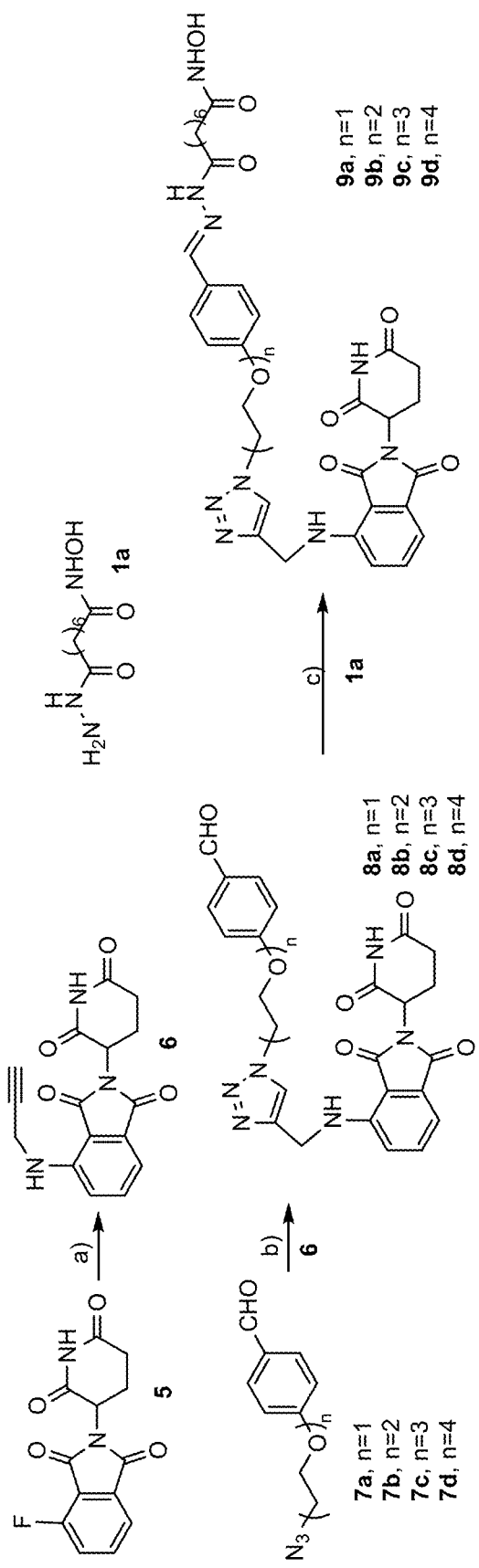
FIG. 2: Synthesis of HDAC degraders derived from non-selective HDAC inhibitors

A first generation of HDAC degraders 9a-9d was made by linking pan-HDAC inhibitors and a thalidomide-type of E3 ubiquitin ligase ligands with various linkers as shown in FIG. 2. See Yang, K.; Song, Y.; Xie, H.; Wu, H.; Wu, Y.-T.; Leisten, E. D.; Tang W. "Development of the first small molecule histone deacetylase 6 (HDAC6) degraders." *Bioorg. Med. Chem. Lett.* 2018, 28, 2493-2497. As shown in FIG. 2, Reaction (a) takes place in the presence of propargylamine hydrochloride, DIPEA, and DMF at 90° C. Reaction (b) uses $CuSO_4$, TBTA, sodium ascorbate, $H_2O$/tBuOH (1:5), at room temperature; Reaction (c) uses acetic acid, 0.1 M substrate, and DMSO, at 65° C.

Figure 3A:
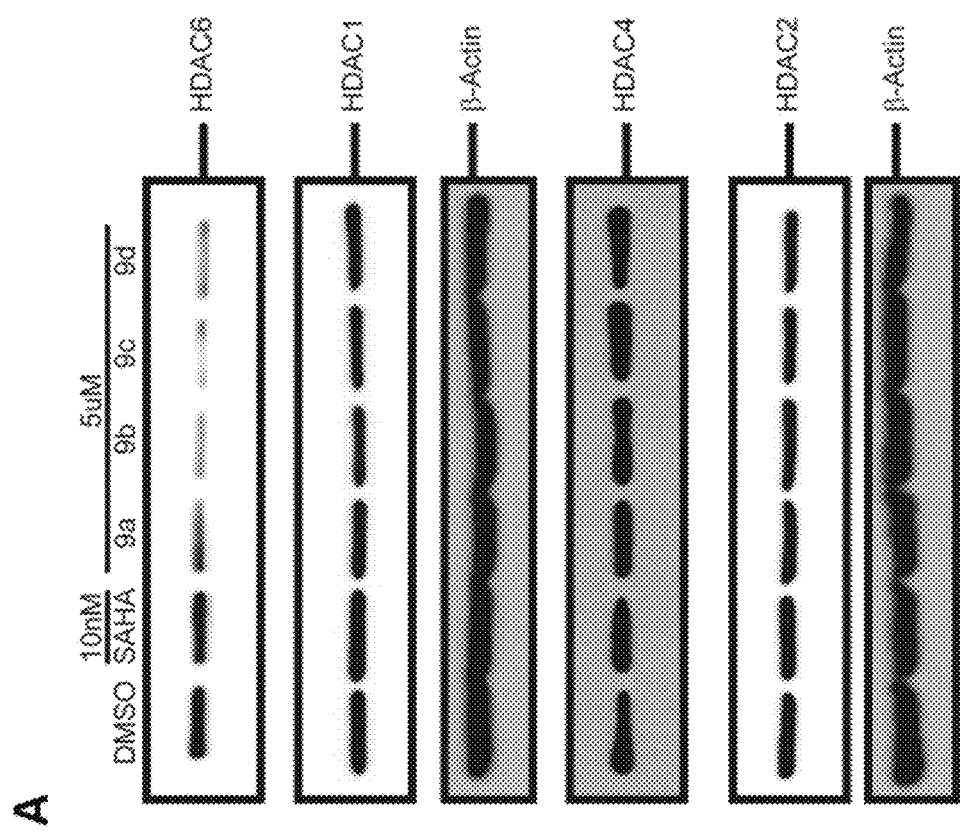
FIG. 3A: Immunoblot of whole cell lysate after MCF-7 cells were treated with 5 µM of 9a-9d for 12 h.
Figure 3B:
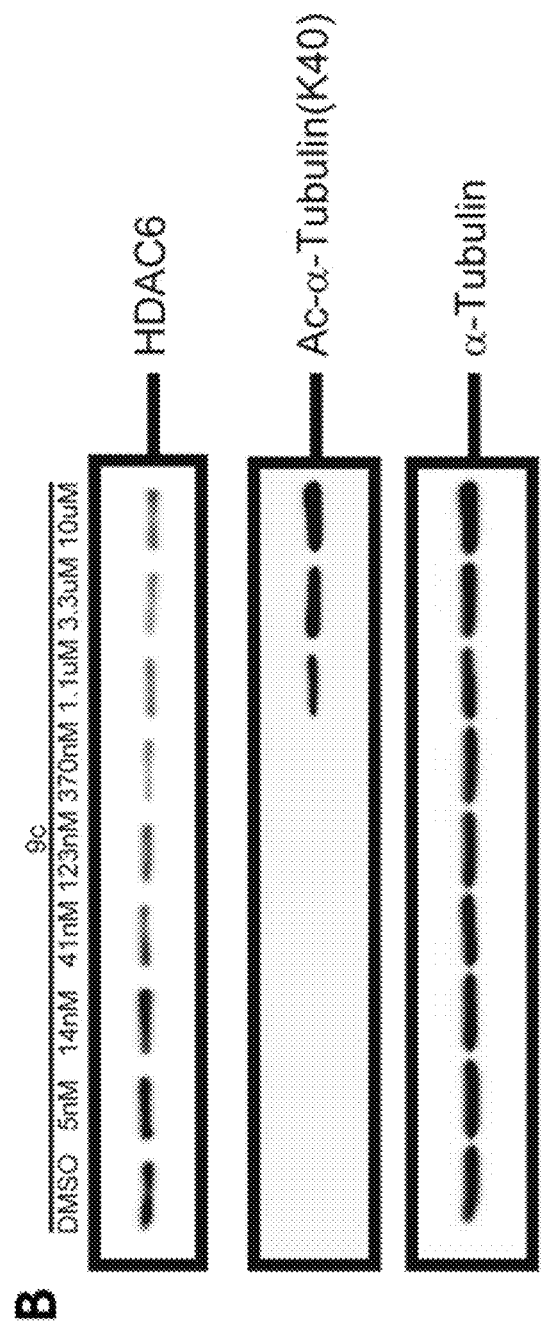
FIG. 3B: Immunoblot of whole cell lysate after MCF-7 cells were treated with 9c at various concentrations (5 nM to 10 µM) for 12 h.
Figure 3C:
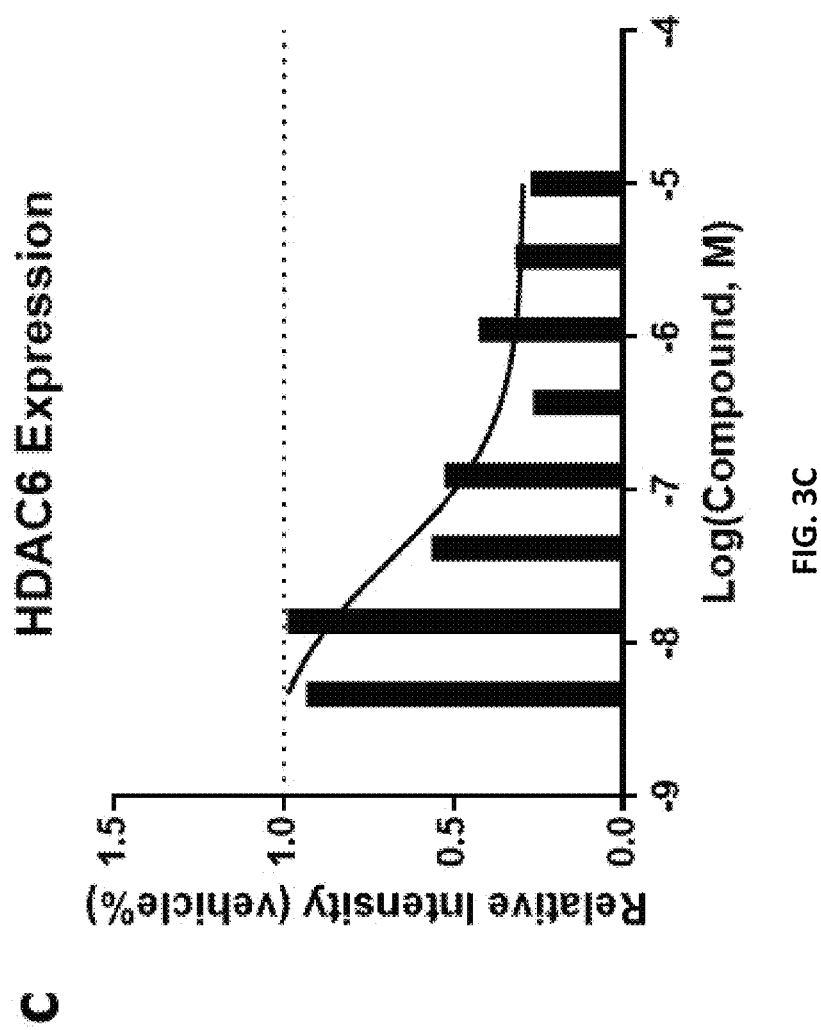
FIG. 3C: Band intensity of the immunoblot shown in FIG. 3B calculated using "Image J" software (a public domain, Java-based image processing program developed at the National Institutes of Health and only available online at https://imagej.nih.gov/ij/) and curve-fit and graphed using GraphPad's "Prism"-brand software (GraphPad Software, Inc. La Jolla, Calif.).

The activity and selectivity of HDAC degraders 9a-9d was tested in cell-based assays against different HDACs. It was found that compounds 9a-9d degrade HDAC6 preferentially over HDAC1, HDAC2, and HDAC4 in MCF7 cells. The corresponding gels, arranged in registration, are shown in FIG. 3A. The degradation of HDAC6 induced by compound 9c led to the increase of acetylated tubulin as expected from the initial results. See FIG. 3B. The concentration at which half-maximal degradation was achieved ($DC_{50}$) and the maximum percentage of degradation ($D_{max}$) were 34 nM and 70.5% respectively. See FIGS. 3B and 3C. These data establish that these compounds are the first-in-class HDAC6-selective degraders known in the art. Surprisingly, compound 9c, which uses a non-selective HDAC targeting ligand was converted to a selective HDAC6 degrader for reasons that remain unclear. The maximal degradation effect was observed at around 300 nM for compound 9c and this can be rationalized by the "hook effect". Douglass, E. F.; Miller, C. J.; Sparer, G.; Shapiro, H.; Spiegel, D. A. "A Comprehensive Mathematical Model for Three-Body Binding Equilibria" *J. Am. Chem. Soc.* 2013, 135, 6092.

To prepare bifunctional small molecule degraders targeting HDAC6 more selectively, HDAC6-selective targeting moieties were identified and utilized. A number of selective HDAC6 selective inhibitors have been reported in the literature.[22,42-48] See Kalin et al. 2013, supra, and Lin, X. F.; Chen, W. M.; Qiu, Z. X.; Guo, L.; Zhu, W.; Li, W. T.; Wang, Z. G.; Zhang, W. X.; Zhang, Z. S.; Rong, Y. P.; Zhang, M. F.; Yu, L. J.; Zhong, S.; Zhao, R.; Wu, X. H.; Wong, J. C.; Tang, G. Z. "Design and Synthesis of Orally Bioavailable Aminopyrrolidinone Histone Deacetylase 6 Inhibitors" *J. Med. Chem.* 2015, 58, 2809, De Vreese, R.; Depetter, Y.; Verhaeghe, T.; Desmet, T.; Benoy, V.; Haeck, W.; Van Den Bosch, L.; D'Hooghe, M. "Synthesis and Sar Assessment of Novel Tubathian Analogs in the Pursuit of Potent and Selective Hdac6 Inhibitors" *Org. Biomol. Chem.* 2016, 14, 2537, Goracci, L.; Deschamps, N.; Randazzo, G. M.; Petit, C.; Passos, C. D.; Carrupt, P. A.; Simoes-Pires, C.; Nurisso, A. "A Rational Approach for the Identification of Non-Hydroxamate Hdac6-Selective Inhibitors" *Sci. Rep.* 2016, 6, Senger, J.; Melesina, J.; Marek, M.; Romier, C.; Oehme, I.; Witt, O.; Sippl, W.; Jung, M. "Synthesis and Biological Investigation of Oxazole Hydroxamates as Highly Selective Histone Deacetylase 6 (Hdac6) Inhibitors" *J. Med. Chem.* 2016, 59, 1545, Shen, S. D.; Benoy, V.; Bergman, J. K.; Kalin, J. H.; Frojuello, M.; Vistoli, G.; Haeck, W.; Van Den Bosch, L.; Kozikowski, A. P. "Bicyclic-Capped Histone Deacetylase 6 Inhibitors with Improved Activity in a Model of Axonal Charcot-Marie-Tooth Disease" *ACS Chem. Neurosci.* 2016, 7, 240, Yang, Z.; Wang, T. J.; Wang, F.; Niu, T.; Liu, Z. W.; Chen, X. X.; Long, C. F.; Tang, M. H.; Cao, D.; Wang, X. Y.; Xiang, W.; Yi, Y. Y.; Ma, L.; You, J. S.; Chen, L. J. "Discovery of Selective Histone Deacetylase 6 Inhibitors Using the Quinazoline as the Cap for the Treatment of Cancer" *J. Med. Chem.* 2016, 59, 1455, and De Vreese, R.; Galle, L.; Depetter, Y.; Franceus, J.; Desmet, T.; Van Hecke, K.; Benoy, V.; Van Den Bosch, L.; D'Hooghe, M. "Synthesis of Potent and Selective Hdac6 Inhibitors Bearing a Cyclohexane- or Cycloheptane-Annulated 1,5-Benzothiazepine Scaffold" *Chem. Eur. J.* 2017, 23, 128. A second generation of novel HDAC6-selective degraders was prepared by linking known HDAC6-selective inhibitors with E3 ligase ligands such as the thalidomide analogues shown in FIGS. 4 and 5.

Figure 6A:
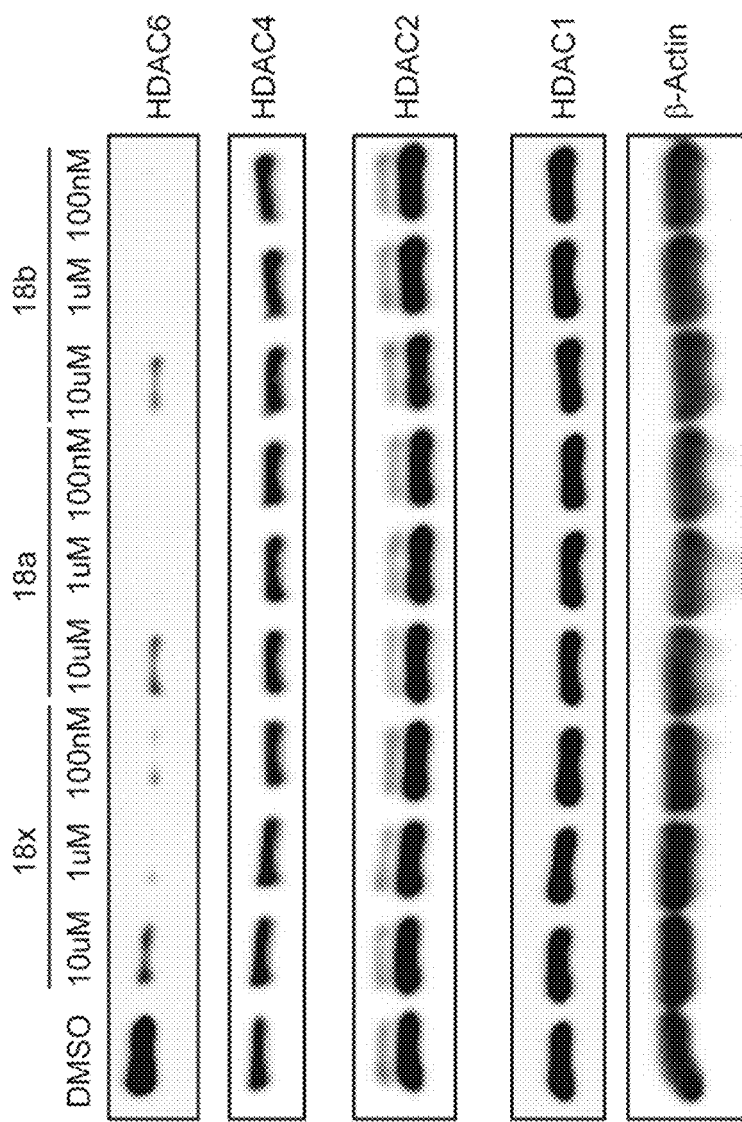
FIG. 6A: Immunoblot showing degradation activity of 18x, 18a, and 18b against HDAC1, HDAC2, HDAC4, and HDAC6 (with β-actin as a control) at serial dilutions of 10 µM, 1 µM, and 100 nM.
Figure 6B:
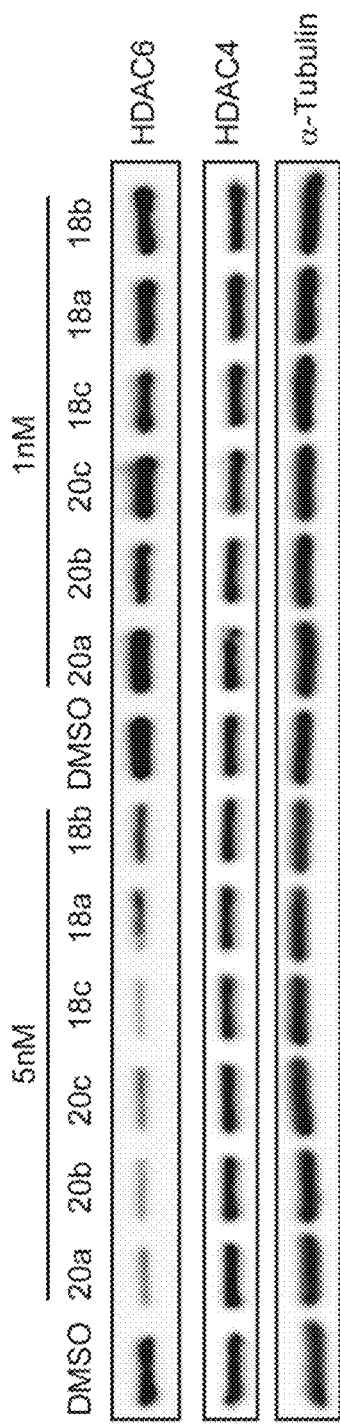
FIG. 6B: Immunoblot showing degradation activity of 20a, 20b, 20c, 18c, 18a, and 18b against HDAC4 and HDAC6 (with α-tubulin as a control) at dilutions of 5 nM and 1 nM.
Figure 6C:
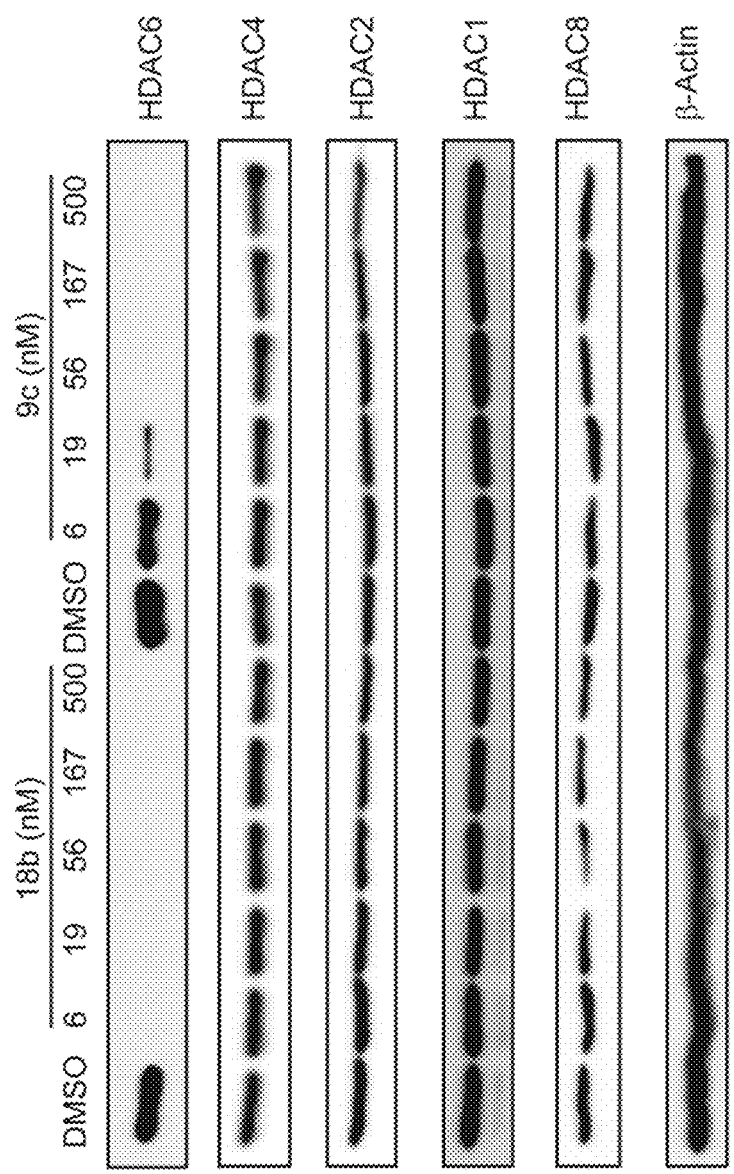
FIG. 6C: Immunoblot showing degradation activity of 18b and 9C against HDAC1, HDAC2, HDAC4, HDAC6, and HDAC8 (with β-actin as a control) at dilutions of 6, 19, 56, 167, and 500 nM.

Some of these HDAC6 degraders could degrade HDAC6 selectively at low nM concentrations in MM. 1S cells (ATCC CRL-2974) as shown in FIGS. 6A, 6B, and 6C. For example, 18b completely depleted HDAC6 at 6 nM concentration.

The second generation of HDAC6 degraders exhibit the following activities: 1) selective inhibition of HDAC6; 2) immunomodulatory functions that are similar to thalidomide analogues; and 3) selective degradation of HDAC6. (See Ito et al. 2010, Kronke et al. 2014, and Lu et al. 2014, supra.) The simultaneous display of these three activities has not been described the prior art literature relevant to HDAC inhibition. Selective degradation of HDAC6 is novel and can only be realized by appropriately tethering a HDAC6 inhibitor to an E3 ligase ligand as described herein.

Alternatively, HDAC degraders can be prepared by linking HDAC6-selective inhibitors with VHL E3 ubiquitin ligase ligand. They can be used together with thalidomide analogues for treating multiple myeloma more effectively.

The additional degradation function for the HDAC6 degraders has a number of advantages: 1) Inhibition of certain cellular pathways increases the expression of the target protein mediated by a feedback mechanism, and this often leads to pharmacological insufficiency. Lai et al. 2017, supra. The degradation activity can then negate the effects of protein overexpression. 2) Domains with non-enzymatic functions often contribute to the diseases, and this can only be corrected by degraders, not inhibitors. 3) The phenotype, or very often the cause, of the diseases is the overexpression of the target protein. The most appropriate correction of the disease state is to tune the level of this protein down to its physiological level instead of inhibiting the enzymatic functions. Attenuating or inhibiting the overexpressed HDAC6 in cancers and other diseases down to its physiological level is a much more effective therapeutic strategy than inhibiting HDAC6. 4) The occupancy-driven pharmacology of inhibitors requires stoichiometric drug binding to the protein of interest in order to modulate the protein function. In contrast, induced protein degradation by targeted protein degradation is event-driven and catalytic, providing favorable pharmacology.

Figures 8A, 8B, 8C:
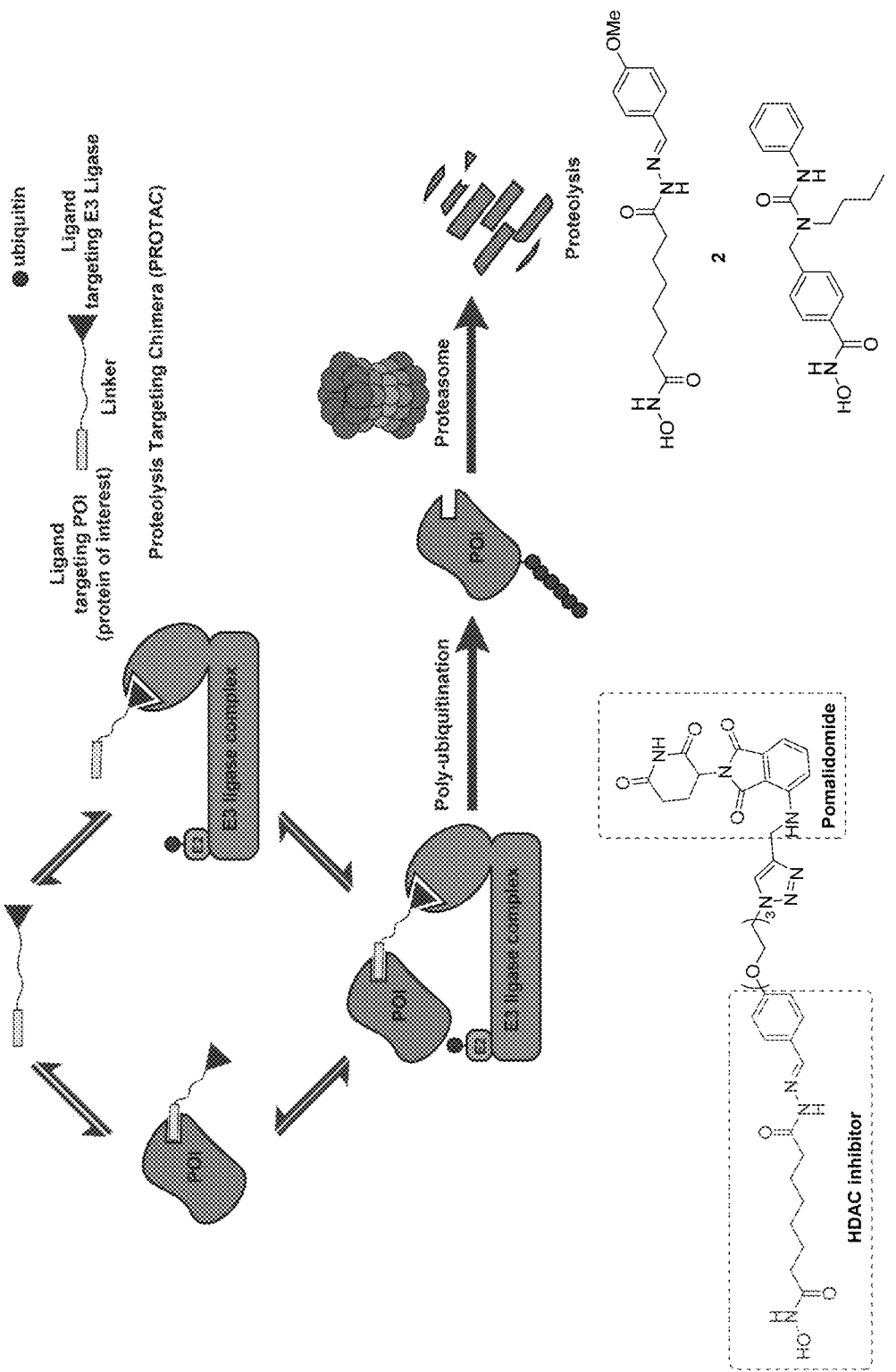
FIG. 8A is a schematic diagram depicting the proteolysis targeting chimera (PROTAC) strategy and HDAC6 degraders, specifically showing PROTAC-induced protein ubiquitination and degradation.
FIG. 8B depicts a previously reported HDAC6 degrader 1.
FIG. 8C depicts the general structure of "warhead"-type HDAC inhibitors, 2 and 3.

Cellular knockdown or silencing the expression of certain functional proteins are important methods and strategies in basic biology research and drug discovery. CRISPR and siRNA knockdown proteins by changing the content of DNA or degrade mRNA. Recently, proteolysis targeting chimeras (PROTACs) became an emerging technique to induce efficient degradation of targeted protein. Lai et al. 2017, supra. See FIG. 8A. PROTACs are rationally designed bifunctional small molecules that are composed of a ligand of E3 ubiquitin ligase, a ligand of protein of interest (POI), and linker between them. The chemical chimera binds to either POI or E3 ligase to form binary complex first. (Gadd, M. S.; Testa, A.; Lucas, X.; Chan, K.; Chen, W.; Lamont, D. J.; Zengerle, M.; Ciulli, A. "Structural Basis of PROTAC Cooperative Recognition for Selective Protein Degradation" *Nat. Chem. Biol.* 2017, 13 (5), 514-521. A subsequent ternary complex formation recruits E3 ligase to be adjacent to the POI and promote its degradation through ubiquitination-proteasome system (UPS). Lai et al. 2017, supra, Buckley, D. L.; Crews, C. M. Small-Molecule Control of Intracellular Protein Levels through Modulation of the Ubiquitin Proteasome System. Angew. Chemie-Int. Ed. 2014, 53 (9), 2312-2330, and Ottis, P.; Crews, C. M. "Proteolysis-Targeting Chimeras: Induced Protein Degradation as a Therapeutic Strategy" *ACS Chem. Biol.* 2017, 12 (4), 892-898.

Up to date, many disease-relevant proteins have been degraded by PROTACs primarily involving three E3 ligases including cereblon (CRBN), Von Hippel-Lindau (VHL), and inhibitor of apoptosis proteins (IAPs). For example, by targeting the degradation of MDM2 or BET, PROTACs exhibited excellent antitumor activity in in-vivo leukemia models. These pre-clinical data underlined the significance of PROTACs in drug discovery. Furthermore, PROTACs are also useful chemical probes for target validation and modulation of cellular functions. See Demizu, Y.; Okuhira, K.; Motoi, H.; Ohno, A.; Shoda, T.; Fukuhara, K.; Okuda, H.; Naito, M.; Kurihara, M. "Design and Synthesis of Estrogen Receptor Degradation Inducer Based on a Protein Knockdown Strategy" Bioorg. Med. Chem. Lett. 2012, 22 (4), 1793-1796, Lu, J.; Qian, Y.; Altieri, M.; Dong, H.; Wang, J.; Raina, K.; Hines, J.; Winkler, J. D.; Crew, A. P.; Coleman, K.; et al. "Hijacking the E3 Ubiquitin Ligase Cereblon to Efficiently Target BRD4" Chem. Biol. 2015, 22 (6), 755-763, Bondeson, D. P.; Smith, B. E.; Burslem, G. M.; Buhimschi, A. D.; Hines, J.; Jaime-Figueroa, S.; Wang, J.; Hamman, B. D.; Ishchenko, A.; Crews, C. M. "Lessons in PROTAC Design from Selective Degradation with a Promiscuous Warhead" Cell Chem. Biol. 2018, 25 (1), 78-87, Zhou, B.; Hu, J.; Xu, F.; Chen, Z.; Bai, L.; Fernandez-Salas, E.; Lin, M.; Liu, L.; Yang, C. Y.; Zhao, Y.; et al. "Discovery of a Small-Molecule Degrader of Bromodomain and Extra-Terminal (BET) Proteins with Picomolar Cellular Potencies and Capable of Achieving Tumor Regression" J. Med. Chem. 2018, 61 (2), 462-481, Nabet, B.; Roberts, J. M.; Buckley, D. L.; Paulk, J.; Dastjerdi, S.; Yang, A.; Leggett, A. L.; Erb, M. A.; Lawlor, M. A.; Souza, A.; et al. "The DTAG System for Immediate and Target-Specific Protein Degradation" Nat. Chem. Biol. 2018, 14 (5), 431-441, Schiedel, M.; Herp, D.; Hammelmann, S.; Swyter, S.; Lehotzky, A.; Robaa, D.; Oláh, J.; Ovádi, J.; Sippl, W.; Jung, M. "Chemically Induced Degradation of Sirtuin 2 (Sirt2) by a Proteolysis Targeting Chimera (PROTAC) Based on Sirtuin Rearranging Ligands (SirReals)" J. Med. Chem. 2018, 61 (2), 482-491, Lai, A. C.; Toure, M.; Hellerschmied, D.; Salami, J.; Jaime-Figueroa, S.; Ko, E.; Hines, J.; Crews, C. M. "Modular PROTAC Design for the Degradation of Oncogenic BCR-ABL" Angew. Chemie-Int. Ed. 2016, 55 (2), 807-810, Burslem, G. M.; Smith, B. E.; Lai, A. C.; Jaime-Figueroa, S.; McQuaid, D. C.; Bondeson, D. P.; Toure, M.; Dong, H.; Qian, Y.; Wang, J.; et al. "The Advantages of Targeted Protein Degradation Over Inhibition: An RTK Case Study" Cell Chem. Biol. 2018, 25 (1), 67-77, Li, Y.; Yang, J.; Aguilar, A.; McEachern, D.; Przybranowski, S.; Liu, L.; Yang, C.-Y.; Wang, M.; Han, X.; Wang, S. "Discovery of MD-224 as a First-in-Class, Highly Potent, and Efficacious Proteolysis Targeting Chimera Murine Double Minute 2 Degrader Capable of Achieving Complete and Durable Tumor Regression" J. Med. Chem. 2019, 62 (2), 448-466, Qin, C.; Hu, Y.; Zhou, B.; Fernandez-Salas, E.; Yang, C.-Y.; Liu, L.; McEachern, D.; Przybranowski, S.; Wang, M.; Stuckey, J.; et al. "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression" J. Med. Chem. 2018, 61 (15), 6685-6704, Winter, G. E.; Buckley, D. L.; Paulk, J.; Roberts, J. M.; Souza, A.; Dhe-Paganon, S.; Bradner, J. E. "Phthalimide Conjugation as a Strategy for in Vivo Target Protein Degradation" Science 2015, 348 (6241), 1376-1381, and Bassi, Z. I.; Fillmore, M. C.; Miah, A. H.; Chapman, T. D.; Maller, C.; Roberts, E. J.; Davis, L. C.; Lewis, D. E.; Galwey, N. W.; Waddington, K. E.; et al. "Modulating PCAF/GCN5 Immune Cell Function through a PROTAC Approach" ACS Chem. Biol. 2018, 13 (10), 2862-2867.

The degradation of Sirt2 by PROTACs was the first published example of degraders for epigenetic "erasers". See Schiedel et al. 20187, supra. Degrader 1 was previously reported as the first PROTAC for zinc-dependent HDACs by conjugating HDAC inhibitors with pomalidomide-linked aldehydes. See FIG. 8B. See also Yang, K.; Song, Y.; Xie, H.; Wu, H.; Wu, Y.-T.; Leisten, E. D.; Tang, "W. Development of the First Small Molecule Histone Deacetylase 6 (HDAC6) Degraders" Bioorg. Med. Chem. Lett. 2018, 28 (14), 2493-2497 and Tang, W.; Luo, T.; Greenberg, E. F.; Bradner, J. E.; Schreiber, S. L. "Discovery of Histone Deacetylase 8 Selective Inhibitors" Bioorg. Med. Chem. Lett. 2011, 21 (9), 2601-2605. Because there was no report on the degradation of any of these Zn-dependent HDACs prior to the present studies described herein, pan-HDAC inhibitor 2 (FIG. 8C) was used as the PROTAC "warhead" to examine which one of these HDACs could be degraded by PROTACs. See Jaskula-Sztul, R.; Eide, J.; Tesfazghi, S.; Dammalapati, A.; Harrison, A. D.; Yu, X.-M.; Scheinebeck, C.; Winston-McPherson, G.; Kupcho, K. R.; Robers, M. B.; et al. "Tumor-Suppressor Role of Notch3 in Medullary Thyroid Carcinoma Revealed by Genetic and Pharmacological Induction" Mol. Cancer Ther. 2015, 14 (2), 499-512 and Jang, S.; Yu, X. M.; Odorico, S.; Clark, M.; Jaskula-Sztul, R.; Schienebeck, C. M.; Kupcho, K. R.; Harrison, A. D.; Winston-Mcpherson, G. N.; Tang, W.; et al. "Novel Analogs Targeting Histone Deacetylase Suppress Aggressive Thyroid Cancer Cell Growth and Induce Re-Differentiation" Cancer Gene Ther. 2015, 22 (8), 410-416. Surprisingly, it was found that compound 1 selectively degraded HDAC6 among the HDACs examined. However, there are several limitations for these HDAC6 degraders. For example, the hydrazone linker is not hydrolytically stable and therefore not very suitable for further studies. Although compound 1 selectively degrades HDAC6, other members of HDACs are still inhibited by the pan-inhibitor "warhead" as demonstrated by the elevated level of acetylated histones. Clearly, the selectivity and potency of HDAC6 degraders need to be improved by using a completely different scaffold for further biological and pharmacological studies. A new generation of selective HDAC6 degraders was therefore designed by attaching E3 ligase ligand to the aniline group of HDAC6 selective inhibitor Nexturastat A (Next-A, 3, FIG. 8C). See Bergman, J. A.; Woan, K.; Perez-Villarroel, P.; Villagra, A.; Sotomayor, E. M.; Kozikowski, A. P. "Selective Histone Deacetylase 6 Inhibitors Bearing Substituted Urea Linkers Inhibit Melanoma Cell Growth" J. Med. Chem. 2012, 55 (22), 9891-9899. During the investigation of the new generation HDAC6 selective degraders, Rao's group reported a class of PROTACs in 2019 by attaching a E3 ligase ligand to the alkyl chain of Next-A.[3] See An, Z.; Lv, W.; Su, S.; Wu, W.; Rao, Y. "Developing Potent PROTACs Tools for Selective Degradation of HDAC6 Protein" Protein Cell 2019. However, their PROTACs did not show any improved anti-proliferation activity over the parent HDAC6 inhibitor Next-A.

Despite the revolution in myeloma therapy in the last two decades, many patients are resistant to currently approved agents Papadas A., Asimakopoulos F. (2017) "Mechanisms of Resistance in Multiple Myeloma." In: Mandalà M., Romano E. (eds) Mechanisms of Drug Resistance in Cancer Therapy. Handbook of Experimental Pharmacology, vol 249. © 2017 Springer, Cham, ISBN 978-3-030-10507-5. HDAC6 selective inhibitors have been used in combination with proteasome inhibitor, immunomodulatory drugs (IMiDs, e.g. pomalidomide and its related analogues), and anti-PD-L1 antibody in anti-myeloma therapeutic development. See Niesvizky, R.; Richardson, P. G.; Yee, A. J.; Nooka, A. K.; Raab, M. S.; Shain, K. H.; Gabrail, N. Y.; Matous, J.; Agarwal, A. B.; Hoffman, J.; et al. "Selective HDAC6 Inhibitor ACY-241, an Oral Tablet, Combined with Pomalidomide and Dexamethasone: Safety and Efficacy of Escalation and Expansion Cohorts in Patients with Relapsed or Relapsed-and-Refractory Multiple Myeloma (ACE-MM-200 Study)" *Blood* 2016, 128 (22), 3307, Santo, L.; Hideshima, T.; Kung, A. L.; Tseng, J.-C.; Tamang, D.; Yang, M.; Jarpe, M.; van Duzer, J. H.; Mazitschek, R.; Ogier, W. C.; et al. "Preclinical Activity, Pharmacodynamic, and Pharmacokinetic Properties of a Selective HDAC6 Inhibitor, ACY-1215, in Combination with Bortezomib in Multiple Myeloma" *Blood* 2012, 119 (11), 2579-2589, Hideshima, T.; Cottini, F.; Ohguchi, H.; Jakubikova, J.; Gorgun, G.; Mimura, N.; Tai, Y.-T.; Munshi, N. C.; Richardson, P. G.; Anderson, K. C. "Rational Combination Treatment with Histone Deacetylase Inhibitors and Immunomodulatory Drugs in Multiple Myeloma" *Blood Cancer J.* 2015, 5 (5), e312-e312, and Ray, A.; Das, D. S.; Song, Y.; Hideshima, T.; Tai, Y.; Chauhan, D.; Anderson, K. C. "Combination of a Novel HDAC6 Inhibitor ACY-241 and Anti-PD-L1 Antibody Enhances Anti-Tumor Immunity and Cytotoxicity in Multiple Myeloma" *Leukemia* 2018, 32 (3), 843-846. HDAC6-selective inhibitors showed synergy with IMiDs for the treatment of multiple myeloma in animal models and human clinical trials. Upon binding to CRBN, pomalidomide analogues are known to activate CRBN's E3 ligase activity towards Ikaros family of zinc fingers (IKZFs) and promote their ubiquitination and subsequent degradation. See Kronke 2014, supra. IKZFs become the neo-substrates of ligand-bound CRBN. The induced degradation of IKZFs by pomalidomide and its analogues are believed to be responsible for their significant anti-proliferation effect in multiple myeloma. Interestingly, PROTACs with IKZF degradation activity have also been reported in a number of cases when pomalidomide was employed as the ligand for CRBN E3 ligase. See, for example, Nabet et al. 2018, supra. The degradation of IKZFs is often considered as undesired during the development of PROTACs. It was hypothesized that multifunctional HDAC6 degraders that retain the degradation activity of IKZFs will have enhanced anti-myeloma activity. The new generation of HDAC6 selective degraders disclosed have distinct advantages in degradation efficiency and selectivity over prior art compounds. The new HDAC6 degraders are also significantly more potent than HDAC6 inhibitor Next-A for the anti-proliferation of multiple myeloma cancer cell lines.

To increase the selectivity and potency of HDAC6 degrader, 19 degraders were made by tethering HDAC6-selective inhibitor Next-A (3) with CRBN E3 ligand Pomalidomide. The general synthetic route is illustrated in Scheme 1. Pomalidomide analogues 4a-e containing alkyne group were synthesized by a $S_NAr$ reaction between fluoro-thalidomide (3a and 3b) and alkyne amine according to literature procedures. (Nabet et al. 2018, supra.) Alkylation of N-Boc protected 4-amino phenol (5) with different dibromoalkanes provided intermediates 6a-e. Subsequent nucleophilic substitution reaction with sodium azide generated compounds 7a-e which were deprotected under boiling water or acidic conditions to give the amines 8a-e. (Wang, J.; Liang, Y.-L.; Qu, J. "Boiling Water-Catalyzed Neutral and Selective N-Boc Deprotection" *Chem. Commun.* 2009, 0 (34), 5144. These amines reacted with secondary amine 9 in the presence of carbonyldiimidazole (CDI) to generate urea esters 10a-e. (Bergman et al. 2012, supra.) The hydroxamic acid group was introduced to 10a-e by utilizing hydroxylamine under basic conditions to afford hydroxamic acids 11a-e. Finally, PROTACs 12a-r with varying linker lengths were obtained by click reactions between azides 11a-e and alkynes 4a-e under typical conditions.

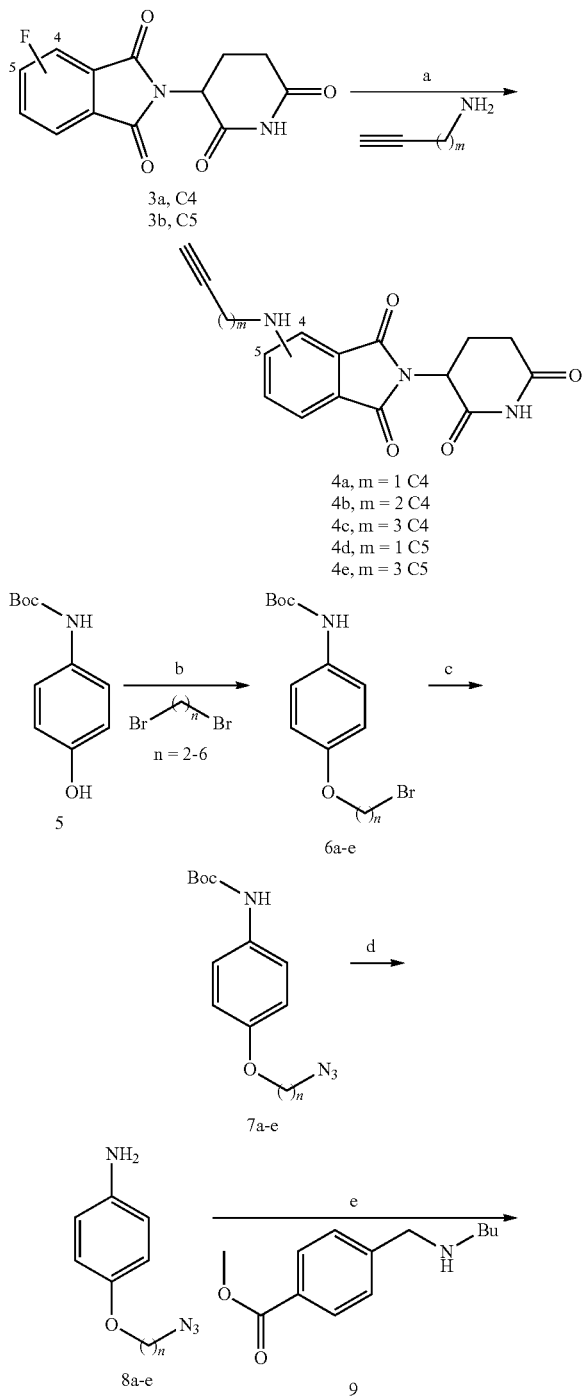

Scheme 1.<sup>a</sup> Synthesis of Compounds 12a-r

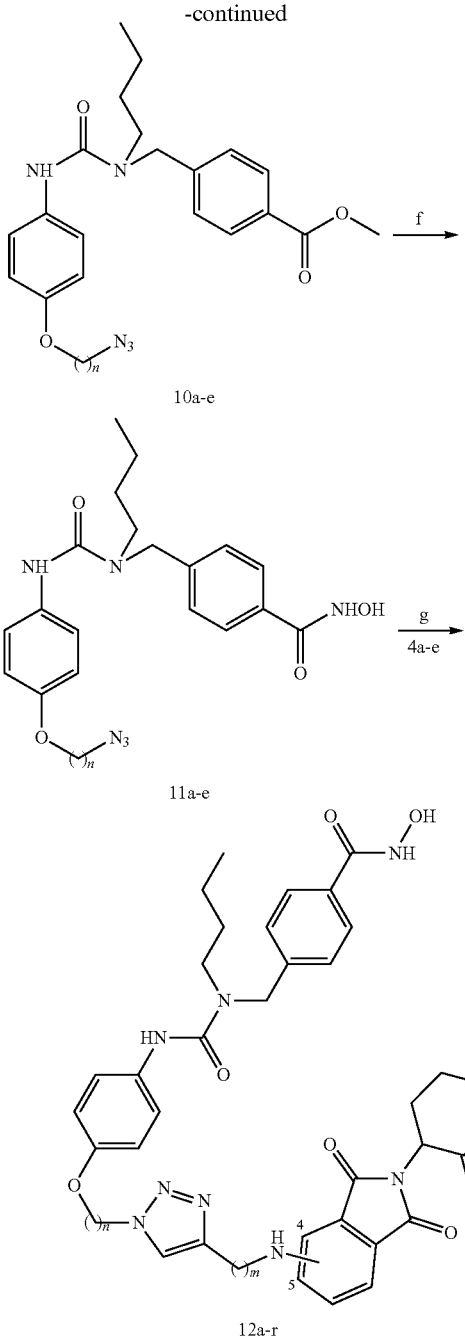

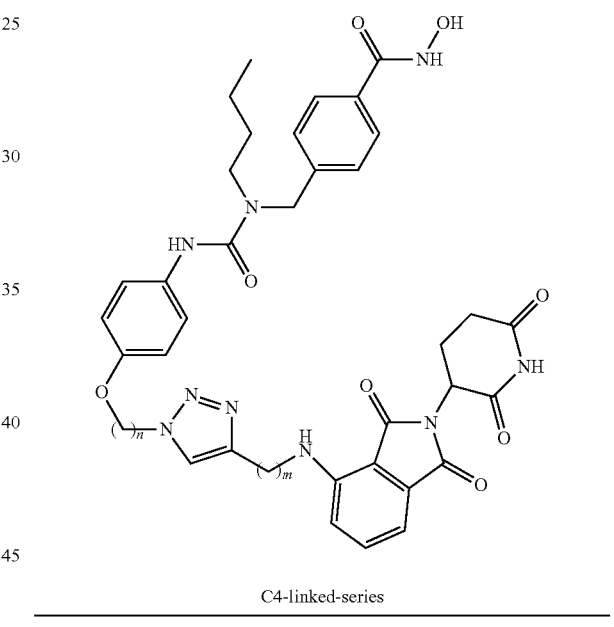

*Reaction conditions:
(a) DIPEA, DMF, 90° C.,17-62%;
(b) K₂CO₃, MaCN, reflux, 45-70%;
(c) NaN₃, DMF, 50° C., 66-90%;
(d) H₂O, Ar reflux or TFA, DCM, 0° C.-rt, 94-97%;
(e) CDI, THF, 0° C.-rt, 13-88%;
(f) NaOH, NH₂OH/H₂O, THF, MeOH, 0° C.-rt, 87-92%;
(g) CuSO₄, sodium ascorbate, TBTA, H₂O/t-BuOH (1:1.5), rt, 14-80%.

These degraders are divided into to two series based on their linking position of the amino group on the phthalimide ring of pomalidomide: C4- or C5-linked series (Table 1). Within each series, the degraders are different from each other by the numbers of carbon atoms between Next-A and the trizole ring (n) or between pomalidomide and the triazole ring (m). It is known that both C-4 and C-5 positions of pomalidomide are exposed to solvent and can be the position to place the linker for PROTACs. Fischer, E. S.; Bohm, K.; Lydeard, J. R.; Yang, H.; Stadler, M. B.; Cavadini, S.; Nagel, J.; Serluca, F.; Acker, V.; Lingaraju, G. M.; et al. "Structure of the DDB1-CRBN E3 Ubiquitin Ligase in Complex with Thalidomide" *Nature* 2014, 512 (7512), 49-53 and Chamberlain, P. P.; Lopez-Girona, A.; Miller, K.; Carmel, G.; Pagarigan, B.; Chie-Leon, B.; Rychak, E.; Corral, L. G.; Ren, Y. J.; Wang, M.; et al. "Structure of the Human Cereblon-DDB1-Lenalidomide Complex Reveals Basis for Responsiveness to Thalidomide Analogs" *Nat. Struct. Mol. Biol.* 2014, 21 (9), 803-809. The para position of the aniline in Next-A was chosen to place the linker because it is well known that the aromatic ring "cap" of HDAC inhibitors is exposed to the solvent. Miyake, Y.; Keusch, J. J.; Wang, L.; Saito, M.; Hess, D.; Wang, X.; Melancon, B. J.; Helquist, P.; Gut, H.; Matthias, P. "Structural Insights into HDAC6 Tubulin Deacetylation and Its Selective Inhibition" *Nat. Chem. Biol.* 2016, 12 (9), 748-754.

TABLE 1

Screening of compounds for HDAC6 degradation activity

C4-linked-series

| Cpd | n | m | Degradation (%)[a] 100 nM | 10 nM |
|---|---|---|---|---|
| 1 | N/A | | 73.5 ± 0.3 | 47.9 ± 0.9 |
| 12a | 2 | 1 | 81.3 ± 2.3 | 62.1 ± 1.0 |
| 12b | 3 | 1 | 84.1 1.0 | 67.3 ± 0.8 |
| 12c | 4 | 1 | 85.0 ± 1.2 | 64.3 ± 3.2 |
| 12d | 5 | 1 | 82.7 ± 1.7 | 74.9 ± 1.2 |
| 12e | 6 | 1 | 77.8 ± 1.7 | 66.1 ± 1.1 |
| 12f | 2 | 2 | 81.8 ± 0.9 | 49.3 ± 0.6 |
| 12g | 3 | 2 | 84.2 ± 0.4 | 64.8 ± 1.0 |
| 12h | 4 | 2 | 79.2 ± 0.9 | 71.7 ± 0.5 |
| 12i | 2 | 3 | 83.1 ± 1.0 | 70.6 ± 1.1 |
| 12j | 3 | 3 | 77.3 ± 1.5 | 45.6 ± 1.6 |
| 12k | 4 | 3 | 75.7 ± 0.8 | 50.9 ± 2.2 |

TABLE 1-continued

Screening of compounds for HDAC6 degradation activity

C5-linked-series

| Cpd | n | m | Degradation (%)[a] 100 nM | 10 nM |
|---|---|---|---|---|
| 12l | 2 | 1 | 81.4 ± 0.6 | 57.1 ± 1.4 |
| 12m | 3 | 1 | 81.2 ± 0.6 | 60.3 ± 1.3 |
| 12n | 4 | 1 | 80.9 ± 0.4 | 63.3 ± 0.8 |
| 12o | 5 | 1 | 84.7 ± 1.0 | 69.9 ± 1.3 |
| 12p | 6 | 1 | 83.5 ± 0.5 | 70.8 ± 0.4 |
| 12q | 2 | 3 | 80.4 ± 0.3 | 47.2 ± 4.8 |
| 12r | 3 | 3 | 81.9 ± 0.4 | 60.9 ± 0.4 |

[a]Degradation percentage calculated from FIG. 2. Degradation percentage represents [100%- mean (± SD) of HDAC6 relative expression of biological replicates (n = 3)].

Figure 9:
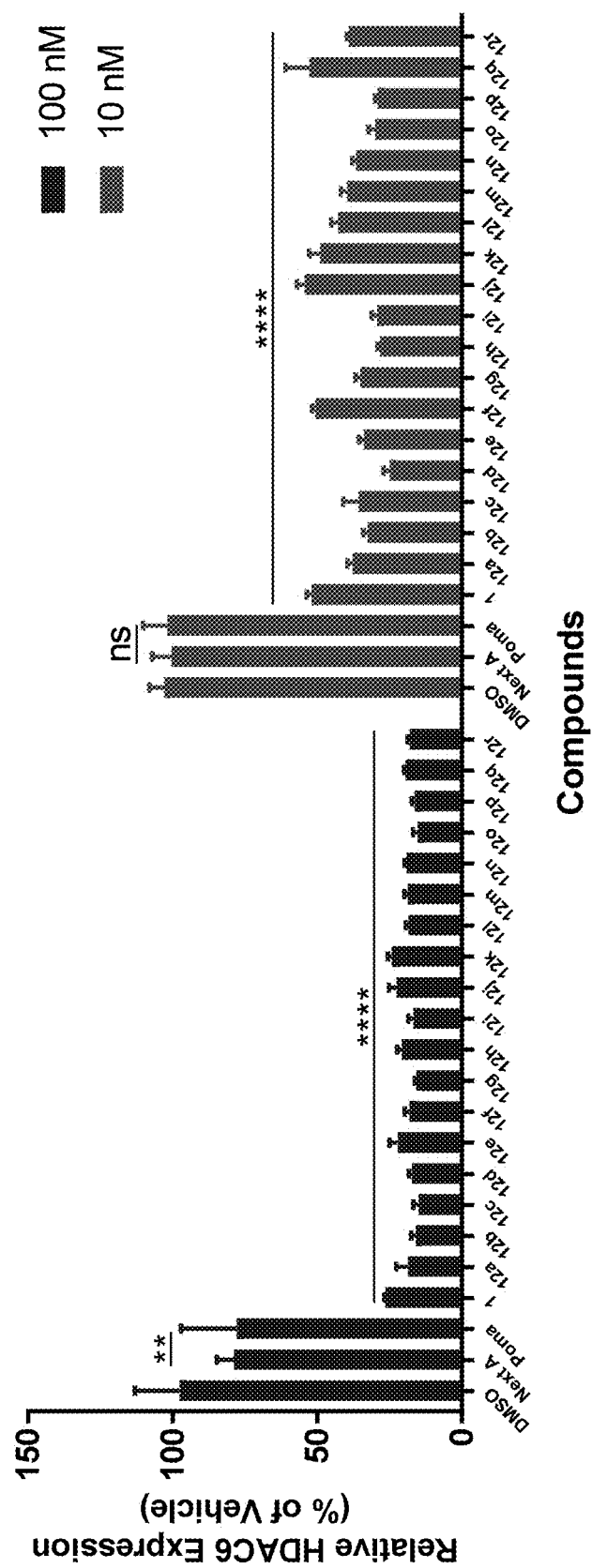
FIG. 9 is a histogram depicting the results of screening of compounds for HDAC6 degradation activity by in-cell ELISA. MM1S cells were treated with compounds at 100 nM (blue bars) or 10 nM (red bars) for 6 h. Data was normalized to vehicle (DMSO)-treated group and the bar graph represents as mean of relative HDAC6 protein level (n=3) with ±SD as error bar. Statistical significance was analyzed by one-way ANOVA. Not significant (ns) P>0.05, *P≤0.05, P≤0.01, *P≤0.001, ****P≤0.0001.

To screen the new series of degraders, an in-cell ELISA assay was developed and validated. The compounds were treated at 100 nM and 10 nM in MM1S cells for 6 h. See FIG. 9. Resulting cells were then fixed and analyzed by in-cell ELISA. Comparing with vehicle, Next-A and pomalidomide didn't affect the expression of HDAC6 at 10 nM and had very minimal effects at 100 nM. At both concentrations, all degraders remarkably decreased the amount of HDAC6 protein. The degradation level was calculated and listed in Table 1. Degraders including 1 at 100 nM degraded 73.5% to 85.0% of HDAC6 with minor difference. At 10 nM concentration of compounds, obvious structure-activity-relationship (SAR) was observed. While only 47.9% of HDAC6 expression was suppressed by the previously reported degrader 1, several new degraders are much more potent. For example, 12d, 12h, 12i, 12o and 12p all achieved about 70% degradation. The C4-linked series, 12d with medium length linker (5+1) achieved most degradation in sub-series 12a-e (m=1). For sub-series 12f-h (m=2), the degradation potency increased when linkers were elongated and 12h (4+2) was the best. Within sub-series 12i-k (m=3), 12i with the shortest linker (2+3) turned out to be the most potent degrader. Among C5-linked series, the potency of sub-series 12l-p (m=1) increased with the linker length. Compounds 12o (5+1) and 12p (6+1) have the similar potency for the degradation of HDAC6. Sub-series 12q-r (m=3) showed relative low effects for the degradation of HDAC6. The above results suggest the optimal total number of methylene units in the linker is about 6 and the C4-linked series are slightly more potent than the C5-series, which might relate to the accessibility of the degrader-recruited E3 ligase to the available ubiquitination site(s) of HDAC6. It appeared that both the distance and linking positions contributed to the degradation efficiency. The rigid triazole ring in the middle of the linker likely modulated the plasticity of degrader-bridged ternary complex.

Figure 10B:
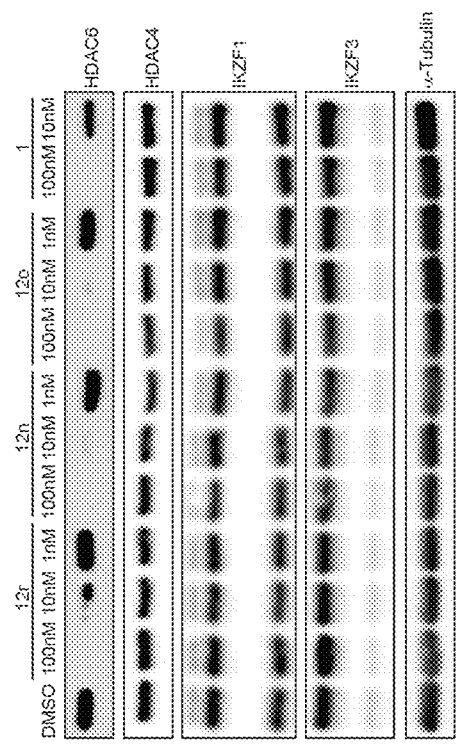
FIGS. 10A and 10B are western blot analysis of MM1S cells treated with selected candidates from C4-lined series (FIG. 10A) and C5-lined series (FIG. 10B) for 6 h.
Figure 10A:
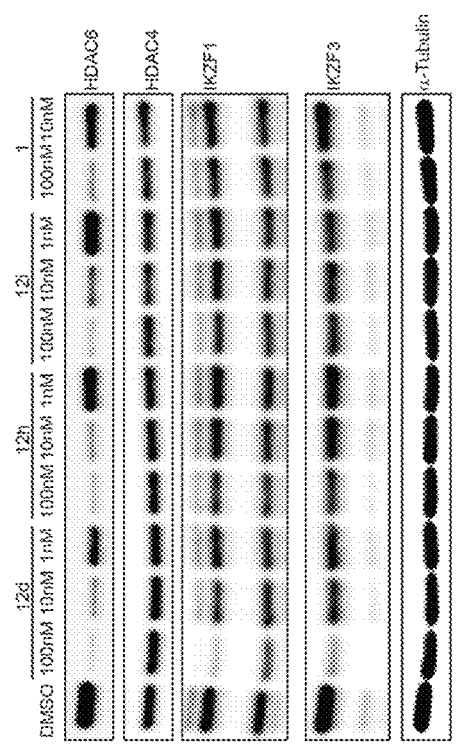

After the identification of the most potent candidates from each sub-series, selected compounds were incubated at 100 nM, 10 nM and 1 nM for western blot analysis. See FIG. 10A and FIG. 10B to confirm the ELISA results. Class II HDAC4 was selected for comparison. For selected compounds from C4- or C5-linked series, all of them presented maximal effects at 100 nM and degraded significant amount of HDAC6 at 10 nM. Clearly, the previous HDAC6 degrader 1 degraded much less HDAC6 at 10 nM concentration. The results from Western blot are consistent with the screening results by ELISA.

As discussed before, pomalidomide and its analogues are known to activate CRBN's E3 ligase activity for the degradation of IKZFs. Interestingly, among the candidates examined, only 12d retained the induced degradation of IKZF1/3 by pomalidomide moiety at 100 nM. IKZFs regulate the expression of interferon regulatory factor 4 (IRF4) and c-Myc to affect the proliferation of multiple myeloma (MM). The downregulation of IKZF 1 and 3 by pomalidomide and its analogues are believed to be responsible for their significant anti-proliferation effect in multiple myeloma. PROTACs with IKZF degradation activity have been reported in a number of cases and the IKZFs are often considered as "off-targets" during the development of these PROTACs. The results presented here indicate that the IKZF degradation activity can be impacted by the linker position and the functional group next to the phthalimide ring. In the studies, the triazole ring linked to C4 position likely contributed to the induced interaction between CRBN and IKZFs.

TABLE 2

$DC_{50}$[a] and $D_{max}$[b] of Selected Degraders

| Cpd | $DC_{50}$ (nM) | $D_{max}$ (Vehicle %) |
|---|---|---|
| 1 | 9.12 ± 1.64 | 84.07 ± 2.41 |
| 12a | 3.41 ± 0.52 | 88.01 ± 2.23 |
| 12d | 1.64 ± 0.24 | 86.26 ± 1.70 |
| 12i | 2.54 ± 0.32 | 86.30 ± 1.67 |

Figure 4:
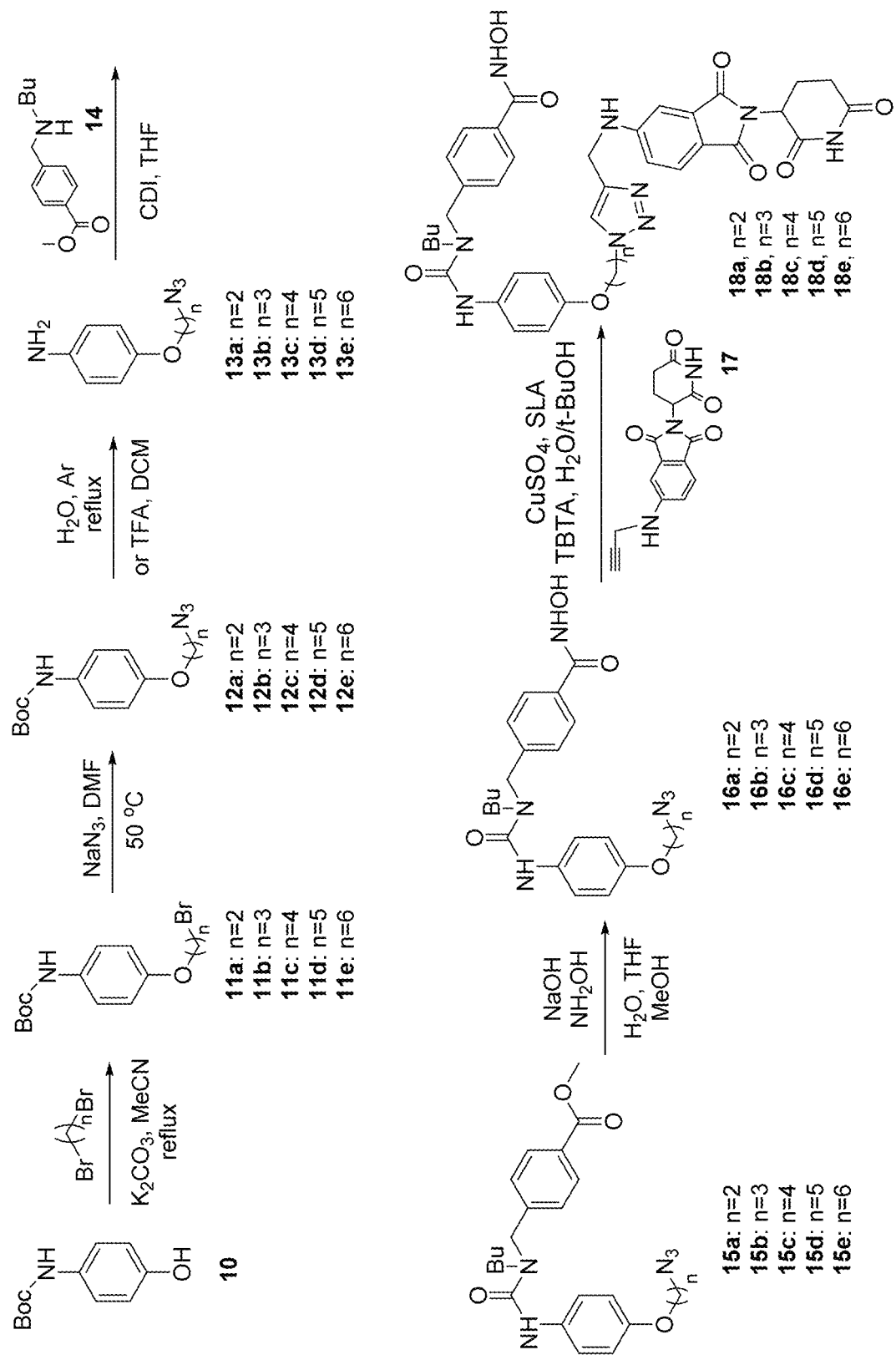
FIG. 4: Synthesis of HDAC degraders derived from selective HDAC inhibitors.
Figure 5:
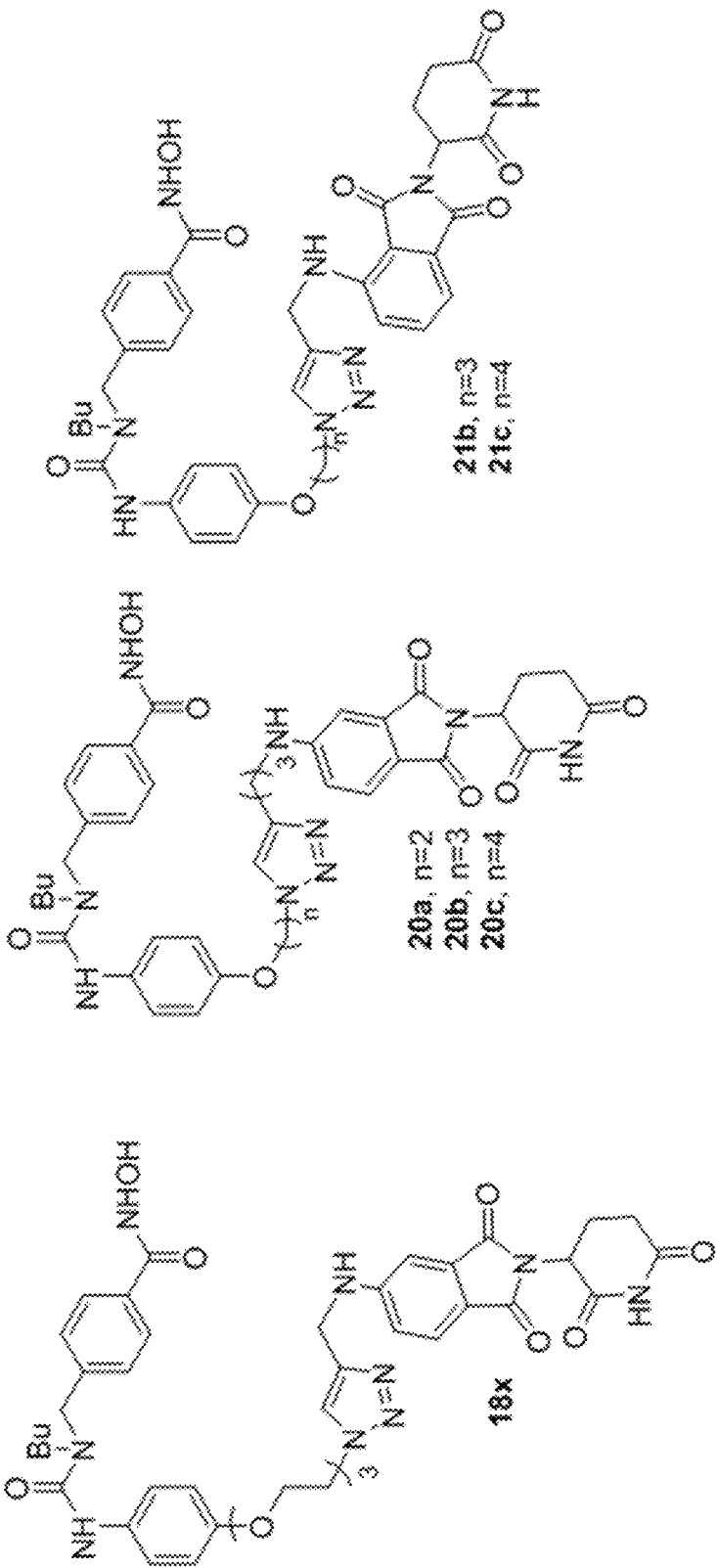
FIG. 5: Analogous compounds made using the route depicted in FIG. 4.

[a]The concentration at which half-maximal degradation was achieved.
[b]The maximum percentage of degradation.
[a,b]Values with ± SD obtained from nonlinear fitted data in FIG. 4.

Figure 11:
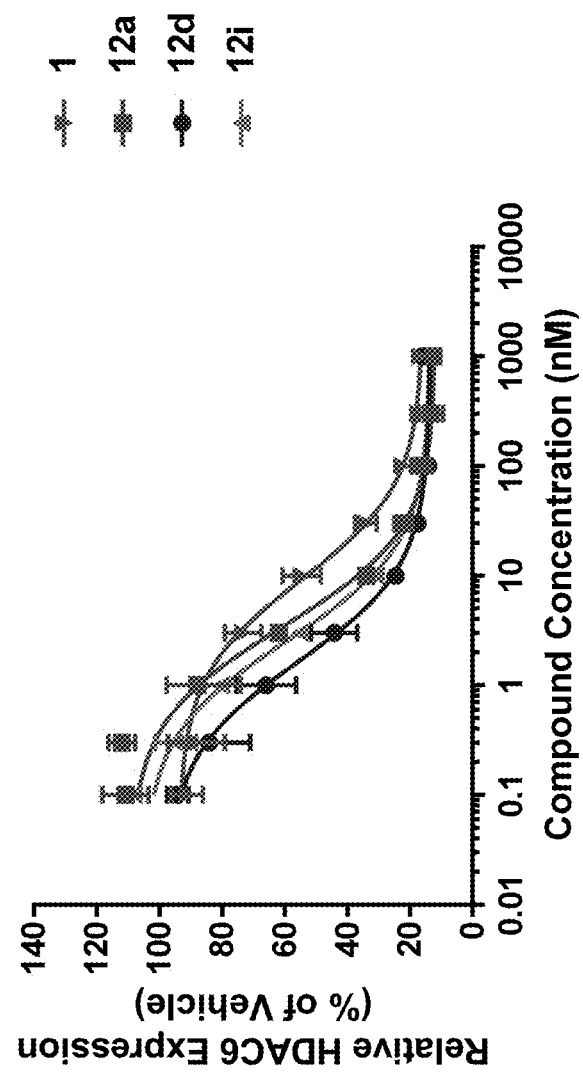
FIG. 11 is a graph depicting dose response of selected degrader candidates. MM1S cells were treated for 6 h and analyzed by in-cell ELISA. Data was normalized to vehicle (DMSO)-treated group and dot plot represented as mean relative expression (n=3) with ±SD as error bar. Nonlinear fitting of inhibitor concentration vs. response (three parameters) was generated by GraphPad Prism with R2 from 0.97 to 0.99.

To examine the potency of the selected candidates, an in-cell ELISA was used to analyze the HDAC6 content in MM1S cells treated with 12a, 12d and 12i and compared them with degrader 1. The amount of cellular HDAC6 was measured in response to concentrations of compounds from 0.1 nM to 1 µM. See FIG. 11. $DC_{50}$ and $D_{max}$ were calculated and listed in Table 2. All degraders achieved 84-88% maximal degradation and no "hook effects" was observed at ≤1 µM. The new degraders had single-digit nanomolar $DC_{50}$, which was about 3 to 5 fold of improvement from 9.12 nM of degrader 1. Among these degraders, 12d showed excellent potency with a $DC_{50}$ at 1.64 nM. As discussed above, most PROTACs were designed to avoid degrading other proteins except the targeted POIs. However, in these studies, it was hypothesized that HDAC6 degraders with IKZF degradation will have enhanced anti-proliferation effect MM1S cells. Because compound 12d showed promising IKZF degradation activity (FIG. 10A), its activity and mechanism of action were further characterized.

Figure 12B:
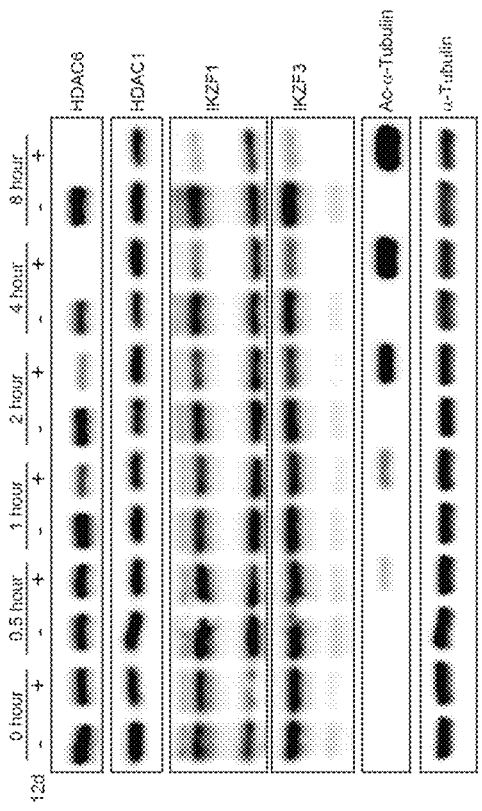
FIGS. 12A, 12B, and 12C are a series of western blots showing that degrader 12d selectively promotes HDAC6 degradation in MM1S cells.
Figure 12C:
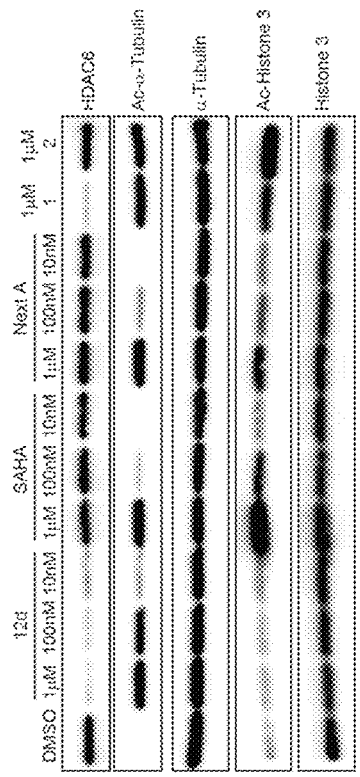
Figure 12A:
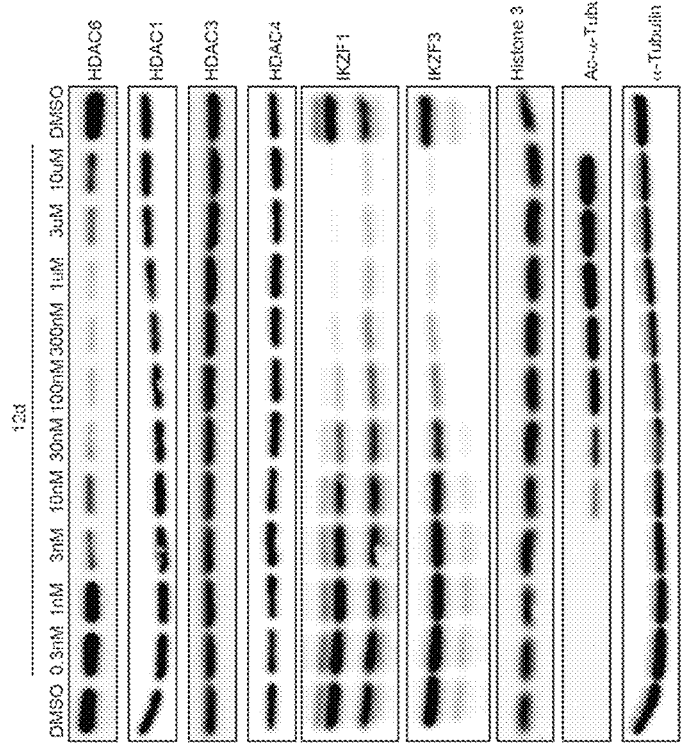

To evaluate the activity and selectivity of 12d, a full dose response experiment was performed with compound concentrations ranging from 0.3 nM to 10 µM in MM1S cells (FIG. 12A) for several HDACs, IKZFs, and Ac-tubulin. The result indicated that only the expression of HDAC6 was affected among the HDACs examined. Degrader 12d reduced HDAC6 protein content at as low as 3 nM and achieved maximal effects around 30 nM. The "Hook effect" was observed at 3 µM or above due to formation of binary complexes. See Douglass et al. 2013, supra. The degradation of IKZFs started from 30 nM and was dose-dependent. It is interesting to see the more efficient degradation of HDAC6, which requires the formation of ternary complex, than that of IKZFs, which only requires the formation of binary complex. In addition to the distinct mechanism, the different turnover rates of HDAC6 and IKZFs may also contribute to the observed results. The acetylated tubulin level was also dose-dependent. At higher concentrations (3 µM and 10 µM), tubulin acetylation was not decreased in response to recovered HDAC6 expression by "hook effect". The elevated tubulin acetylation at higher concentrations was likely due to the combination of HDAC6 degradation and HDAC6 inhibition.

To probe the efficiency of 12d, MM1S was treated with 100 nM 12d and the change of HDAC6 protein level was monitored by time. See FIG. 12B. The HDAC6 degradation started around 1 h and reached maximal degradation effect at 4 h. The degradation of IKZFs was only observed after 4 h. Meanwhile, HDAC1 was not affected and the acetylation of tubulin was accumulated by time. To study the re-synthesis rate of HDAC6 after degradation, "wash-out" experiments were performed (data not shown). Cells were treated with 100 nM 12d for 6 h and then washed with PBS to remove remaining degraders. HDAC6 expression was monitored for 48 h. HDAC6 was not fully recovered within 48 h, suggesting the slow turnover rate of HDAC6. Interestingly, IKZF3 was quickly recovered after 12 h, indicating the fast re-synthesis rate of IKZFs, which might be one of the reasons for the requirement of higher concentrations of compounds for the degradation of IKZF. Selected degraders were also tested in other cell lines and they are effective among all tested cancer cell lines.

To further examine the selectivity of the new generation of HDAC6 degraders, compound 12d was compared to SAHA, Next-A, degrader 1 and pan-inhibitor 2 for change of acetylated a-tubulin and acetylated histone H3. See FIG. 12C. Compound 12d increased the acetylated tubulin at 100 nM while SAHA and Next-A didn't, indicating that the elevated acetylated tubulin was primarily due to HDAC6 degradation rather than the inhibition by "warhead" Next-A. No increase of acetylated histone H3 was observed by the treatment 12d, which is in sharp contrast to the strong acetylated histone H3 signal induced by SAHA, suggesting high selectivity of the degrader. Comparing to the previously developed degrader 1, compound 12d also showed significantly improved selectivity for increasing the level of acetylated tubulin over acetylated histone H3, indicating the advantage of replacing a pan-HDAC inhibitor by HDAC6 selective inhibitor as the ligand of HDAC6 for PROTACs.

Figures 13A, 13B:
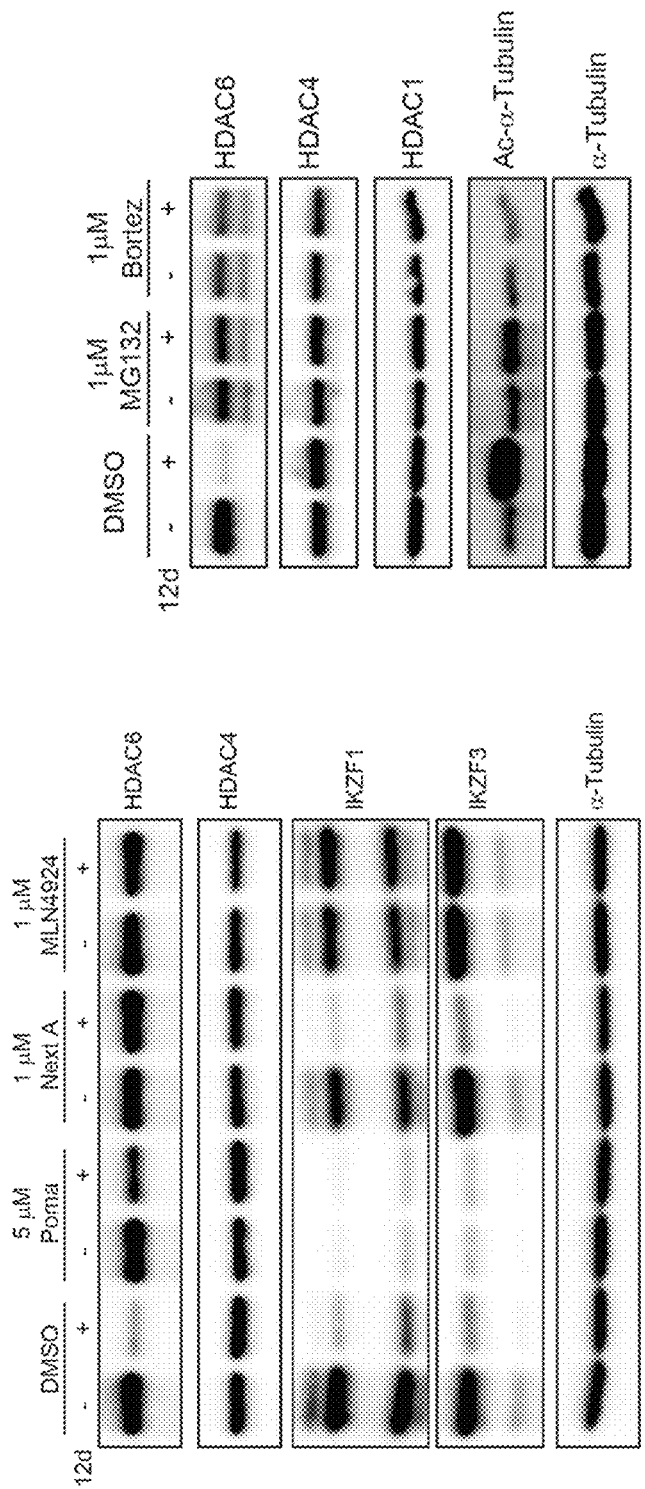
FIGS. 13A and 13B are western blot analysis of MM1S cells with pre-treatment of E3 ligase ligand pomalidomide, HDAC6 inhibitor Next-A or NAE inhibitor MLN 4924 (FIG. 13A) or pre-treatment of proteasome inhibitor MG132 or Bortezomib (FIG. 13B) or vehicle (DMSO) for 1 h and it is followed by the treatment of 100 nM 2d or vehicle (DMSO) for 6 h.

To support the involvement of ubiquitination-proteasome system for the decrease of HDAC6 protein level, the degrader was co-treated with binding competitors or pathway blockers. The co-treatment of degrader with pomalidomide or Next-A recovered HDAC6 level while the degradation of IKZFs was preserved. See FIG. 13A, indicating that the binding of the degrader to both HDAC6 and CRBN E3 ligase are required for induced protein degradation. Moreover, it also confirmed the role of the pomalidomide moiety in modulating IKZFs. Inhibiting neddylation by NAE inhibitor MLN4924 resulted in abolishing the degradation of both HDAC6 and IKZFs (FIG. 13A). Additionally, proteasome inhibitor MG132 and Bortezomib were used to block the down-stream proteasome degradation. See FIG. 13B. Under the co-treatment of both inhibitors, no degradation of HDAC6 or of other HDACs was observed. Acetylated tubulin level was suppressed as well. This confirms that HDAC6 degradation is responsible for the acetylation of its substrates rather than inhibition by the "warhead" moiety. To exclude the possible transcriptional impact by degraders, qRT-PCR was used to examine the mRNA level of HDAC6 and related genes (data not shown). Little to no effects on HDACs and IKZFs was seen after 6 h treatment of degrader 12d. This is consistent with the hypothesis that the cellular knockdown of HDAC6 is due to direct protein degradation, not by transcriptional downregulation.

Scheme 2. <sup>a</sup>Synthetic Route to Deactivated Degraders 11 and 13

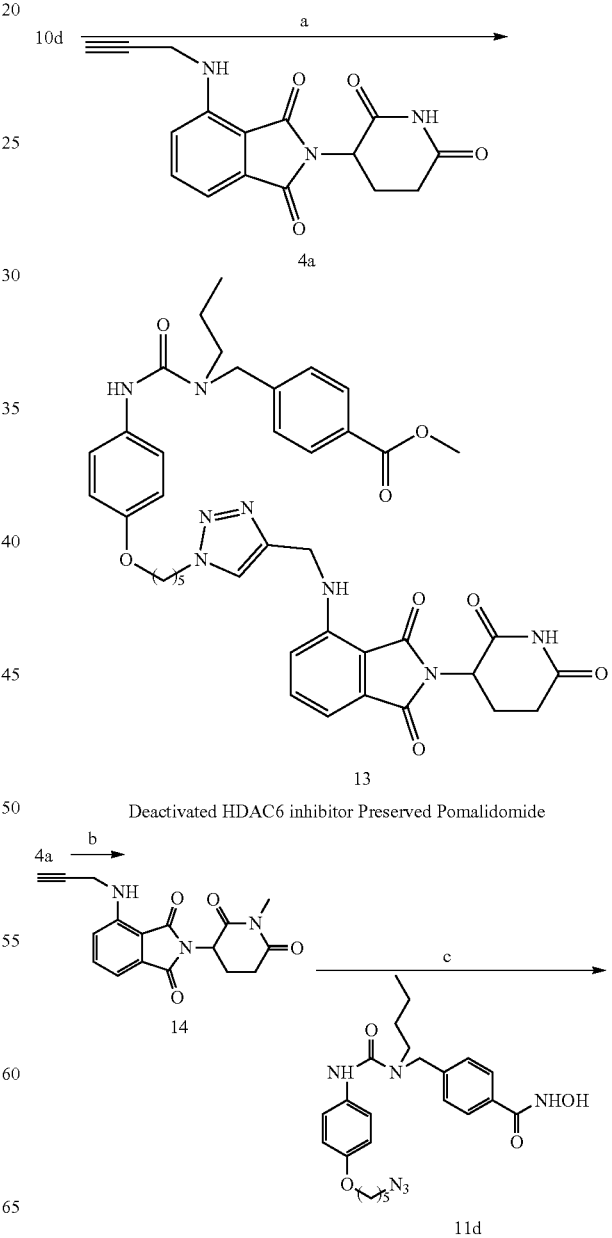

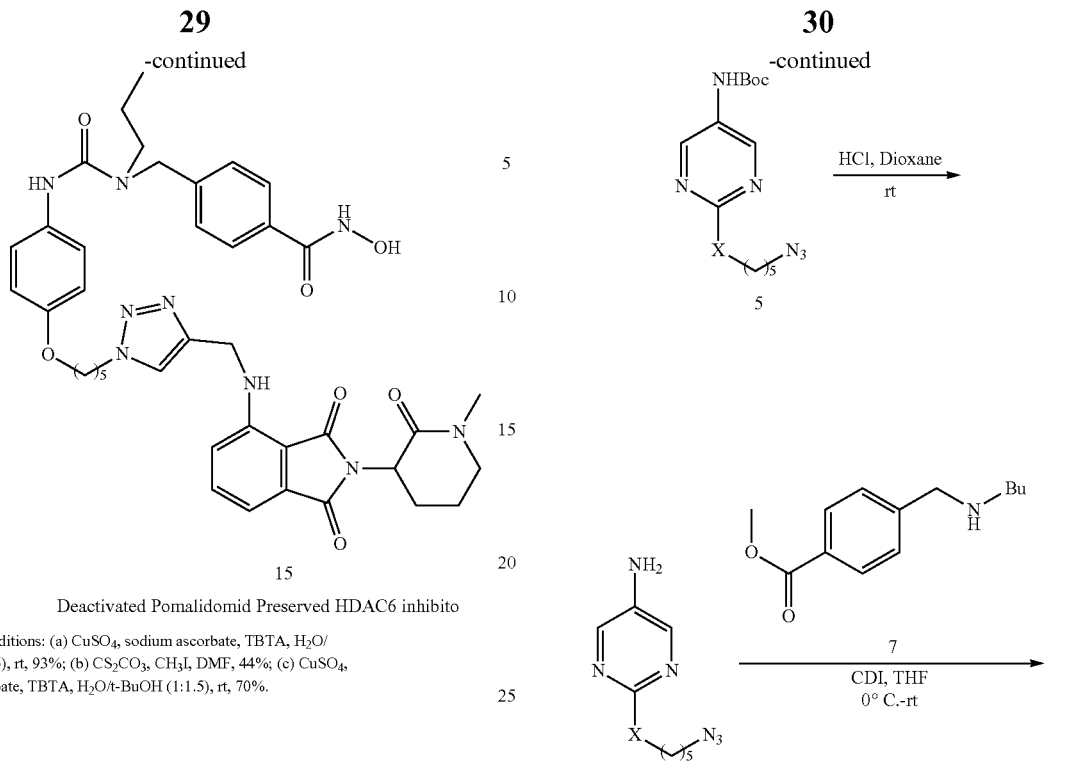
15
Deactivated Pomalidomid Preserved HDAC6 inhibito
<sup>a</sup>Reaction conditions: (a) CuSO₄, sodium ascorbate, TBTA, H₂O/t-BuOH (1:1.5), rt, 93%; (b) CS₂CO₃, CH₃I, DMF, 44%; (c) CuSO₄, sodium ascorbate, TBTA, H₂O/t-BuOH (1:1.5), rt, 70%.
Scheme 3. Synthetic Route and General Procedure to Make Compounds 11', 12', and 13'
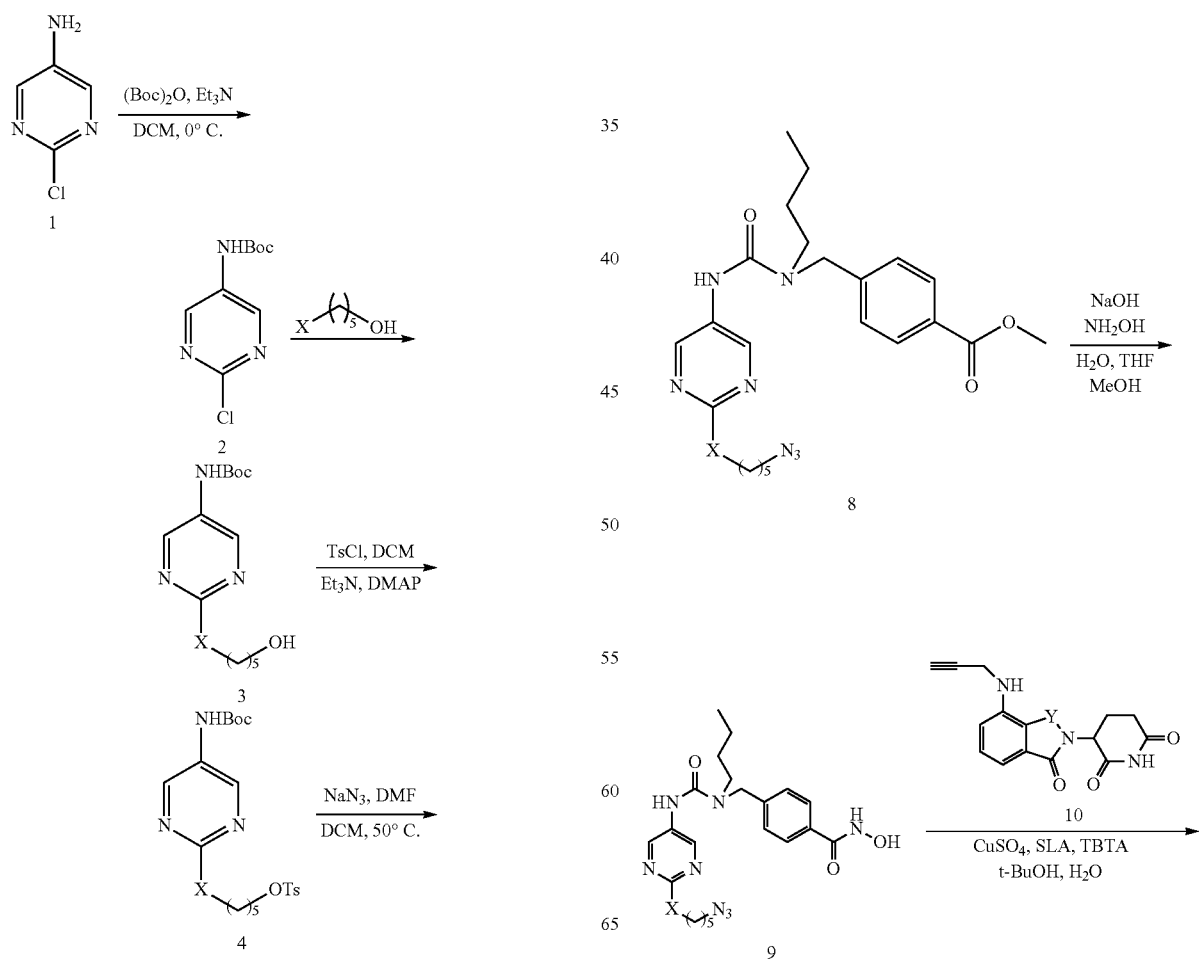

-continued

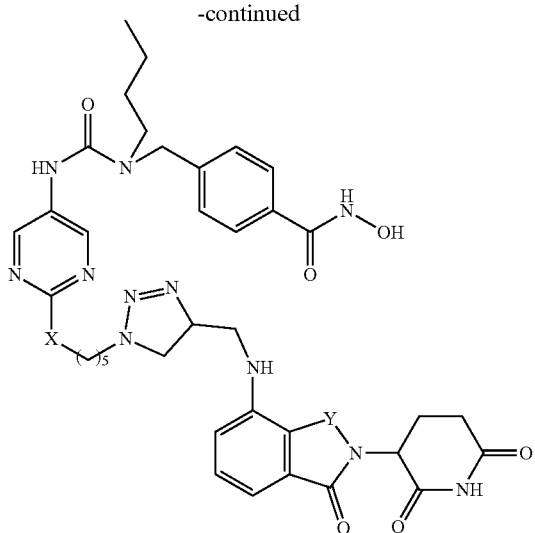

11': X = O, Y = CO, n = 5
12': X = N, Y = CO, n = 5
13': X = n, Y = CH₂, n = 5
("n" may be 1 to 12)

A mixture of 1 (500 mg, 3.85 mmol) and di-tert-butyl dicarbonate (0.88 ml, 4.23 mmol), Et₃N (1.1 ml, 7.7 mmol), DMAP (47 mg, 0.39 mmol), in DMF/DCM (2:5, 7 ml total) was stirred at room temperature for overnight. The reaction mixture was then evaporated directly. The residue was purified by silica gel flash column chromatography (eluted with 20% ethyl acetate in hexane) to afford 2 (614 mg, 70%).

For X=O, A mixture of compound 2 (500 mg, 2.17 mmol) and potassium carbonate (901 mg, 6.52 mmol) in 1,5-Pentanediol (3 mL) was stirred at 80° C. overnight. The mixture was cooled to room temperature and poured into water (10 mL), then extracted with ethyl acetate (10 mL×3). The combined organic phases were washed with brine (20 mL), dried over anhydrous sodium sulfate, and concentrated under reduced pressure. The residue was purified by silica gel flash column chromatography (eluted with 5% methanol in dichloromethane) to afford product 3 (597 mg, 93%).

For X=N, A mixture of compound 2 (500 mg, 2.17 mmol), 5-Amino-1-pentanol (673 mg, 6.5 mmol) and Et₃N (0.9 ml, 6.5 mmol) in ethanol (4 mL) was stirred at 110° C. overnight. The mixture was cooled to room temperature and poured into water (10 mL), then extracted with ethyl acetate (10 mL×3). The combined organic phases were washed with brine (20 mL), dried over anhydrous sodium sulfate, and concentrated under reduced pressure. The residue was purified by silica gel flash column chromatography (eluted with 5% methanol in dichloromethane) to afford product 3 (565 mg, 87%).

A mixture of compound 3, p-toluenesulfonyl chloride (1.1 eq), triethylamine (1.1 eq) and 4-(Dimethylamino) pyridine (0.2 eq) in dichloromethane was stirred at room temperature for overnight. Quenched with water (10 mL) and extracted with dichloromethane (10 mL×3). The combined organic phases were washed with water (10 mL) and brine (10 mL), dried over anhydrous sodium sulfate, and concentrated under reduced pressure. The residue was purified by silica gel flash column chromatography (eluted with 50% ethyl acetate in hexane) to afford 4.

A suspension of compound 4 and sodium azide (5 eq) in DMF (5 mL) was stirred at 50° C. overnight. Quenched with water and extracted with Dichloromethane. The combined organic phase was washed with water and brine, dried over anhydrous sodium sulfate and concentrated in vacuo. The residue was purified by silica gel column chromatograph (eluted with 20% ethyl acetate in hexane) to afford 5.

To a solution of azide 5 in DCM (45 ml) was added Hydrogen chloride solution in dioxane (4M) dropwise at 0° C. The resulting mixture was stirred at rt for overnight. Upon completion as evidenced by TLC, the reaction was quenched by NaHCO₃ aq., then extracted with ethyl acetate (10 mL×3). The combined organic layers were washed with brine (20 mL), dried over anhydrous sodium sulfate, and concentrated under reduced pressure. The residue was purified by silica gel flash column chromatography (eluted with 5% methanol in dichloromethane) to afford compound 6.

A solution of 6 (1 eq) in THF (3 mL) was added the Carbonyldiimidazole (CDI: 1.2 eq) and 7 (1.1 eq) at 0° C. under an atmosphere of Ar, and the resulting solution was stirred for overnight. The reaction was quenched with saturated bicarbonate (10 mL) and extracted with DCM (3×10 mL). The combined organics were washed with brine (15 mL), dried over sodium sulfate, concentrated in vacuo, and purified via silica gel chromatography, affording the urea ester 8.

Solid NaOH (8eq) was dissolved in an aqueous solution (50 wt %, 1 mL) at 0° C. Then a solution of 8 (1 eq) in THF/MeOH (1:1, 3 mL total) was added dropwise where the biphasic solution became homogeneous upon compete addition. The resulting solution was stirred 1 h at room temperature. The reaction was quenched with AcOH (9.6 eq) and concentrated in vacuo, and the crude product was purified silica gel chromatography, affording 9.

A mixture of 9 (1 eq) and compound 10 (1eq), tris[(1-benzyl-1H-1,2,3-triazol-4-yl)methyl]amine (0.12 eq), CuSO₄ (0.2 eq), sodium ascorbate (1.2 eq) in t-BuOH:H₂O (1.5:1) (2.5 mL) was stirred at room temperature for 16 h. The reaction mixture was evaporated directly. The residue was purified by silica gel flash column chromatography (eluted with 10% methanol in dichloromethane) to afford 11', 12', and 13'.

11': $^1$H NMR (400 MHz, DMSO): δ 0.67-0.91 (m, 3H), 1.04-1.36 (m, 5H), 1.39-1.53 (m, 1H), 1.58-1.94 (m, 4H), 1.96-2.16 (m, 1H), 2.53-2.70 (m, 2H), 2.74-3.03 (m, 1H), 3.20-3.33 (m, 2H), 4.05-4.23 (m, 2H), 4.28-4.46 (m, 2H), 4.51-4.86 (m, 3H), 4.96-5.23 (m, 1H), 6.91-7.22 (m, 3H), 7.24-7.41 (m, 1H), 7.49-7.63 (m, 1H), 7.93-8.23 (m, 1H), 8.39-8.81 (m, 3H), 9.05 (br, 1H), 11.1 (br, 2H). $^{13}$C NMR (100 MHz, DMSO) δ 172.8, 170.1, 168.8, 167.3, 160.3, 155.2, 151.6, 145.8, 144.4, 136.1, 132.1, 130.0, 128.7, 127.1, 122.8, 117.6, 110.9, 109.7, 66.6, 49.2, 46.1, 37.7, 31.0, 29.8, 29.4, 27.7, 22.5, 22.1, 19.4, 13.7.

12': $^1$H NMR (400 MHz, DMSO): δ 0.82 (t, J=7.4 Hz, 3H), 1.14-1.25 (m, 5H), 1.37-1.58 (m, 4H), 1.67-1.84 (m, 2H), 1.92-2.05 (m, 1H), 2.52-2.62 (m, 2H), 2.74-2.95 (m, 1H), 3.07-3.24 (m, 4H), 4.20-4.34 (m, 2H), 4.47-4.65 (m, 3H), 4.93-5.10 (m, 1H), 6.72-6.93 (m, 1H), 6.97-7.06 (m, 2H), 7.09-7.17 (m, 1H), 7.20-7.35 (m, 2H), 7.48-7.59 (m, 1H), 7.62-7.74 (m, 1H), 7.98 (s, 1H), 8.07-8.25 (m, 2H), 8.97 (br, 1H), 10.92-11.33 (m, 2H). $^{13}$C NMR (100 MHz, DMSO) δ 172.8, 170.1, 168.8, 167.3, 159.2, 155.8, 152.5, 145.8, 144.4, 136.1, 132.1, 128.7, 127.7, 127.0, 122.7, 117.6, 110.9, 109.7, 54.9, 49.3, 46.0, 40.6, 37.7, 31.0, 29.5, 28.3, 23.3, 22.1, 19.4, 13.8.

13': $^1$H NMR (400 MHz, DMSO): δ 0.83-0.88 (m, 5H), 0.94-0.99 (m, 1H), 1.40-1.58 (m, 6H), 1.77-1.82 (m, 1H), 1.96-2.09 (m, 1H), 2.14-2.21 (m, 1H), 2.26-2.35 (m, 1H), 2.58-2.68 (m, 1H), 2.84-2.99 (m, 1H), 3.16-3.26 (m, 4H), 4.16-4.25 (m, 1H), 4.27-4.34 (m, 2H), 4.37-4.46 (m, 2H), 4.52-4.64 (m, 2H), 5.05-5.16 (m, 1H), 6.10-6.27 (m, 1H), 6.77-6.84 (m, 1H), 6.84-6.91 (m, 1H), 6.92-6.99 (m, 1H), 7.21-7.28 (m, 1H), 7.31 (d, J=8.0 Hz, 2H), 7.72 (d, J=8.0 Hz, 2H), 7.96 (s, 1H), 8.16-8.25 (m, 2H), 9.01 (br, 1H), 10.91-11.37 (m, 2H). $^{13}$C NMR (100 MHz, DMSO) δ 172.9, 171.2, 168.7, 159.2, 155.8, 152.5, 145.2, 143.1, 132.1, 129.1, 127.0, 124.6, 122.7, 110.6, 99.5, 51.5, 49.2, 46.0, 45.7, 42.6, 38.4, 29.9, 29.0, 28.7, 28.5, 28.3, 24.5, 23.4, 19.5, 13.8.

The HDAC6 degrader 12d has three functions: inhibition of HDAC6 by the Next-A motif, degradation of IKZFs by the pomalidomide moiety, and the degradation of HDAC6 through the formation of the ternary complex. The formation two functions can be achieved by the combination of HDAC6 selective inhibitor and pomalidomide. The third function is unique for HDAC6 degraders. Because HDAC6-selective inhibitors showed synergy with pomalidomide and its related analogues for the treatment of multiple myeloma in animal models and human clinical trials (see, for example, Hideshima 2015, supra), it was hypothesized that HDAC6 degrader 12d would have enhanced anti-myeloma activity over the combination of HDAC6 selective inhibitor and pomalidomide.

To rule out the potential cell-permeability issue, compounds 13 and 15 were synthesized, which have similar molecular weight and size comparing to 12d, for better comparison. The binding of 13 to HDAC6 was blocked by replacing the hydroxamic acid with a methyl ester. The binding of 15 to CRBN was also blocked by attaching a methyl group to the key imide NH in 15. Compounds 13 and 15 were synthesized according to the routes shown in Scheme 2. Compound 13 was synthesized using the procedure described for the synthesis of compounds 12a-s with ester 10d and alkyne 4a as the starting materials. Esterification of hydroxamic acid on Next-A moiety was expected to prevent binding to zinc co-factor of HDAC6. N-methylation of the glutarimide ring of the pomalidomide moiety in 4a yielded compound 14, which was converted to product 15 using click reaction. The N-methylated pomalidomide moiety has been frequently used as the negative control for pomalidomide-based PROTACs Lu et al. 2015, supra. Western blot analysis proved that both compounds 13 and 15 are inactive in MM1S (data not shown). Compound 13 induced limited HDAC6 degradation which might due to hydrolysis of carboxylic ester to carboxylic acid, which is a very weak ligand for zinc.

Single treatment or co-treatment was performed as combined therapy (1 μM) for 72 hours in MM1S cells. See FIG. 14A. Next-A had minor effects on cell growth while 15 was totally inactive. Pomalidomide, 13 and degrader 1 shared similar antiproliferation effects at this concentration. There was no statistically significant synergy of dual treatment seen with 13+15 (1:1) or dual treatment with pomalidomide+Next-A (1:1) comparing with single treatment of 13 or pomalidomide (P>0.05). The dual treatment of pomalidomide+Next-A (1:1) is slightly more potent than that of 13+15 (1:1). However, the single treatment of 12d improved about 19% (P=0.0017) and 11% (P=0.0213) growth inhibition comparing with the combination sets of 13+15 (1:1) and pomalidomide+Next-A (1:1), respectively. To further confirm the observed enhancement, the anti-proliferation in response to 12d was studied from 0.3 nM to 3 μM. See FIG. 14B. This single treatment was compared with dual treatment of 13 and 15 to rule out the potential complication derived from cell permeability issue. The resulting $IC_{50}$ and maximal inhibition was listed in Table 3. Degrader 12d lowered the bottom line (minimal proliferation) of curve over 20% although its $IC_{50}$ was decreased consequentially. The combination of 13 and 15 failed to work synergistically indicated the HDAC6 degradation, other than inhibition, was crucial to the enhanced antiproliferation by degrader 12d. Hence, it was concluded that the HDAC6 degradation and IKZF degradation had synergistic effects at higher concentration (>300 nM) of the degrader. For 48 h treatment of 12d in MM1S, the cleavages of Caspase-3 and PARP were dose-dependent (data not shown), suggesting that the synergy was derived from degrader-promoted cell apoptosis.

TABLE 3

| IC$_{50}$ of Antiproliferation in MM1S | | |
|---|---|---|
| | IC$_{50}$ (nM)$^a$ | Maximal Inhibition (%)$^b$ |
| 12d | 74.92 ± 11.35 | 63.15 ± 1.82 |
| 13 + 15 (1:1) | 23.50 ± 6.26 | 42.57 ± 1.88 |
| 13 | 17.72 ± 2.84 | 43.96 ± 1.16 |

$^a$The concentration at which half-maximal growth inhibition was achieved.
$^b$The maximum percentage of growth inhibition.
$^{a,b}$Values with ± SD obtained from nonlinear fitted data in FIG. 14B.

Figure 7:
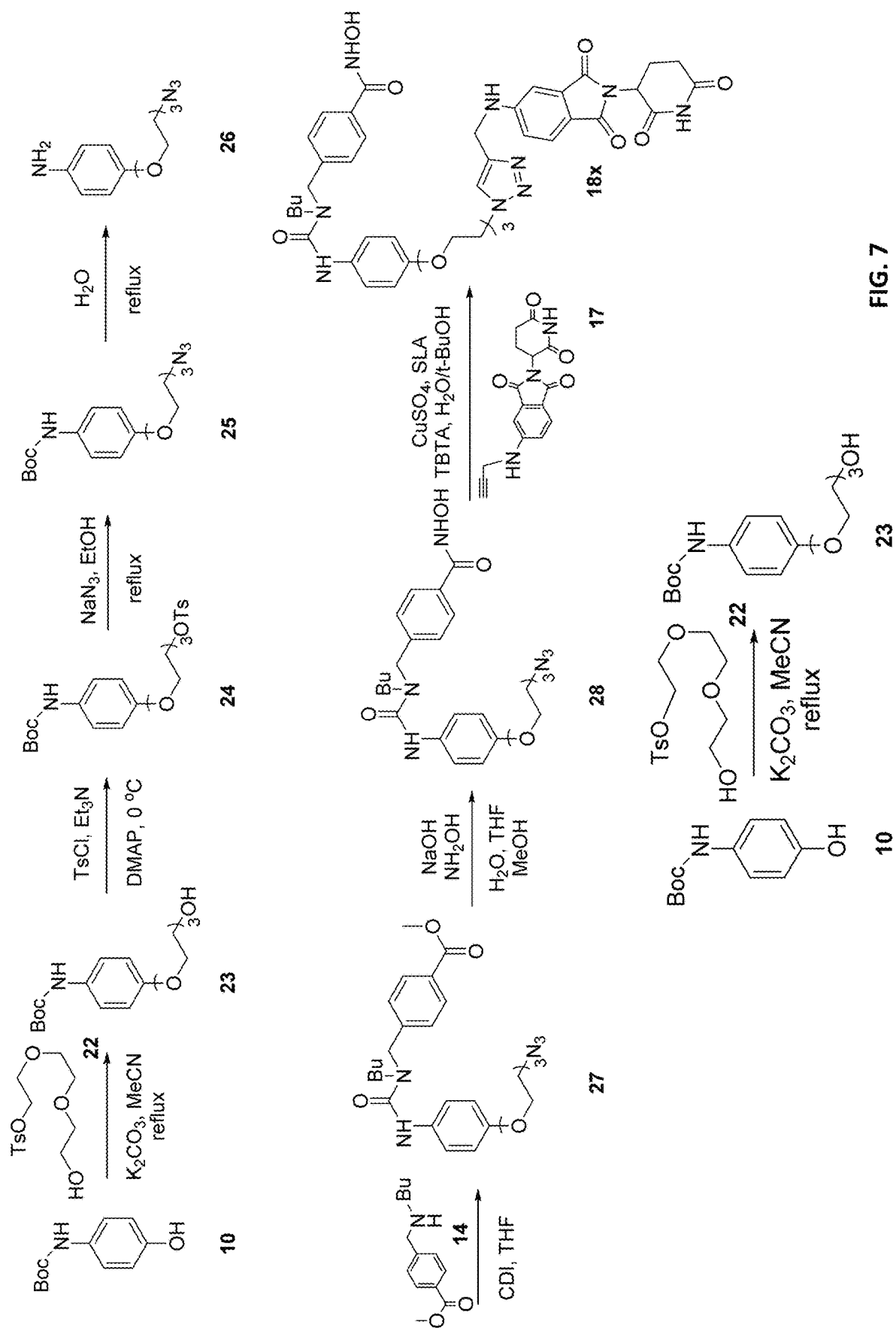
FIG. 7: General procedure for synthesis of compound 18x.

General Procedure for Syntheses of Compounds 18a-e:

Referring to FIG. 7 for the structures, compound 10 was prepared in one step following a published method (*J. Med. Chem.* 2012, 55, 9312-9330):

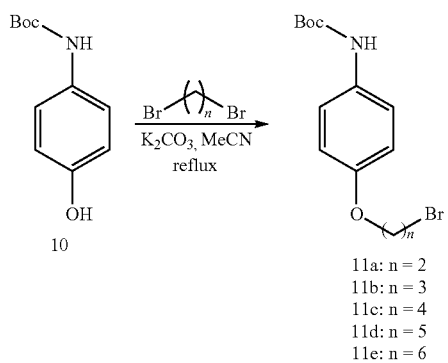

11a: n = 2
11b: n = 3
11c: n = 4
11d: n = 5
11e: n = 6

A mixture of compound 10 (500 mg, 2.4 mmol), 1,2-dibromoethane (0.82 mL, 9.6 mmol) and potassium carbonate (1.3 g, 9.6 mmol) in acetonitrile (5 mL) was stirred at 90° C. overnight. The mixture was cooled to room temperature and poured into water (2 mL), then extracted with ethyl acetate (10 mL×3). The combined organic phases were washed with brine (20 mL), dried over anhydrous sodium sulfate, and concentrated under reduced pressure. The residue was purified by silica gel flash column chromatography (eluted with 5% ethyl acetate in hexane) to afford compound 11a (482 mg, 64%) as white solid.

Following the procedure, 11b-e with different bromide chains were obtained as white solid (45-70% yield).

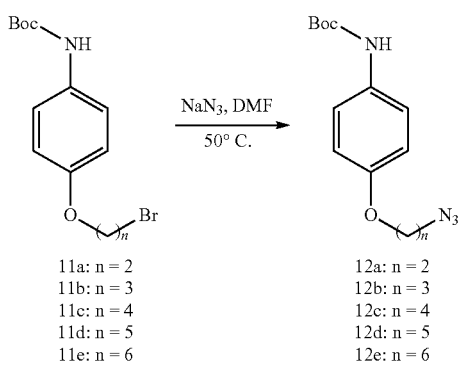

11a: n = 2      12a: n = 2
11b: n = 3      12b: n = 3
11c: n = 4      12c: n = 4
11d: n = 5      12d: n = 5
11e: n = 6      12e: n = 6

A suspension of compound 11a (300 mg, 0.95 mmol) and sodium azide (308 mg, 4.7 mmol) in DMF (5 mL) was stirred at 50° C. for 4 h. Then EtOAc and water were added. The organic layer was separated and washed once with water. The resulting aqueous layer was extracted once with EtOAc. The combined organic layer was dried over with Na$_2$SO$_4$ and concentrated in vacuo. The residue was purified by silica gel chromatograph to give the product 12a (224 mg, 85%) as white solid.

Following the procedure, 12b-e with different azide chains were obtained as white solid (66-90% yield).

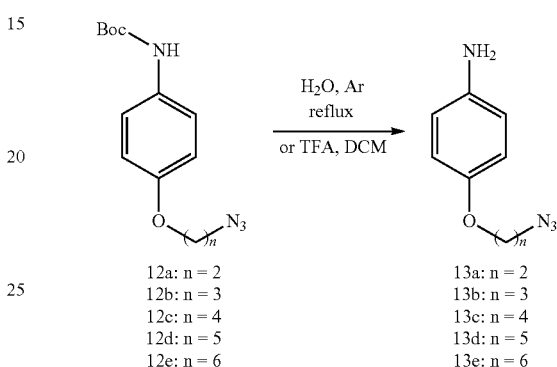

12a: n = 2      13a: n = 2
12b: n = 3      13b: n = 3
12c: n = 4      13c: n = 4
12d: n = 5      13d: n = 5
12e: n = 6      13e: n = 6

Compound 13a-c were prepared according to the method described in previous literature (Chem. Commun., 2009, 5144-5146).

In a 250 mL round bottle flask filled with 100 mL of water, 12a (224 mg, 0.8 mmol) was added. Then the flask topped with a condenser was dipped in a 110° C. oil bath. Thin-layer chromatography was used to monitor the progress of the reaction. The reaction mixture was cooled down after 12 h and was extracted with ethyl acetate (40 mL×3). The extract was washed with brine, dried over anhydrous Na$_2$SO$_4$, and then concentrated in vacuo. The residue was purified by column chromatography on silica gel with ethyl acetate/petroleum ether (1:1, v/v) to afford the free amine 13a as a white solid (140 mg, 97%).

Following the procedure, 13b-c with different bromide chains were obtained as white solid (>95%).

For the Syntheses of 13d and 13e:

To a solution of azide (12d-e) in DCM (45 ml) was added TFA (30 eq) dropwise at 0° C. The resulting mixture was stirred at 0° C. for 4 h. Upon completion as evidenced by TLC, the reaction was quenched by NaHCO$_3$aq., then extracted with ethyl acetate (10 mL×3). The combined organic layers were washed with brine (20 mL), dried over anhydrous sodium sulfate, and concentrated under reduced pressure. The residue was purified by silica gel flash column chromatography (eluted with 20% ethyl acetate in hexane) to afford compound 13d-e (94-96%) as white solid.

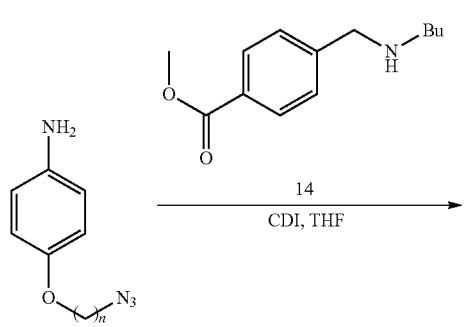

13a: n = 2
13b: n = 3
13c: n = 4
13d: n = 5
13e: n = 6

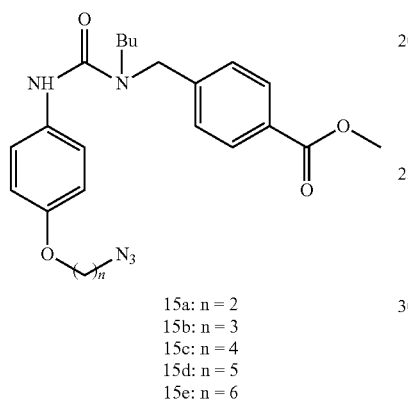

15a: n = 2
15b: n = 3
15c: n = 4
15d: n = 5
15e: n = 6

Compound 14 was prepared step following a published method (J. Med. Chem. 2012, 55, 9891-9899).

A solution of 13a (140 mg, 0.78 mmol) in THF (2 mL) was added the Carbonyldiimidazole (CDI: 153 mg, 0.94 mmol) at room temperature under an atmosphere of Ar, and the resulting solution was stirred for 2 h. Then 14 (173 mg, 0.78 mmol) in THF (2 ml) was added dropwise to the reaction mixture and the resulting mixture was stirred overnight. The reaction was quenched with saturated bicarbonate (10 mL) and extracted with DCM (3×10 mL). The combined organics were washed with brine (15 mL), dried over sodium sulfate, concentrated in vacuo, and purified via silica gel chromatography, affording the urea ester 15a as a brown oil (253 mg, 76%).

Following the procedure, 15b-e with different azide chains were obtained as brown oil (13-88% yield).

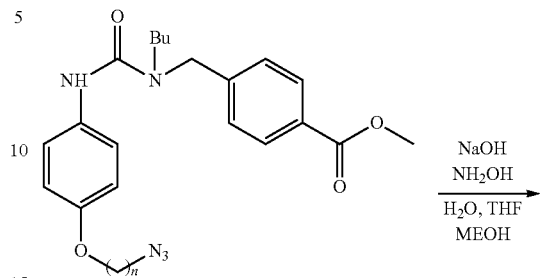

15a: n = 2
15b: n = 3
15c: n = 4
15d: n = 5
15e: n = 6

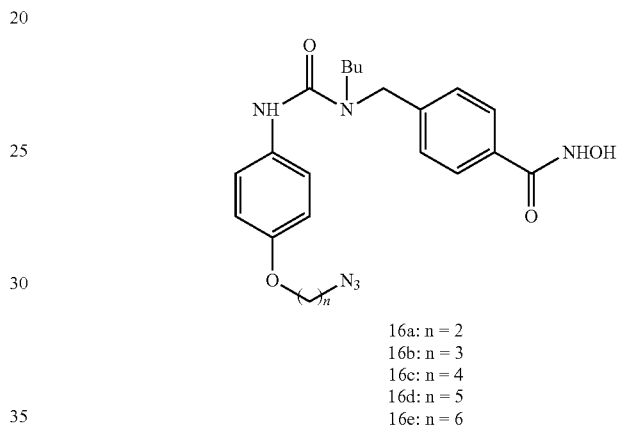

16a: n = 2
16b: n = 3
16c: n = 4
16d: n = 5
16e: n = 6

Solid NaOH (188 mg, 4.7 mmol) was dissolved in an aqueous solution (50 wt %, 1 mL) at 0° C. Then a solution of 15a (250 mg, 0.59 mmol) in THF/MeOH (1:1, 3 mL total) was added dropwise where the biphasic solution became homogeneous upon compete addition. The resulting solution was stirred 1 h at room temperature. The reaction was quenched with AcOH (0.35 mL, 5.64 mmol) and concentrated in vacuo, and the crude product was purified silica gel chromatography, affording 16a (231 mg, 92%) as yellow solid.

Following the procedure, 16b-e with different azide chains were obtained as yellow solid (87-92% yield).

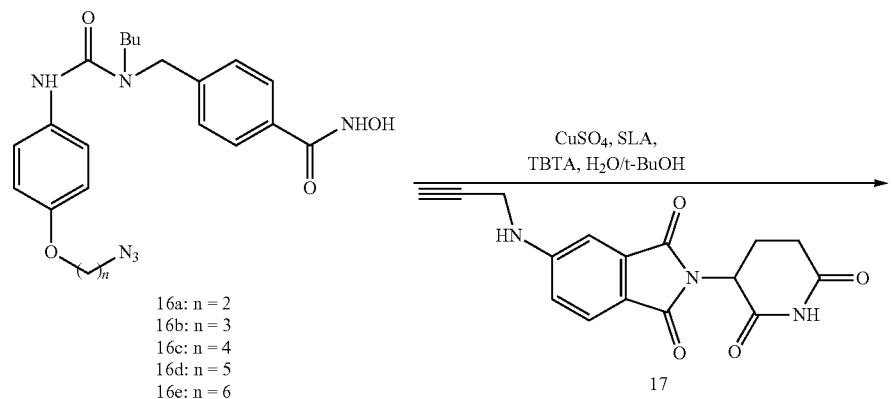

16a: n = 2
16b: n = 3
16c: n = 4
16d: n = 5
16e: n = 6

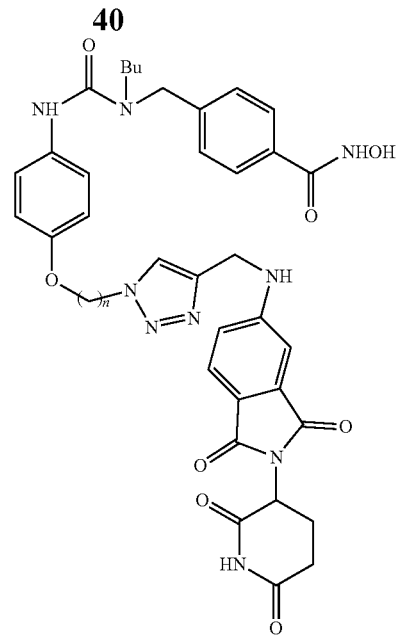

18a, n = 2
18b, n = 3
18c, n = 4
18d, n = 5
18e, n = 6

Compound 17 was prepared according to the method described in the previous literature (Yang et al. 2018, supra).

17: $^1$H NMR (400 MHz, DMSO): δ 1.99-2.02 (m, 1H), 2.53-2.60 (m, 1H), 2.83-2.93 (m, 1H), 3.19 (s, 1H), 4.07 (br, 1H), 5.03-5.06 (m, 1H), 6.94 (d, J=8.4 Hz, 1H), 7.04 (br, 1H), 7.41-7.44 (m, 1H), 7.62 (d, J=8.4, 1H), 11.07 (br, 1H). $^{13}$C NMR (100 MHz, DMSO): δ 173.27, 170.59, 168.06, 167.62, 153.92, 134.42, 125.39, 117.87, 81.17, 74.33, 49.16, 32.24, 31.46, 22.67.

A mixture of 16a (50 mg, 0.12 mmol) and compound 17 (38 mg, 0.12 mmol), tris[(1-benzyl-1H-1,2,3-triazol-4-yl)methyl]amine (8 mg, 0.014 mmol), CuSO$_4$ (2 mg, 0.1 mmol), sodium ascorbate (29 mg, 0.144 mmol) in t-BuOH:H$_2$O (1:1) (2 mL) was stirred at room temperature for 16 h. The reaction mixture was then quenched with water (5 mL), and extracted with dichloromethane (10 mL×3). The combined organic phases were washed brine (50 mL), dried over anhydrous sodium sulfate, and concentrated under reduced pressure. The residue was purified by silica gel flash column chromatography (eluted with 30% methanol in dichloromethane) to afford the 18a (37 mg, 42%) as yellow oil.

18a: $^1$H NMR (400 MHz, DMSO): δ 0.85 (t, J=6.8 Hz, 3H), 1.12-1.33 (m, 2H), 1.39-1.53 (m, 2H), 1.96-2.07 (m, 1H), 2.54-2.64 (m, 2H), 2.80-2.95 (m, 1H), 3.18-3.27 (m, 2H), 4.32 (br, 2H), 4.49 (br, 2H), 4.59 (br, 2H), 4.72 (br, 2H), 4.99-5.08 (m, 1H), 6.78 (d, J=8 Hz, 2H), 6.96 (d, J=7.6 Hz, 1H), 7.08 (br, 1H), 7.22-7.41 (m, 4H), 7.58 (d, J=8 Hz, 2H), 7.72 (d, J=7.2 Hz, 2H), 8.09 (s, 1H), 8.24, (s, 1H), 9.01 (br, 1H), 11.01-11.25 (m, 2H). $^{13}$C NMR (100 MHz, DMSO): δ 172.82, 170.17, 167.64, 167.15, 164.10, 155.43, 154.02, 153.03, 144.29, 142.43, 134.07, 131.39, 126.99, 125.00, 123.55, 121.94, 116.69, 114.34, 66.45, 49.09, 49.00, 48.67, 46.07, 37.99, 31.01, 29.99, 22.24, 19.47, 13.82.

Following the procedure, 18b-e were obtained as yellow solid (35-49% yield). 18b: $^1$H NMR (400 MHz, DMSO): δ 0.85 (br, 3H), 1.24 (br, 2H), 1.39-1.59 (m, 2H), 1.98 (br, 1H), 2.23 (br, 2H), 2.50-2.66 (m, 2H), 2.78-2.96 (m, 1H), 3.19-3.35 (m, 2H), 3.90 (br, 2H), 4.33-4.69 (m, 6H), 4.92-5.13 (m, 1H), 6.79 (br, 2H), 6.95 (br, 1H), 7.07 (br, 1H), 7.33 (br, 4H), 7.58 (br, 2H), 7.73 (br, 2H), 8.08 (s, 1H), 8.25 (s, 1H), 9.00 (br, 1H), 10.86-11.30 (m, 2H). $^{13}$C NMR (100 MHz, DMSO): δ 172.81, 170.16, 167.64, 167.15, 155.47, 154.00, 153.58, 144.27, 142.46, 134.06, 133.68, 131.37, 128.73, 127.73, 127.00, 125.00, 123.11, 122.02, 116.67, 114.17, 64.61, 63.09, 49.02, 48.66, 46.57, 46.07, 38.07, 31.00, 29.99, 29.62, 22.23, 19.46, 13.81.

18c: $^1$H NMR (400 MHz, DMSO): δ 0.81 (t, J=7.2 Hz, 3H), 1.15-1.27 (m, 3H), 1.37-1.48 (m, 3H), 1.54-1.67 (m, 2H), 1.84-1.93 (m, 2H), 2.40-2.48 (m, 2H), 2.76-2.93 (m, 1H), 3.21-3.30 (m, 2H), 3.82-3.91 (m, 2H), 4.31-4.39 (m, 2H), 4.40-4.49 (m, 2H), 4.57 (br, 2H), 4.93-5.09 (m, 1H), 6.75 (d, J=8.8 Hz, 2H), 6.93 (d, J=8 Hz, 1H), 7.04 (br, 1H), 7.26-7.32 (m, 5H), 7.53 (d, J=8.4 Hz, 1H), 7.61-7.67 (m, 1H), 7.70 (d, J=8 Hz, 2H), 8.03 (s, 1H), 8.26 (s, 1H), 11.03-11.36 (m, 2H). $^{13}$C NMR (100 MHz, DMSO): δ 172.84, 170.18, 167.66, 167.17, 155.53, 154.05, 153.78, 144.24, 142.48, 134.05, 133.54, 131.36, 128.74, 127.77, 127.03, 126.99, 125.00, 123.00, 122.06, 116.63, 114.09, 72.55, 66.90, 63.06, 54.96, 52.73, 49.09, 49.04, 48.67, 46.10, 31.02, 30.02, 26.66, 25.76, 22.26, 19.48, 14.11, 13.84.

18d: $^1$H NMR (400 MHz, DMSO): δ 0.82-0.88 (m, 3H), 1.14-1.23 (m, 2H), 1.31-1.40 (m, 2H), 1.43-1.51 (m, 2H), 1.62-1.74 (m, 2H), 1.79-1.91 (m, 2H), 1.92-2.04 (m, 1H), 2.52-2.61 (m, 2H), 2.76-2.96 (m, 1H), 3.28-3.38 (m, 2H), 3.78-3.92 (m, 2H), 4.35 (br, 2H), 4.47 (br, 2H), 4.59 (br, 2H), 4.96-5.09 (m, 1H), 6.75-6.81 (m, 2H), 6.91-6.98 (m, 1H), 7.02-7.13 (m, 2H), 7.21-7.44 (m, 5H), 7.49-7.61 (m, 2H), 7.66-7.76 (m, 2H), 8.04 (s, 1H), 8.22 (s, 1H), 8.99 (br, 1H), 8.99 (br, 1H), 10.94-11.36 (m, 2H). $^{13}$C NMR (100 MHz, DMSO): 172.80, 170.13, 167.62, 167.14, 164.09, 156.26, 155.48, 154.00, 153.88, 144.14, 142.47, 134.04, 133.37, 131.37, 128.73, 127.40, 126.99, 124.98, 122.91, 122.06, 116.65, 114.04, 113.86, 72.50, 69.82, 69.09, 67.31, 63.08, 49.25, 48.99, 46.05, 41.15, 38.08, 30.99, 29.99, 29.51, 28.12, 22.57, 22.22, 19.46, 13.81.

18e: 0.79-0.90 (m, 3H), 1.18-1.30 (m, 4H), 1.34-1.51 (m, 4H), 1.58-1.70 (m, 2H), 1.73-1.88 (m, 2H), 1.92-2.04 (m, 1H), 2.53-2.62 (m, 2H), 2.78-2.93 (m, 1H), 2.38-2.54 (m, 2H), 3.79-3.94 (m, 2H), 4.30-4.38 (m, 2H), 4.42-4.49 (m, 2H), 4.54-4.66 (m, 2H), 4.97-5.09 (m, 1H), 6.74-6.84 (m, 2H), 6.90-6.99 (m, 1H), 7.06 (br, 1H), 7.25-7.43 (m, 5H), 7.53-7.61 (m, 2H), 7.68-7.78 (m, 2H), 8.03 (s, 1H), 8.20 (s, 1H), 11.99-11.32 (m, 2H). $^{13}$C NMR (100 MHz, DMSO): δ 172.80, 170.14, 167.62, 167.14, 164.10, 155.48, 153.99, 153.95, 144.13, 142.47, 134.04, 133.33, 131.38, 128.74, 127.74, 126.99, 124.99, 122.89, 122.08, 116.66, 114.06, 67.40, 49.26, 48.99, 48.65, 46.06, 38.08, 30.99, 29.99, 29.68, 28.56, 25.60, 24.94, 22.23, 19.47, 13.82.

General Procedure for Syntheses of Compounds 20a-c:

δ 172.81, 170.16, 167.66, 167.14, 154.34, 134.22, 125.12, 116.08, 83.89, 71.64, 48.63, 41.31, 40.43, 30.99, 27.19, 22.24, 15.38.

Employing the same procedure for converting 16a-e to 18a-e, 20a-c can be obtained from 16a-c in 14-24% yield.

20a: $^{1}$H NMR (400 MHz, DMSO): δ 0.84 (t, J=7.2 Hz, 3H), 1.08-1.17 (m, 2H), 1.38-1.51 (m, 2H), 1.53-1.57 (m, 1H), 1.84-2.04 (m, 2H), 2.69-2.77 (m, 2H), 2.82-2.91 (m, 1H), 3.82-3.36 (m, 4H), 3.92-4.03 (m, 1H), 4.12-4.18 (m, 1H), 4.27-4.36 (m, 2H), 4.30-4.50 (m, 1H), 4.54-4.62 (m, 2H), 4.65-4.73 (m, 2H), 4.99-5.07 (m, 1H), 6.76-6.85 (m, 3H), 6.97 (br, 1H), 7.07 (br, 1H), 7.30 (d, J=7.6 Hz, 1H), 7.35 (d, J=7.6 Hz, 1H), 7.55 (d, J=8.4 Hz, 1H), 7.73 (d, J=7.6 Hz, 1H), 7.96 (s, 1H), 8.33 (s, 1H), 9.04 (br, 1H), 11.06 (br, 1H), 11.24 (br, 1H). $^{13}$C NMR (100 MHz, DMSO): δ

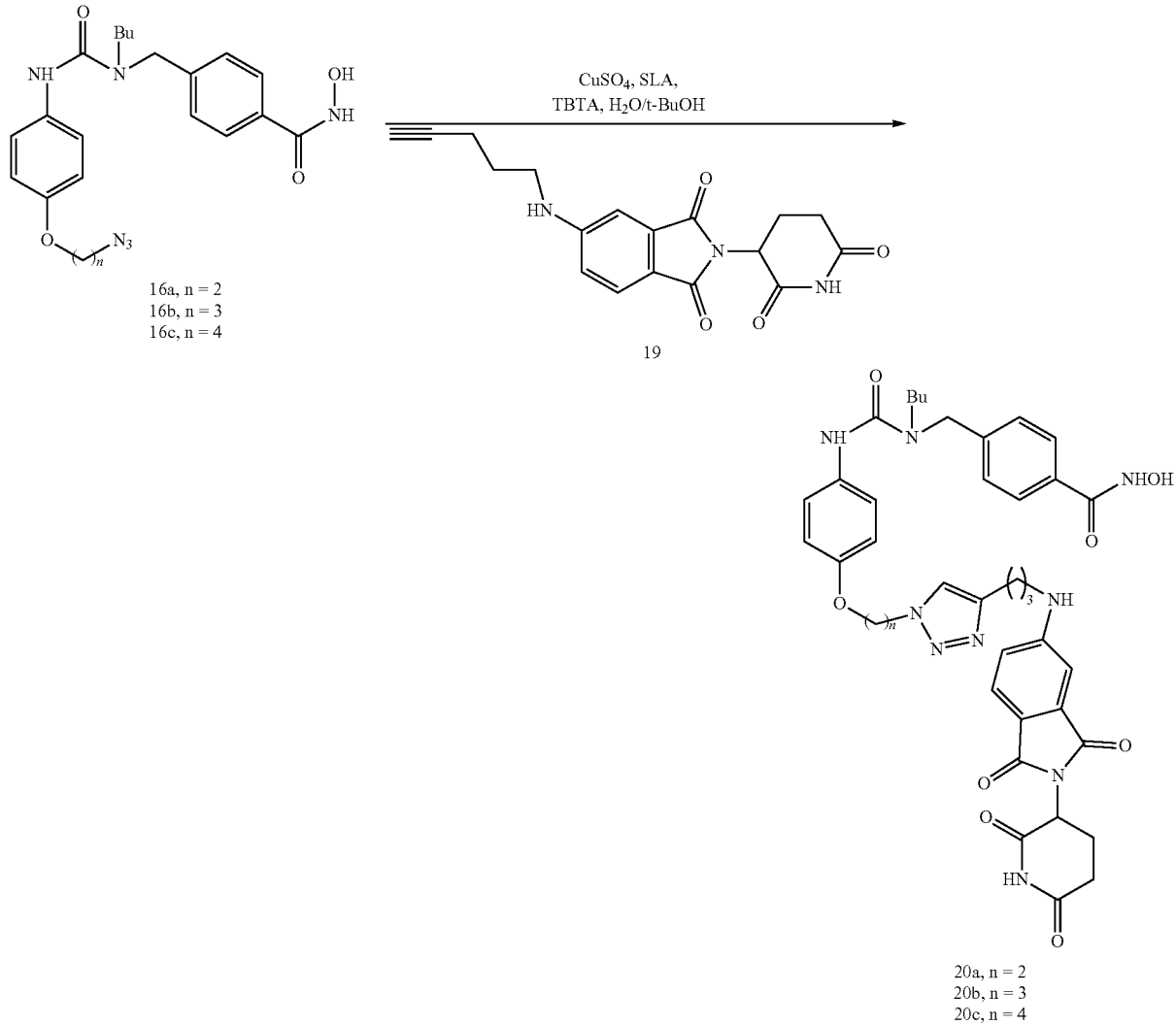

16a, n = 2
16b, n = 3
16c, n = 4

20a, n = 2
20b, n = 3
20c, n = 4

Compound 19 was prepared according to the method described in the previous literature (Yang et al., 2018, supra).

19: $^{1}$H NMR (400 MHz, DMSO): δ 1.67-1.74 (m, 2H), 1.94-1.98 (m, 1H), 2.22-2.26 (m, 2H), 2.46 (br, 2H), 2.78-2.88 (m, 2H), 3.18-3.21 (m, 2H), 4.99 (dd, J=5.6, 12.8 Hz, 1H), 6.8 (d, J=8.4 Hz, 1H), 6.9 (s, 1H), 7.1-7.2 (m, 1H), 7.53 (d, J=8.4 Hz, 1H), 11.0 (br, 1H). $^{13}$C NMR (100 MHz, DMSO):

172.82, 170.18, 167.70, 167.15, 156.26, 155.44, 154.46, 153.04, 146.27, 142.67, 142.41, 134.19, 134.09, 131.36, 127.40, 126.98, 125.08, 122.50, 121.88, 115.83, 114.35, 114.32, 113.86, 72.53, 71.25, 66.51, 63.03, 55.32, 48.98, 48.61, 46.05, 45.33, 41.88, 30.99, 29.98, 28.04, 22.54, 22.25, 19.45, 15.46, 13.81.

20b: $^{1}$H NMR (400 MHz, DMSO): δ 0.79-0.89 (m, 3H), 1.23-1.31 (m, 4H), 1.39-1.52 (m, 2H), 1.83-2.06 (m, 3H), 2.16-2.30 (m, 2H), 2.66-2.78 (m, 1H), 2.81-2.96 (m, 1H), 2.96-3.06 (m, 4H), 3.22 (br, 1H), 3.35 (br, 1H), 3.47-3.64 (m, 1H), 3.90 (br, 2H), 4.47 (br, 2H), 4.60 (br, 2H), 5.02 (br, 1H), 6.73-6.89 (m, 3H), 6.92-7.09 (m, 1H), 7.24-7.41 (m, 5H), 7.47-7.60 (m, 1H), 7.72 (br, 2H), 7.93 (s, 1H), 8.30 (s, 1H), 10.47-11.35 (m, 2H). $^{13}$C NMR (100 MHz, DMSO): δ 172.81, 170.17, 167.69, 167.15, 155.47, 154.45, 153.56, 146.27, 142.45, 134.18, 133.72, 131.36, 127.01, 126.96, 125.07, 122.06, 121.98, 115.84, 114.15, 72.54, 69.78, 64.63, 63.05, 54.94, 49.00, 48.62, 46.36, 46.06, 45.27, 30.99, 29.99, 29.61, 28.02, 22.57, 22.25, 19.46, 13.81, 8.44.

20c: $^1$H NMR (400 MHz, DMSO): δ 0.81-0.90 (m, 3H), 1.19-1.27 (m, 4H), 1.47 (br, 2H), 1.64 (br, 4H), 1.86-2.00 (m, 4H), 2.68-2.76 (m, 2H), 2.81-2.93 (m, 1H), 3.22-3.29 (m, 4H), 3.87-3.96 (m, 2H), 4.34-4.41 (m, 2H), 4.59 (br, 2H), 4.99-5.07 (m, 1H), 6.75-6.88 (m, 3H), 6.95 (br, 1H), 7.25-7.38 (m, 5H), 7.52-7.59 (m, 1H), 7.66-7.75 (m, 2H), 7.91 (s, 1H), 8.22 (s, 1H), 9.00 (br, 1H), 10.89-11.33 (m, 2H). $^{13}$C NMR (100 MHz, DMSO): δ 172.80, 170.16, 167.68, 167.14, 155.46, 154.42, 153.77, 146.22, 142.44, 134.21, 133.45, 128.72, 127.72, 126.97, 125.09, 122.01, 121.87, 115.90, 114.08, 69.78, 66.88, 63.07, 54.91, 50.42, 48.92, 48.62, 46.04, 41.89, 30.98, 29.97, 28.04, 26.57, 26.01, 25.78, 25.13, 22.56, 22.24, 19.45.

General Procedure for Syntheses of Compounds 21b and 21c:

Employing the same procedure for converting 16a-e to 18a-e, 21b-c can be obtained from 16b-c in 45-80% yield.

21b: $^1$H NMR (400 MHz, DMSO): δ 0.85 (br, 3H), 1.23 (br, 2H), 1.47-1.57 (m, 2H), 1.95-2.08 (m, 1H), 2.14-2.32 (m, 2H), 2.77-2.96 (m, 1H), 3.43 (br, 1H), 3.55-3.71 (m, 2H), 3.88 (br, 2H), 4.43-4.65 (m, 6H), 4.96-5.18 (m, 1H), 6.78 (br, 2H), 7.06 (br, 2H), 7.15 (br, 1H), 7.32 (br, 4H), 7.55 (br, 1H), 7.72 (br, 2H), 8.06 (br, 1H), 8.22 (br, 1H), 10.97-11.39 (m, 2H). $^{13}$C NMR (100 MHz, DMSO): δ 172.83, 170.10, 168.78, 167.30, 164.14, 155.49, 153.61, 145.85, 144.55, 142.48, 136.16, 133.67, 132.14, 131.40, 127.01, 123.02, 122.03, 117.63, 114.19, 110.95, 109.71, 105.46, 96.65, 91.35, 87.93, 77.22, 74.84, 73.45, 73.30, 64.66, 62.90, 54.93, 52.39, 49.03, 48.64, 46.62, 46.09, 37.69, 31.01, 30.01, 29.58, 22.18, 19.49, 13.84.

21c: $^1$H NMR (400 MHz, DMSO): δ 0.85 (br, 3H), 1.19-1.31 (m, 2H), 1.41-1.69 (m, 4H), 1.84-2.09 (m, 3H), 2.82-2.92 (m, 1H), 3.42-3.44 (m, 1H), 3.59-3.67 (m, 2H), 3.85-3.90 (m, 2H), 4.15-4.28 (m, 2H), 4.35-4.41 (m, 2H), 4.52-4.65 (m, 3H), 5.00-5.11 (m, 1H), 6.72-6.91 (m, 2H), 6.91-7.00 (m, 2H), 7.12-7.18 (m, 1H), 7.24-7.39 (m, 4H), 7.53-7.60 (m, 1H), 7.67-7.77 (m, 1H), 8.05 (br, 1H), 8.60 (br, 1H), 10.98-11.49 (m, 2H). $^{13}$C NMR (100 MHz, DMSO): δ 199.94, 172.82, 172.79, 170.83, 170.08, 169.99, 168.77, 167.42, 167.28, 155.46, 153.79, 145.83, 136.14, 133.44, 132.13, 128.84, 128.18, 127.41, 126.99, 122.89, 122.03, 117.63, 114.10, 113.87, 110.94, 109.71, 105.63, 105.44, 96.63, 93.12, 91.33, 88.21, 87.94, 87.91, 77.20,

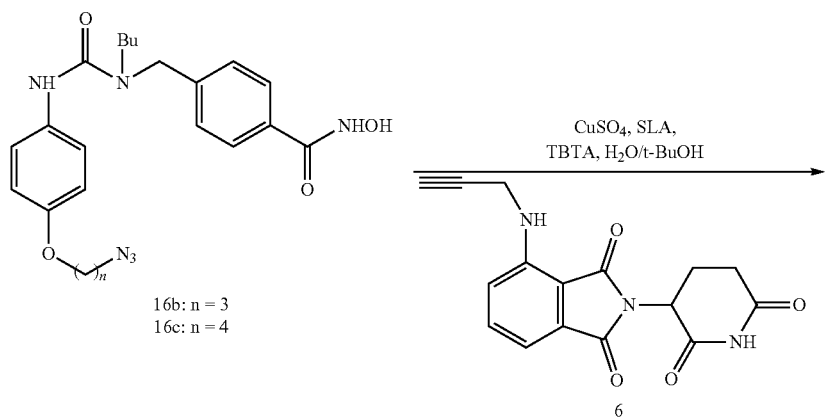

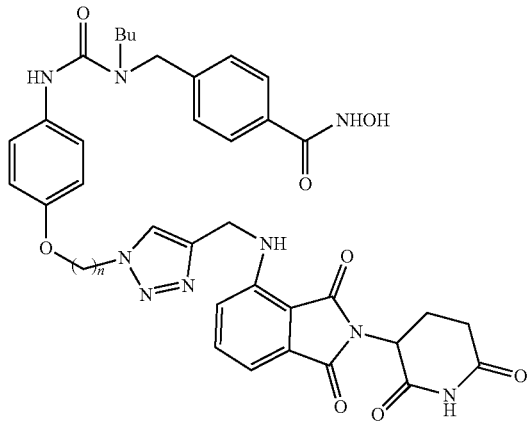

75.06, 74.82, 73.43, 73.28, 73.13, 73.05, 72.22, 69.81, 66.87, 63.10, 62.88, 52.37, 50.10, 49.95, 49.12, 48.61, 48.58, 46.06, 37.70, 30.99, 29.98, 26.58, 25.74, 22.16, 19.46, 13.81.

General Procedure for Syntheses of Compound 18x:

Referring specifically now to FIG. 7, a mixture of compound 10 (668 mg, 3.29 mmol), 22 (1 g, 3.29 mmol) and potassium carbonate (910 mg, 6.85 mmol) in Acetonitrile (6 mL) was stirred at 90° C. overnight. The mixture was cooled to room temperature and poured into water (10 mL), then extracted with ethyl acetate (10 mL×3). The combined organic phases were washed with brine (20 mL), dried over anhydrous sodium sulfate, and concentrated under reduced pressure. The residue was purified by silica gel flash column chromatography (eluted with 50% ethyl acetate in hexane) to afford compound 23 (950 mg, 85%) as yellow oil.

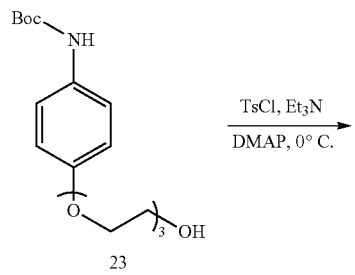

A mixture of compound 23 (950 mg, 2.76 mmol), p-toluenesulfonyl chloride (585 mg, 3.06 mmol), triethylamine (0.427 ml, 3.06 mmol) and 4-(Dimethylamino)pyridine (7 mg, 0.056 mmol) in dichloromethane (5 mL) was stirred at room temperature for overnight, quenched with water (10 mL), and extracted with dichloromethane (10 mL×3). The combined organic phases were washed with water (10 mL) and brine (10 mL), dried over anhydrous sodium sulfate, and concentrated under reduced pressure. The residue was purified by silica gel flash column chromatography (eluted with 30% ethyl acetate in hexane) to afford the 24 (1.184 g, 86%) as a colorless oil.

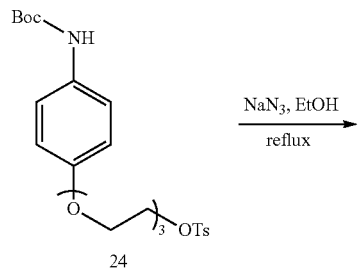

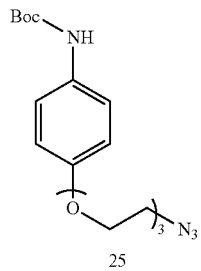

A suspension of compound 24 (100 mg, 0.2 mmol) and sodium azide (26 mg, 0.4 mmol) in EtOH (2 mL) was stirred at 90° C. overnight. Quenched with water and extracted with dichloromethane. The combined organic phase was washed with water and brine, dried over anhydrous sodium sulfate and concentrated in vacuo. The residue was purified by silica gel column chromatography (eluted with 20% ethyl acetate in hexane) to afford 25 (70 mg, 96%) as white solid.

Employing the same procedure for converting 12a to 18a, 18x can be obtained from 25 as a yellow solid.

18x: $^1$H NMR (400 MHz, DMSO): δ 0.85 (t, J=8 Hz, 3H), 1.15-1.30 (m, 4H), 1.17-1.32 (m, 2H), 1.38-1.53 (m, 2H), 1.97-2.06 (m, 1H), 2.54-2.64 (m, 1H), 2.84-2.92 (m, 1H), 3.19-3.30 (m, 3H), 3.56 (br, 3H), 3.64 (br, 2H), 3.79 (br, 2H), 3.92-4.07 (m, 3H), 4.42-4.66 (m, 6H), 5.01-5.12 (m, 1H), 6.76-6.86 (m, 2H), 7.01-7.10 (m, 1H), 7.12-7.20 (m, 1H), 7.24-7.41 (m, 5H), 7.51-7.62 (m, 1H), 7.67-7.78 (m, 2H), 7.95-8.04 (br, 1H), 8.06-8.31 (m, 1H), 11.04-11.31 (m, 1H). $^{13}$C NMR (100 MHz, DMSO): δ 173.26, 173.16, 170.51, 170.42, 169.22, 167.73, 155.85, 154.16, 146.19, 144.77, 136.57, 133.90, 132.56, 129.19, 128.49, 128.18, 127.46, 123.73, 122.37, 118.07, 114.54, 111.39, 110.12, 70.21, 70.01, 69.46, 69.19, 67.69, 49.86, 49.44, 49.02, 46.50, 37.97, 31.43, 30.43, 22.60, 19.92, 14.26.

LC-MS Analysis of 18a-e, 18x, 20a-c, 21b and 21c:

The LC-MS analysis of final products was processed on Agilent 1290 Infinity II LC system using Poroshell 120 EC-C18 column (5 cm×2.1 mm, 1.9 μm) for chromatographic separation. Agilent 6120 Quadrupole LC/MS with multimode Electrospray Ionization plus atmospheric pressure chemical ionization (MM-ES+APCI) was used for detection. The mobile phases were 5.0% methanol and 0.1% formic acid in purified water (A) and 0.1% formic acid in methanol (B). The gradient was held at 35% (0-0.2 min), increased to 100% at 2.5 min, then held at isocratic 95% B for 0.4 min and then immediately stepped back down to 35% for 0.1 min re-equilibration. The flow rate 5 was set at 0.8 mL/min.

18a: retention time, 2.287 min; MS (M+H)$^+$ found 738.3.
18b: retention time, 2.422 min; MS (M+H)$^+$ found 752.3.
18c: retention time, 2.383 min; MS (M+H)$^+$ found 766.3.
18d: retention time, 2.386 min; MS (M+H)$^+$ found 752.3.
18e: retention time, 2.443 min; MS (M+H)$^+$ found 766.3.
18x: retention time, 2.530 min; MS (M+H)$^+$ found 826.3.
20a: retention time, 2.386 min; MS (M+H)$^+$ found 766.3.
20b: retention time, 2.423 min; MS (M+H)$^+$ found 780.3.
20c: retention time, 2.464 min; MS (M+H)$^+$ found 794.3.
21b: retention time, 2.386 min; MS (M+H)$^+$ found 752.3.
21c: retention time, 2.443 min; MS (M+H)$^+$ found 766.3.

Disclosed herein are a new generation of HDAC6 degrader made by tethering pomalidomide and HDAC6 selective inhibitor Next-A. By varying the linker length and linking position, the potent and selective HDAC6 degrader 12d. which retains the degradation activity of IKZFs, was made. Further investigation confirmed its mechanism of action. The antiproliferation study demonstrated the advantage of the new HDAC6 degraders disclosed herein over HDAC6 inhibitor alone, IMiD alone, or its combination, presumably because of the multi-functions the degrader. The results highlighted the power and utility of PROTACs as a novel strategy for the development of therapeutics against multiple myeloma.

Pharmaceutical Compositions:

Also disclosed herein are pharmaceutical compositions comprising one or more of the compounds disclosed herein and their isotopic forms or a pharmaceutically suitable salt thereof as described herein. More specifically, the pharmaceutical composition may comprise one or more of the compounds described herein (or their salts) in an amount suitable for inhibiting neoplastic cell growth, in combination with a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, one or more compounds produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and one or more of the anti-neoplastic compounds disclosed herein.

For intravenous administration, the compounds may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative compound as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the medical and/or pharmaceutical arts and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

For a complete discussion of pharmaceutical manufacturing, see "Handbook of Pharmaceutical Manufacturing Formulations," $2^{nd}$ Edition, © 2018, CRC Press (Boca Raton, Fla.).

The present disclosure also includes treating neoplastic growth disorders in mammals, including humans, by administering a neoplastic cell growth inhibitory-effective amount of one or more of the compounds described herein. In particular, the compositions of the present invention may be used to treat neoplastic conditions of any and all description, but most notably those mediated or accelerated by HDAC6 enzymes.

It should be noted that the above-described pharmaceutical compositions may be utilized in connection with non-human animals, both domestic and non-domestic, as well as humans.

EXAMPLES

The following examples are included solely to provide a more complete description of the compounds disclosed and claimed herein. The examples do not limit the scope of the claims in any fashion.

Experimental Section

General Information in Synthetic Chemistry.

All reactions were conducted under a positive pressure of dry argon in glassware that had been oven dried prior to use. Anhydrous solutions of reaction mixtures were transferred via an oven dried syringe or cannula. All solvents were dried prior to use unless noted otherwise. Thin layer chromatography (TLC) was performed using precoated silica gel plates. Flash column chromatography was performed with silica gel. $^1$H and $^{13}$C nuclear magnetic resonance spectra (NMR) were recorded on Bruker 400 MHz and 500 MHz spectrometers. $^1$H NMR spectra were reported in parts per million (ppm) referenced to 7.26 ppm of $CDCl_3$ or referenced to the center line of a septet at 2.50 ppm of $DMSO-d_6$. Signal splitting patterns were described as singlet (s), doublet (d), triplet (t), quartet (q), quintet (quint), or multiplet (m), with coupling constants (J) in hertz. High resolution mass spectra (HRMS) were performed on an Electron Spray Injection (ESI) TOF mass spectrometer. The liquid chromatography mass spectrometry LC-MS analysis of final products was processed on Agilent 1290 Infinity II LC system using Poroshell 120 EC-C18 column (5 cm×2.1 mm, 1.9 μm) for chromatographic separation. Agilent 6120 Quadrupole LC/MS with multimode Electrospray Ionization plus atmospheric pressure chemical ionization (MM-ES+APCI) was used for detection. The mobile phases were 5.0% methanol and 0.1% formic acid in purified water (A) and 0.1% formic acid in methanol (B). The gradient was held at 35% (0-0.2 min), increased to 100% at 2.5 min, then held at isocratic 95% B for 0.4 min and then immediately stepped back down to 35% for 0.1 min re-equilibration. The flow rate was set at 0.8 mL/min. See Supporting Information for $^1$H and $^{13}$C NMR spectrums and LC-MS purity analysis of compounds.

Part 1:

Pomalidomide Analogues.

Alkyne materials 4a-e were made according to literature procedures. (Hideshima et al. 2016, supra.)

2-(2,6-dioxopiperidin-3-yl)-4-(prop-2-yn-1-ylamino) isoindoline-1,3-dione 4a (yellow solid, 30% yield): $^1$H NMR (500 MHz, CDCl$_3$): δ 2.12-2.16 (m, 1H), 2.27 (t, J=2.3 Hz, 1H), 2.70-2.93 (m, 3H), 4.10 (dd, J=6.1, 2.4 Hz, 2H), 4.92 (dd, J=12.3, 5.4 Hz, 1H), 6.45 (t, J=5.8 Hz, 1H), 7.03 (d, J=8.5 Hz, 1H), 7.20 (d, J=7.2 Hz, 1H), 7.56-7.59 (m, 1H), 7.97 (s, 1H). $^{13}$C NMR (126 MHz, DMSO): δ 22.74, 31.61, 32.25, 49.03, 72.49, 79.67, 111.26, 112.20, 117.39, 132.46, 136.04, 145.54, 167.55, 169.17, 169.43, 172.34. LC-MS(ESI) m/z (M+H)$^+$: 312.1; calcd for C$_{16}$H$_{13}$N$_3$O$_4$ (M+H)$^+$: 312.1.

4-(but-3-yn-1-ylamino)-2-(2,6-dioxopiperidin-3-yl) isoindoline-1,3-dione 4b (yellow solid, 59% yield): $^1$H NMR (400 MHz, DMSO): δ 1.98-2.07 (m, 1H), 2.43-2.49 (m, 2H), 2.53-2.65 (m, 2H), 2.82-2.95 (m, 2H), 3.43-3.53 (m, 2H), 4.96-5.17 (m, 1H), 6.65-6.75 (m, 1H), 6.98-7.10 (m, 1H), 7.16 (d, J=8.6 Hz, 1H), 7.53-7.65 (m, 1H), 11.09 (s, 1H). $^{13}$C NMR (100 MHz, DMSO): δ 172.80, 170.06, 168.81, 167.25, 145.96, 136.30, 132.18, 117.33, 110.84, 109.39, 81.90, 72.86, 48.57, 40.66, 39.52, 30.98, 22.14, 18.60. LC-MS(ESI) m/z (M+H)$^+$: 326.0; calcd for C$_{17}$H$_{15}$N$_3$O$_4$ (M+H)$^+$: 326.1.

2-(2,6-dioxopiperidin-3-yl)-4-(pent-4-yn-1-ylamino) isoindoline-1,3-dione 4c (yellow solid, 62% yield): $^1$H NMR (400 MHz, CDCl$_3$): δ 1.84-1.92 (m, 2H), 2.09-2.16 (m, 1H), 2.30-2.38 (m, 2H), 2.68-2.99 (m, 4H), 3.40-3.49 (m, 2H), 4.96-4.83 (m, 1H) 6.23-6.35 (m, 1H), 6.98-6.88 (m, 1H) 7.20-7.04 (m, 1H), 7.47-7.55 (m, 1H), 8.12 (brs, 1H). $^{13}$C NMR (100 MHz, DMSO): δ 172.80, 170.08, 167.27, 162.29, 146.27, 136.27, 132.25, 117.08, 110.52, 109.26, 83.78, 71.68, 42.95, 40.92, 39.94, 35.78, 27.52, 15.26. LC-MS(ESI) m/z (M+H)$^+$: 340.1; calcd for C$_{18}$H$_{17}$N$_3$O$_4$ (M+H)$^+$: 340.1.

2-(2,6-dioxopiperidin-3-yl)-5-(pent-4-yn-1-ylamino) isoindoline-1,3-dione 4d (yellow solid, 17% yield): $^1$H NMR (400 MHz, DMSO): δ 1.99-2.02 (m, 1H), 2.53-2.60 (m, 1H), 2.83-2.93 (m, 1H), 3.19 (s, 1H), 4.07 (br, 1H), 5.03-5.06 (m, 1H), 6.94 (d, J=8.4 Hz, 1H), 7.04 (br, 1H), 7.41-7.44 (m, 1H), 7.62 (d, J=8.4 Hz, 1H), 11.07 (br, 1H). $^{13}$C NMR (100 MHz, DMSO): δ 173.27, 170.59, 168.06, 167.62, 153.92, 134.42, 125.39, 117.87, 81.17, 74.33, 49.16, 32.24, 31.46, 22.67. LC-MS (ESI) m/z (M+H)$^+$: 312.0; calcd for C$_{16}$H$_{13}$N$_3$O$_4$ (M+H)$^+$: 312.1.

2-(2,6-dioxopiperidin-3-yl)-5-(prop-2-yn-1-ylamino) isoindoline-1,3-dione 4e (yellow solid, 20% yield): $^1$H NMR (400 MHz, DMSO): δ 1.67-1.74 (m, 2H), 1.94-1.98 (m, 1H), 2.22-2.26 (m, 2H), 2.46 (br, 2H), 2.78-2.88 (m, 2H), 3.18-3.21 (m, 2H), 4.99 (dd, J=5.6, 12.8 Hz, 1H), 6.81 (d, J=8.4 Hz, 1H), 6.92 (s, 1H), 7.06-7.16 (m, 1H), 7.53 (d, J=8.4 Hz, 1H), 11.02 (br, 1H). $^{13}$C NMR (100 MHz, DMSO): δ 172.81, 170.16, 167.66, 167.14, 154.34, 134.22, 125.12, 116.08, 83.89, 71.64, 48.63, 41.31, 40.43, 30.99, 27.19, 22.24, 15.38. LC-MS(ESI) m/z (M+H)$^+$: 340.0; calcd for C$_{18}$H$_{17}$N$_3$O$_4$ (M+H)$^+$: 340.1.

General Procedure for Preparing PROTAC 12a-s

A mixture of compound 5 (500 mg, 2.4 mmol), 1,2-Dibromoethane (0.82 mL, 9.6 mmol) and potassium carbonate (1.3 g, 9.6 mmol) in Acetonitrile (5 mL) was stirred at 90° C. overnight. The mixture was cooled to room temperature and poured into water (10 mL), then extracted with ethyl acetate (10 mL×3). The combined organic phases were washed with brine (20 mL), dried over anhydrous sodium sulfate, and concentrated under reduced pressure. The residue was purified by silica gel flash column chromatography (eluted with 5% ethyl acetate in hexane) to afford compound 6a (482 mg, 64%) as white solid.

A suspension of compound 6a (300 mg, 0.95 mmol) and sodium azide (308 mg, 4.7 mmol) in DMF (5 mL) was stirred at 50° C. for 4 h. Then EtOAc and water were added. The organic layer was separated and washed once with water. The resulting aqueous layer was extracted once with EtOAc. The combined organic layer was dried over with Na$_2$SO$_4$ and concentrated in vacuo. The residue was purified by silica gel chromatograph to give the product 7a (224 mg, 85%) as white solid.

For the syntheses of 8a-c (n=2-4): In a 250 mL round bottle flask filled with 100 mL of water, 7a-c was added. Then the flask topped with a condenser was dipped in a 110° C. oil bath. TLC was used to monitor the progress of the reaction. The reaction mixture was cooled down after 12 h and was extracted with ethyl acetate. The extract was washed with brine, dried over with anhydrous Na$_2$SO$_4$, and then concentrated in vacuo. The residue was purified by column chromatography on silica gel with ethyl acetate/hexane (1:1, v/v) to afford the free amine 8a-c (95-97%) as white solid.

For the syntheses of 8d-e (n=5, 6): To a solution of azide (7d-e) in DCM (45 ml) was added TFA (30 eq) dropwise at 0° C. The resulting mixture was stirred at room temperature for 4 h. Upon completion as evidenced by TLC, the reaction was quenched with NaHCO$_3$aq., then extracted with ethyl acetate (10 mL×3). The combined organic layers were washed with brine (20 mL), dried over anhydrous sodium sulfate, and concentrated under reduced pressure. The residue was purified by silica gel flash column chromatography (eluted with 20% ethyl acetate in hexane) to afford compounds 8d-e (94-96%) as white solid.

A solution of 8a (140 mg, 0.78 mmol) in THF (2 mL) was added the Carbonyldiimidazole (CDI: 153 mg, 0.94 mmol) at room temperature under an atmosphere of Ar, and the resulting solution was stirred for 2 h. Then 9 (173 mg, 0.78 mmol) in THF (2 ml) was added dropwise to the reaction mixture and the resulting mixture was stirred overnight. The reaction was quenched with saturated bicarbonate (10 mL) and extracted with DCM (3×10 mL). The combined organics were washed with brine (15 mL), dried over sodium sulfate, concentrated in vacuo, and purified via silica gel chromatography, affording the urea ester 10a as a brown oil (253 mg, 76%).

Solid NaOH (188 mg, 4.7 mmol) was dissolved in an aqueous solution of NH$_2$OH (50 wt %, 1 mL) at 0° C. Then a solution of 10a (250 mg, 0.59 mmol) in THF/MeOH (1:1, 3 mL total) was added dropwise where the biphasic solution became homogeneous upon compete addition. The resulting solution was stirred 1 h at room temperature. The reaction was quenched with AcOH (0.35 mL, 5.64 mmol). Water (10 ml) was added and the aqueous layer was extracted three times with DCM (10 mL×3). The combined organics were washed with brine (15 ml), dried over sodium sulfate, concentrated in vacuo, and purified via silica gel chromatograph, affording 11a (231 mg, 92%) as white solid.

4-((3-(4-(2-azidoethoxy)phenyl)-1-butylureido)methyl)-N-hydroxybenzamide 11a $^1$H NMR (400 MHz, CDCl$_3$): δ 0.85 (t, J=7.2 Hz, 3H), 1.16-1.24 (m, 2H), 1.48 (br, 2H), 1.95 (brs, 1H), 3.16 (br, 2H), 3.50 (br, 2H), 4.02 (br, 2H), 4.42 (br, 2H), 6.63-6.64 (m, 3H), 6.95-7.23 (m, 4H), 7.55 (br, 1H). $^{13}$C NMR (100 MHz, CDCl$_3$): δ 177.28, 166.09, 156.34, 154.60, 142.20, 132.70, 130.19, 127.58, 127.11, 122.94, 114.94, 67.41, 50.30, 50.09, 47.43, 30.39, 20.22, 14.00. LC-MS(ESI) m/z (M+H)$^+$: 427.1; calcd for C$_{21}$H$_{26}$N$_6$O$_4$ (M+H)$^+$: 427.2.

Following the procedures, 11b-e with different linker lengths were obtained as white solid.

4-((3-(4-(3-azidopropoxy)phenyl)-1-butylureido)methyl)-N-hydroxybenzamide 11b (87% yield): $^1$H NMR (400 MHz, CDCl$_3$): δ 0.86 (t, J=7.2 Hz, 3H), 1.16-1.24 (m, 2H), 1.43-1.56 (m, 2H), 1.90-2.04 (m, 3H), 3.17 (br, 2H), 3.45 (t, J=7.2 Hz, 2H), 3.87-4.01 (m, 2H), 4.44 (br, 2H), 6.61-6.82 (m, 3H), 6.79-7.22 (m, 4H), 7.56 (br, 1H). $^{13}$C NMR (100 MHz, CDCl$_3$): δ 177.15, 165.95, 156.20, 154.47, 142.07, 132.57, 130.06, 127.45, 126.97, 122.81, 114.81, 67.27, 50.17, 49.95, 47.29, 30.25, 20.09, 13.86. LC-MS(ESI) m/z (M+H)$^+$: 441.1; calcd for C$_{22}$H$_{28}$N$_6$O$_4$ (M+H)$^+$: 441.2.

4-((3-(4-(4-azidobutoxy)phenyl)-1-butylureido)methyl)-N-hydroxybenzamide 11c (92% yield): $^1$H NMR (400 MHz, CDCl$_3$): δ 0.86 (t, J=7.3 Hz, 3H), 1.16-1.33 (m, 2H), 1.42-1.57 (m, 2H), 1.68-1.86 (m, 4H), 1.95 (s, 1H), 3.16 (s, 2H), 3.31 (t, J=6.5 Hz, 3H), 3.81-3.97 (m, 2H), 4.43 (s, 2H), 6.60-6.85 (m, 3H), 6.92-7.23 (m, 4H), 7.75 (s, 1H). $^{13}$C NMR (100 MHz, CDCl$_3$): δ 177.15, 165.91, 156.25, 155.20, 142.06, 131.93, 130.05, 127.45, 126.98, 122.87, 114.62, 67.45, 51.18, 49.98, 47.30, 30.26, 26.50, 25.71, 20.10, 13.87. LC-MS(ESI) m/z (M+H)$^+$: 455.1; calcd for C$_{23}$H$_{30}$N$_6$O$_4$ (M+H)$^+$: 455.2.

4-((3-(4-((5-azidopentyl)oxy)phenyl)-1-butylureido)methyl)-N-hydroxybenzamide 11d (79% yield): $^1$H NMR (400 MHz, CDCl$_3$): δ 0.87 (t, J=7.2 Hz, 3H), 1.13-1.40 (m, 2H), 1.43-1.56 (m, 4H), 1.58-1.69 (m, 2H), 1.70-1.81 (m, 2H), 3.19 (s, 2H), 3.27 (t, J=6.8 Hz, 2H), 3.79-3.95 (m, 2H), 4.47 (s, 2H), 6.51-6.86 (m, 3H), 6.90-7.23 (m, 4H), 7.59 (brs, 1H). $^{13}$C NMR (100 MHz, CDCl$_3$): δ 165.85, 156.27, 155.39, 142.03, 131.73, 130.04, 127.48, 126.99, 122.91, 114.68, 67.89, 51.34, 50.12, 47.45, 30.32, 28.82, 28.64, 23.36, 20.13, 13.87. LC-MS(ESI) m/z (M+H)$^+$: 469.1; calcd for C$_{24}$H$_{32}$N$_6$O$_4$ (M+H)$^+$: 469.3.

4-((3-(4-((6-azidohexyl)oxy)phenyl)-1-butylureido)methyl)-N-hydroxybenzamide 11e (90% yield): $^1$H NMR (400 MHz, CDCl$_3$): δ 0.75-0.97 (m, 3H), 1.11-1.27 (m, 2H), 1.33-1.52 (m, 6H), 1.55-1.66 (m, 2H), 1.69-1.82 (m, 2H), 2.97-3.40 (m, 4H), 3.86 (s, 2H), 4.45 (s, 2H), 6.44-6.80 (m, 3H), 6.89-7.22 (m, 4H), 7.61 (brs, 1H). $^{13}$C NMR (100 MHz, CDCl$_3$): δ 165.88, 156.25, 155.41, 142.02, 131.75, 130.05, 127.48, 126.97, 122.85, 114.65, 68.02, 51.36, 50.03, 47.36, 30.28, 29.15, 28.77, 26.50, 25.65, 20.11, 13.86.

A mixture of 11a (20 mg, 0.05 mmol) and compound 4a (15 mg, 0.05 mmol), tris[(1-benzyl-1H-1,2,3-triazol-4-yl)methyl]amine (5 mg, 0.001 mmol), CuSO$_4$ (1.5 mg, 0.01 mmol), sodium ascorbate (12 mg, 0.06 mmol) in t-BuOH:H$_2$O (1.5:1) (2 mL) was stirred at room temperature for 16 h. The reaction mixture was then quenched with water (5 mL) and extracted with dichloromethane (10 mL×3). The combined organic phases were washed brine (50 mL), dried over anhydrous sodium sulfate, and concentrated under reduced pressure. The residue was purified by silica gel flash column chromatography (eluted with 30% methanol in dichloromethane) to afford the 12a (14 mg, 40%) as yellow solid.

4-((1-butyl-3-(4-(2-(4-(((2-(2,6-dioxopiperidin-3-yl)-1,3-dioxoisoindolin-4-yl)amino)methyl)-1H-1,2,3-triazol-1-yl)ethoxy)phenyl)ureido)methyl)-N-hydroxybenzamide 12a (m=1, n=2, C4 position): $^1$H NMR (400 MHz, DMSO): δ 0.70-0.90 (m, 3H), 1.22-1.32 (m, 2H), 1.33-1.56 (m, 2H), 1.91-2.14 (m, 1H), 2.52-2.70 (m, 2H), 2.79-2.95 (m, 1H), 3.36-3.58 (m, 3H), 4.12-4.86 (m, 7H), 4.96-5.17 (m, 1H), 6.51-7.43 (m, 8H), 7.47-7.79 (m, 2H), 7.87-8.64 (m, 2H), 11.10 (brs, 1H). $^{13}$C NMR (100 MHz, DMSO): δ 173.27, 170.53, 169.22, 167.74, 164.43, 155.81, 153.48, 146.29, 145.01, 142.87, 136.58, 134.44, 132.59, 127.44, 123.91, 122.33, 118.11, 114.82, 111.37, 110.15, 66.90, 55.36, 49.54, 49.04, 46.48, 38.05, 31.45, 30.39, 29.48, 22.61, 19.88, 14.24. HRMS (EI) calcd. for C$_{37}$H$_{39}$N$_9$O$_8$ (M+H)$^+$ 738.29998, found 738.29744. Purity: >98% (LCMS).

Following the procedure, compounds 12b-s were obtained as yellow solid.

4-((1-butyl-3-(4-(3-(4-(((2-(2,6-dioxopiperidin-3-yl)-1,3-dioxoisoindolin-4-yl)amino)methyl)-1H-1,2,3-triazol-1-yl)propoxy)phenyl)ureido)methyl)-N-hydroxybenzamide 12b (m=1, n=3, C4 position, 40% yield): $^1$H NMR (400 MHz, DMSO): δ 0.85 (br, 3H), 1.23 (br, 2H), 1.47-1.57 (m, 2H), 1.95-2.08 (m, 1H), 2.14-2.32 (m, 2H), 2.52-2.70 (m, 2H), 2.77-2.96 (m, 1H), 3.43 (br, 1H), 3.55-3.71 (m, 2H), 4.43-4.65 (m, 6H), 4.96-5.18 (m, 1H), 6.78 (br, 2H), 7.06 (br, 2H), 7.15 (br, 1H), 7.32 (br, 4H), 7.55 (br, 1H), 7.72 (br, 2H), 8.06 (br, 1H), 8.22 (br, 1H), 10.97-11.39 (m, 2H). $^{13}$C NMR (100 MHz, DMSO): δ 172.83, 170.10, 168.78, 167.30, 164.14, 155.49, 153.61, 145.85, 144.55, 142.48, 136.16, 133.67, 132.14, 131.40, 127.01, 123.02, 122.03, 117.63, 114.19, 110.95, 109.71, 105.46, 96.65, 91.35, 87.93, 77.22, 74.84, 73.45, 73.30, 64.66, 62.90, 54.93, 52.39, 49.03, 48.64, 46.62, 46.09, 37.69, 31.01, 30.01, 29.58, 22.18, 19.49, 13.84. HRMS (EI) calcd. for C$_{38}$H$_{41}$N$_9$O$_8$ (M+H)$^+$ 752.31563, found 752.31600. Purity: 96% (LCMS).

4-((1-butyl-3-(4-(4-(4-(((2-(2,6-dioxopiperidin-3-yl)-1,3-dioxoisoindolin-4-yl)amino)methyl)-1H-1,2,3-triazol-1-yl)butoxy)phenyl)ureido)methyl)-N-hydroxybenzamide 12c (m=1, n=4, C4 position, 45% yield): $^1$H NMR (400 MHz, DMSO): δ 0.85 (br, 3H), 1.19-1.31 (m, 2H), 1.41-1.69 (m, 4H), 1.84-2.09 (m, 3H), 2.52-2.67 (m, 2H), 2.82-2.92 (m, 1H), 3.42-3.44 (m, 1H), 3.59-3.67 (m, 2H), 4.15-4.28 (m, 2H), 4.35-4.41 (m, 2H), 4.52-4.65 (m, 3H), 5.00-5.11 (m, 1H), 6.72-6.91 (m, 2H), 6.91-7.00 (m, 2H), 7.12-7.18 (m, 1H), 7.24-7.39 (m, 4H), 7.53-7.60 (m, 1H), 7.67-7.77 (m, 1H), 8.05 (br, 1H), 8.60 (br, 1H), 10.98-11.49 (m, 2H). $^{13}$C NMR (100 MHz, DMSO): δ 199.94, 172.82, 172.79, 170.83, 170.08, 169.99, 168.77, 167.42, 167.28, 155.46, 153.79, 145.83, 136.14, 133.44, 132.13, 128.84, 128.18, 127.41, 126.99, 122.89, 122.03, 117.63, 114.10, 113.87, 110.94, 109.71, 105.63, 105.44, 96.63, 93.12, 91.33, 88.21, 87.94, 87.91, 77.20, 75.06, 74.82, 73.43, 73.28, 73.13, 73.05, 72.22, 69.81, 66.87, 63.10, 62.88, 52.37, 50.10, 49.95, 49.12, 48.61, 48.58, 46.06, 37.70, 30.99, 29.98, 26.58, 25.74, 22.16, 19.46, 13.81. HRMS (EI) calcd. for $C_{39}H_{43}N_9O_8$ (M+H)$^+$ 766.33128, found 766.33092. Purity: 95% (LCMS).

4-((1-butyl-3-(4-((5-(4-(((2-(2,6-dioxopiperidin-3-yl)-1,3-dioxoisoindolin-4-yl)amino)methyl)-1H-1,2,3-triazol-1-yl)pentyl)oxy)phenyl)ureido)methyl)-N-hydroxybenzamide 12d (m=1, n=5, C4 position, 83% yield): $^1$H NMR (400 MHz, DMSO): δ 0.61 (brs, 3H), 0.91-1.28 (m, 6H), 1.34-1.48 (m, 2H), 1.52-1.67 (m, 2H), 1.71-1.87 (m, 1H), 2.21-2.27 (m, 2H), 2.52-2.76 (m, 1H), 3.01-3.25 (m, 3H), 3.49-3.68 (m, 3H), 3.94-4.17 (m, 2H), 4.21-4.50 (m, 3H), 4.67-4.98 (m, 1H), 6.37-6.63 (m, 2H), 6.69-7.18 (m, 6H), 7.20-8.06 (m, 4H), 10.66-11.08 (m, 1H). $^{13}$C NMR (100 MHz, DMSO): δ 172.82, 170.08, 168.78, 167.29, 155.48, 153.90, 145.85, 144.43, 136.11, 133.36, 132.12, 127.00, 122.78, 122.07, 117.63, 114.05, 110.92, 109.71, 67.31, 49.27, 49.02, 48.62, 46.07, 37.72, 31.00, 29.99, 29.48, 28.11, 22.57, 22.17, 19.46, 13.80. HRMS (EI) calcd. for $C_{40}H_{45}N_9O_8$ (M+H)$^+$ 780.34693, found 780.34643. Purity: >98% (LCMS).

4-((1-butyl-3-(4-((6-(4-(((2-(2,6-dioxopiperidin-3-yl)-1,3-dioxoisoindolin-4-yl)amino)methyl)-1H-1,2,3-triazol-1-yl)hexyl)oxy)phenyl)ureido)methyl)-N-hydroxybenzamide 12e (m=1, n=6, C4 position, 75% yield): $^1$H NMR (400 MHz, DMSO): δ 0.71-0.98 (m, 3H), 1.11-1.52 (m, 8H), 1.56-1.88 (m, 4H), 1.95-2.16 (m, 1H), 2.52-2.67 (m, 2H), 2.80-3.00 (m, 1H), 3.23-3.47 (m, 3H), 3.75-3.97 (m, 2H), 4.23-4.44 (m, 2H), 4.49-4.84 (m, 3H), 4.92-5.19 (m, 1H), 6.57-6.91 (m, 2H), 6.92-7.43 (m, 6H), 7.47-8.31 (m, 3H), 10.88-11.35 (m, 1H). $^{13}$C NMR (100 MHz, DMSO): δ 172.82, 170.08, 168.78, 167.29, 153.90, 145.85, 144.43, 136.11, 133.36, 132.12, 127.00, 122.78, 122.07, 117.63, 114.05, 110.92, 109.71, 67.31, 49.27, 49.02, 48.62, 46.07, 40.43, 37.71, 31.00, 29.99, 29.48, 28.11, 22.57, 22.17, 19.46, 13.80. HRMS (EI) calcd. for $C_{41}H_{47}N_9O_8$ (M+H)$^+$ 794.36258, found 794.36865. Purity >98% (LCMS).

4-((1-butyl-3-(4-(2-(4-(2-((2-(2,6-dioxopiperidin-3-yl)-1,3-dioxoisoindolin-4-yl)amino)ethyl)-1H-1,2,3-triazol-1-yl)ethoxy)phenyl)ureido)methyl)-N-hydroxybenzamide 12f (m=2, n=2, C4 position, 47% yield): $^1$H NMR (400 MHz, DMSO): δ 0.71-0.88 (m, 3H), 1.19-1.32 (m, 2H), 1.33-1.47 (m, 2H), 1.80-2.11 (m, 2H), 2.53-2.67 (m, 2H), 2.82-2.99 (m, 3H), 3.84-4.77 (m, 8H), 4.89-5.17 (m, 1H), 6.61-7.40 (m, 8H), 7.47-7.82 (m, 2H), 7.86-8.44 (m, 2H), 11.10 (brs, 1H). $^{13}$C NMR (100 MHz, DMSO): δ 172.81, 170.08, 168.77, 167.30, 155.34, 153.06, 146.14, 144.11, 136.27, 133.96, 132.21, 126.99, 123.07, 121.86, 117.18, 114.36, 110.60, 109.30, 66.49, 54.90, 49.04, 46.01, 41.70, 30.99, 29.92, 28.24, 25.07, 22.15. HRMS (EI) calcd. for $C_{38}H_{41}N_9O_8$ (M+H)$^+$ 752.31563, found 752.31210. Purity: >98% (LCMS).

4-((1-butyl-3-(4-(3-(4-(2-((2-(2,6-dioxopiperidin-3-yl)-1,3-dioxoisoindolin-4-yl)amino)ethyl)-1H-1,2,3-triazol-1-yl)propoxy)phenyl)ureido)methyl)-N-hydroxybenzamide 12 g (m=2, n=3, C4 position, 17% yield): $^1$H NMR (400 MHz, DMSO): δ 0.86 (t, J=7.4 Hz, 3H), 1.25-1.33 (m, 2H), 1.36-1.40 (m, 1H), 1.43-1.55 (m, 2H), 1.98-2.07 (m, 1H), 2.14-2.26 (m, 2H), 2.53-2.63 (m, 2H), 2.81-3.00 (m, 3H), 3.49-3.65 (m, 3H), 3.84-3.97 (m, 2H), 4.35-4.74 (m, 4H), 5.05 (dd, J=12.8, 5.0 Hz, 1H), 6.67-6.74 (m, 1H), 6.75-6.87 (m, 2H), 7.03 (d, J=7.0 Hz, 1H), 7.12 (d, J=8.5 Hz, 1H), 7.26-7.40 (m, 3H), 7.58 (t, J=7.9 Hz, 1H), 7.72 (d, J=7.8 Hz, 1H), 7.99 (s, 1H), 8.22 (s, 1H), 11.10 (m, 1H). $^{13}$C NMR (100 MHz, DMSO): δ 172.81, 170.08, 168.77, 167.30, 155.33, 153.06, 146.14, 144.11, 136.27, 133.96, 132.21, 126.99, 123.07, 121.86, 117.18, 114.36, 110.60, 109.30, 66.49, 49.04, 41.70, 30.99, 29.92, 28.24, 25.07, 22.15, 19.41, 13.77. HRMS (EI) calcd. for $C_{39}H_{43}N_9O_8$ (M+H)$^+$ 766.33128, found 766.32762. Purity: >98% (LCMS).

4-((1-butyl-3-(4-(4-(4-(2-((2-(2,6-dioxopiperidin-3-yl)-1,3-dioxoisoindolin-4-yl)amino)ethyl)-1H-1,2,3-triazol-1-yl)butoxy)phenyl)ureido)methyl)-N-hydroxybenzamide 12 h (m=2, n=4, C4 position, 55% yield): $^1$H NMR (400 MHz, DMSO): δ 0.79-0.87 (m, 3H), 1.23-1.31 (m, 2H), 1.40-1.52 (m, 2H), 1.57-1.67 (m, 2H), 1.85-2.13 (m, 4H), 2.54-2.63 (m, 2H), 2.84-2.99 (m, 3H), 3.45-3.66 (m, 3H), 3.81-3.95 (m, 2H), 4.27-4.46 (m, 2H), 4.50-4.67 (m, 2H), 4.97-5.10 (m, 1H), 6.67-6.85 (m, 3H), 6.97-7.15 (m, 2H), 7.27-7.34 (m, 3H), 7.53-7.63 (m, 1H), 7.69-7.74 (m, 1H), 7.89-8.01 (m, 1H), 8.21 (brs, 1H), 10.95-11.59 (m, 1H). $^{13}$C NMR (100 MHz, DMSO): δ 172.80, 170.07, 168.77, 167.29, 155.47, 153.80, 146.16, 143.99, 142.46, 136.25, 133.45, 132.20, 131.39, 126.99, 122.54, 122.03, 117.17, 114.09, 110.59, 109.27, 66.89, 48.99, 46.06, 41.66, 30.99, 29.99, 27.79, 26.61, 25.74, 25.13, 22.16, 19.47, 13.81. HRMS (EI) calcd. for $C_{40}H_{45}N_9O_8$ (M+H)$^+$ 780.34693, found 780.34442. Purity: 95% (LCMS).

4-((1-butyl-3-(4-(2-(4-(3-((2-(2,6-dioxopiperidin-3-yl)-1,3-dioxoisoindolin-4-yl)amino)propyl)-1H-1,2,3-triazol-1-yl)ethoxy)phenyl)ureido)methyl)-N-hydroxybenzamide 12i (m=3, n=2, C4 position, 47% yield): $^1$H NMR (400 MHz, DMSO): δ 0.77-0.93 (m, 3H), 1.02-1.19 (m, 2H), 1.33-1.55 (m, 2H), 1.79-2.12 (m, 4H), 2.52-2.65 (m, 2H), 2.67-2.94 (m, 3H), 3.39-3.57 (m, 2H), 3.92-4.74 (m, 7H), 4.97-5.17 (m, 1H), 6.55-6.88 (m, 3H), 6.95-7.16 (m, 2H), 7.19-7.41 (m, 3H), 7.51-7.76 (m, 2H), 7.91-8.27 (m, 2H), 11.05-11.22 (m, 1H). $^{13}$C NMR (100 MHz, DMSO): δ 172.81, 170.08, 168.77, 167.30, 155.33, 153.06, 146.14, 144.11, 136.27, 133.96, 132.21, 126.99, 123.07, 121.86, 117.18, 114.36, 110.60, 109.30, 66.49, 49.04, 48.56, 46.01, 41.70, 30.99, 29.92, 28.24, 25.07, 22.15, 19.41, 13.77. HRMS (EI) calcd. for $C_{39}H_{43}N_9O_8$ (M+H)$^+$ 766.33128, found 766.32839. Purity: >98% (LCMS).

4-((1-butyl-3-(4-(3-(4-(3-((2-(2,6-dioxopiperidin-3-yl)-1,3-dioxoisoindolin-4-yl)amino)propyl)-1H-1,2,3-triazol-1-yl)propoxy)phenyl)ureido)methyl)-N-hydroxybenzamide 12j (m=3, n=3, C4 position, 68% yield): $^1$H NMR (400 MHz, DMSO): δ 0.69-0.91 (m, 3H), 0.99-1.21 (m, 2H), 1.30-1.63 (m, 2H), 1.72-2.41 (m, 6H), 2.52-2.65 (m, 2H), 2.68-2.98 (m, 3H), 3.42-3.63 (m, 2H), 3.66-3.84 (m, 7H), 4.91-5.16 (m, 1H), 6.52-6.93 (m, 3H), 6.97-7.41 (m, 4H), 7.47-7.84 (m, 2H), 7.88-8.41 (m, 2H). 11.13 (brs, 1H). $^{13}$C NMR (100 MHz, DMSO): δ 172.82, 170.11, 168.88, 167.30, 155.36, 153.59, 146.35, 136.23, 133.59, 132.23, 121.95, 117.16, 114.14, 110.42, 109.14, 64.61, 48.56, 46.37, 45.99, 30.99, 29.90, 29.57, 28.39, 22.38, 22.16, 19.39, 13.75. HRMS (EI) calcd. for $C_{40}H_{45}N_9O_8$ (M+H)$^+$ 780.34693, found 780.34609. Purity 97% (LCMS).

4-((1-butyl-3-(4-(4-(4-(3-((2-(2,6-dioxopiperidin-3-yl)-1,3-dioxoisoindolin-4-yl)amino)propyl)-1H-1,2,3-triazol-1-yl)butoxy)phenyl)ureido)methyl)-N-hydroxybenzamide 12k (m=3, n=4, C4 position, 37% yield): $^1$H NMR (400 MHz, DMSO): δ 0.75-0.89 (m, 3H), 1.24-1.37 (m, 2H), 1.38-1.52 (m, 2H), 1.59-1.69 (m, 2H), 1.75-2.08 (m, 6H), 2.53-2.64 (m, 2H), 2.65-2.77 (m, 2H), 2.83-2.94 (m, 1H), 3.51-3.66 (m, 2H), 3.82-4.08 (m, 3H), 4.28-4.68 (m, 4H), 4.98-5.14 (m, 1H), 6.57-6.91 (m, 3H), 6.96-7.16 (m, 2H), 7.28-7.41 (m, 3H), 7.53-7.76 (m, 2H), 7.87-8.03 (m, 1H), 8.09-8.34 (m, 1H). $^{13}$C NMR (100 MHz, DMSO): δ 172.83, 170.11, 168.88, 167.31, 155.49, 153.79, 146.36, 146.18, 136.26, 133.47, 132.24, 128.74, 126.97, 122.02, 121.88, 117.18, 114.10, 110.43, 109.14, 66.89, 48.95, 48.56, 46.04, 41.33, 39.52, 30.99, 29.98, 28.42, 26.57, 25.79, 22.39, 22.17, 19.46, 13.81. HRMS (EI) calcd. for $C_{41}H_{47}N_9O_8$ (M+H)$^+$ 794.36258, found 794.35818. Purity >98% (LCMS).

4-((1-butyl-3-(4-(2-(4-(((2-(2,6-dioxopiperidin-3-yl)-1,3-dioxoisoindolin-5-yl)amino)methyl)-1H-1,2,3-triazol-1-yl)ethoxy)phenyl)ureido)methyl)-N-hydroxybenzamide 12l (m=1, n=2, C5 position, 30% yield): $^1$H NMR (400 MHz, DMSO): δ 0.85 (t, J=6.8 Hz, 3H), 1.12-1.33 (m, 2H), 1.39-1.53 (m, 2H), 1.96-2.07 (m, 1H), 2.54-2.64 (m, 2H), 2.80-2.95 (m, 1H), 3.18-3.27 (m, 2H), 4.32 (br, 2H), 4.49 (br, 2H), 4.59 (br, 2H), 4.72 (br, 2H), 4.99-5.08 (m, 1H), 6.78 (d, J=8 Hz, 2H), 6.96 (d, J=7.6 Hz, 1H), 7.08 (br, 1H), 7.22-7.41 (m, 4H), 7.58 (d, J=8 Hz, 2H), 7.72 (d, J=7.2 Hz, 2H), 8.09 (s, 1H), 8.24, (s, 1H), 9.01 (br, 1H), 11.01-11.25 (m, 2H). $^{13}$C NMR (100 MHz, DMSO): δ 172.82, 170.17, 167.64, 167.15, 164.10, 155.43, 154.02, 153.03, 144.29, 142.43, 134.07, 131.39, 126.99, 125.00, 123.55, 121.94, 116.69, 114.34, 66.45, 49.09, 49.00, 48.67, 46.07, 37.99, 31.01, 29.99, 22.24, 19.47, 13.82. HRMS (EI) calcd. for $C_{37}H_{39}N_9O_8$ (M+H)$^+$ 738.29998, found 738.29690. Purity: 96% (LCMS).

4-((1-butyl-3-(4-(3-(4-(((2-(2,6-dioxopiperidin-3-yl)-1,3-dioxoisoindolin-5-yl)amino)methyl)-1H-1,2,3-triazol-1-yl)propoxy)phenyl)ureido)methyl)-N-hydroxybenzamide 12m (m=1, n=3, C5 position, 35% yield): $^1$H NMR (400 MHz, DMSO): δ 0.85 (br, 3H), 1.24 (br, 2H), 1.39-1.59 (m, 2H), 1.98 (br, 1H), 2.23 (br, 2H), 2.50-2.66 (m, 2H), 2.78-2.96 (m, 1H), 3.19-3.35 (m, 2H), 3.90 (br, 2H) 4.33-4.69 (m, 6H), 4.92-5.13 (m, 1H), 6.79 (br, 2H), 6.95 (br, 1H), 7.07 (br, 1H), 7.33 (br, 4H), 7.58 (br, 2H), 7.73 (br, 2H), 8.08 (s, 1H), 8.25 (s, 1H), 9.00 (br, 1H), 10.86-11.30 (m, 2H). $^{13}$C NMR (100 MHz, DMSO): δ 172.81, 170.16, 167.64, 167.15, 155.47, 154.00, 153.58, 144.27, 142.46, 134.06, 133.68, 131.37, 128.73, 127.73, 127.00, 125.00, 123.11, 122.02, 116.67, 114.17, 64.61, 63.09, 49.02, 48.66, 46.57, 46.07, 38.07, 31.00, 29.99, 29.62, 22.23, 19.46, 13.81. HRMS (EI) calcd. for $C_{38}H_{41}N_9O_8$ (M+H)$^+$ 752.31653, found 752.31133. Purity >98% (LCMS).

4-((1-butyl-3-(4-(4-(4-(((2-(2,6-dioxopiperidin-3-yl)-1,3-dioxoisoindolin-4-yl)amino)methyl)-1H-1,2,3-triazol-1-yl)butoxy)phenyl)ureido)methyl)-N-hydroxybenzamide 12n (m=1, n=4, C5 position, 49% yield): $^1$H NMR (400 MHz, DMSO): δ 0.81 (t, J=7.2 Hz, 3H), 1.15-1.27 (m, 3H), 1.37-1.48 (m, 3H), 1.54-1.67 (m, 2H), 1.84-1.93 (m, 2H), 2.40-2.48 (m, 2H), 2.76-2.93 (m, 1H), 3.21-3.30 (m, 2H), 3.82-3.91 (m, 2H), 4.31-4.39 (m, 2H), 4.40-4.49 (m, 2H), 4.57 (br, 2H), 4.93-5.09 (m, 1H), 6.75 (d, J=8.8 Hz, 2H), 6.93 (d, J=8.0 Hz, 1H), 7.04 (br, 1H), 7.26-7.32 (m, 5H), 7.53 (d, J=8.4 Hz, 1H), 7.61-7.67 (m, 1H), 7.70 (d, J=8 Hz, 2H), 8.03 (s, 1H), 8.26 (s, 1H), 11.03-11.36 (m, 2H). $^{13}$C NMR (100 MHz, DMSO): δ 172.84, 170.18, 167.66, 167.17, 155.53, 154.05, 153.78, 144.24, 142.48, 134.05, 133.54, 131.36, 128.74, 127.77, 127.03, 126.99, 125.00, 123.00, 122.06, 116.63, 114.09, 72.55, 66.90, 63.06, 54.96, 52.73, 49.09, 49.04, 48.67, 46.10, 31.02, 30.02, 26.66, 25.76, 22.26, 19.48, 14.11, 13.84. HRMS (EI) calcd. for $C_{39}H_{43}N_9O_8$ (M+H)$^+$ 766.33128, found 766.33104. Purity: 96% (LCMS).

4-((1-butyl-3-(4-((5-(4-(((2-(2,6-dioxopiperidin-3-yl)-1,3-dioxoisoindolin-5-yl)amino)methyl)-1H-1,2,3-triazol-1-yl)pentyl)oxy)phenyl)ureido)methyl)-N-hydroxybenzamide 12o (m=1, n=5, C5 position, 43% yield): $^1$H NMR (400 MHz, DMSO): δ 0.82-0.88 (m, 3H), 1.14-1.23 (m, 2H), 1.31-1.40 (m, 2H), 1.43-1.51 (m, 2H), 1.62-1.74 (m, 2H), 1.79-1.91 (m, 2H), 1.92-2.04 (m, 1H), 2.52-2.61 (m, 2H), 2.76-2.96 (m, 1H), 3.28-3.38 (m, 2H), 3.78-3.92 (m, 2H), 4.35 (br, 2H), 4.47 (br, 2H), 4.59 (br, 2H), 4.96-5.09 (m, 1H), 6.75-6.81 (m, 2H), 6.91-6.98 (m, 1H), 7.02-7.13 (m, 2H), 7.21-7.44 (m, 5H), 7.49-7.61 (m, 2H), 7.66-7.76 (m, 2H), 8.04 (s, 1H), 8.22 (s, 1H), 8.99 (br, 1H), 10.94-11.36 (m, 2H). $^{13}$C NMR (100 MHz, DMSO): 172.80, 170.13, 167.62, 167.14, 164.09, 156.26, 155.48, 154.00, 153.88, 144.14, 142.47, 134.04, 133.37, 131.37, 128.73, 127.40, 126.99, 124.98, 122.91, 122.06, 116.65, 114.04, 113.86, 72.50, 69.82, 69.09, 67.31, 63.08, 49.25, 48.99, 46.05, 41.15, 38.08, 30.99, 29.99, 29.51, 28.12, 22.57, 22.22, 19.46, 13.81. HRMS (EI) calcd. for $C_{40}H_{45}N_9O_8$ (M+H)$^+$ 780.34693, found 780.34703. Purity: 95% (LCMS).

4-((1-butyl-3-(4-((6-(4-(((2-(2,6-dioxopiperidin-3-yl)-1,3-dioxoisoindolin-5-yl)amino)methyl)-1H-1,2,3-triazol-1-yl)hexyl)oxy)phenyl)ureido)methyl)-N-hydroxybenzamide 12p (m=1, n=6, C5 position, 37% yield): $^1$H NMR (400 MHz, DMSO): 0.79-0.90 (m, 3H), 1.18-1.30 (m, 4H), 1.34-1.51 (m, 4H), 1.58-1.70 (m, 2H), 1.73-1.88 (m, 2H), 1.92-2.04 (m, 1H), 2.53-2.62 (m, 2H), 2.78-2.93 (m, 1H), 2.38-2.54

(m, 2H), 3.79-3.94 (m, 2H), 4.30-4.38 (m, 2H), 4.42-4.49 (m, 2H), 4.54-4.66 (m, 2H), 4.97-5.09 (m, 1H), 6.74-6.84 (m, 2H), 6.90-6.99 (m, 1H), 7.06 (br, 1H), 7.25-7.43 (m, 5H), 7.53-7.61 (m, 2H), 7.68-7.78 (m, 2H), 8.03 (s, 1H), 8.20 (s, 1H), 10.99-11.32 (m, 2H). $^{13}$C NMR (100 MHz, DMSO): δ 172.80, 170.14, 167.62, 167.14, 164.10, 155.48, 153.99, 153.95, 144.13, 142.47, 134.04, 133.33, 131.38, 128.74, 127.74, 126.99, 124.99, 122.89, 122.08, 116.66, 114.06, 67.40, 49.26, 48.99, 48.65, 46.06, 38.08, 30.99, 29.99, 29.68, 28.56, 25.60, 24.94, 22.23, 19.47, 13.82. HRMS (EI) calcd. for $C_{41}H_{47}N_9O_8$ (M+H)$^+$ 794.36258, found 794.35817. Purity: 95% (LCMS).

4-((1-butyl-3-(4-(2-(4-(3-((2-(2,6-dioxopiperidin-3-yl)-1,3-dioxoisoindolin-5-yl)amino)propyl)-1H-1,2,3-triazol-1-yl)ethoxy)phenyl)ureido)methyl)-N-hydroxybenzamide 12q (m=3, n=2, C5 position, 16% yield): $^1$H NMR (400 MHz, DMSO): δ 0.84 (t, J=7.2 Hz, 3H), 1.08-1.17 (m, 2H), 1.38-1.51 (m, 2H), 1.53-1.57 (m, 1H), 1.84-2.04 (m, 2H), 2.69-2.77 (m, 2H), 2.82-2.91 (m, 1H), 3.22-3.36 (m, 4H), 3.92-4.03 (m, 1H), 4.12-4.18 (m, 1H), 4.27-4.36 (m, 2H), 4.30-4.50 (m, 1H), 4.54-4.62 (m, 2H), 4.65-4.73 (m, 2H), 4.99-5.07 (m, 1H), 6.76-6.85 (m, 3H), 6.97 (br, 1H), 7.07 (br, 1H), 7.30 (d, J=7.6 Hz, 1H), 7.35 (d, J=7.6 Hz, 1H), 7.55 (d, J=8.4 Hz, 1H), 7.73 (d, J=7.6 Hz, 1H), 7.96 (s, 1H), 8.33 (s, 1H), 9.04 (br, 1H), 11.06 (br, 1H), 11.24 (br, 1H). $^{13}$C NMR (100 MHz, DMSO): δ 172.82, 170.18, 167.70, 167.15, 156.26, 155.44, 154.46, 153.04, 146.27, 142.67, 142.41, 134.19, 134.09, 131.36, 127.40, 126.98, 125.08, 122.50, 121.88, 115.83, 114.35, 114.32, 113.86, 72.53, 71.25, 66.51, 63.03, 55.32, 48.98, 48.61, 46.05, 45.33, 41.88, 30.99, 29.98, 28.04, 22.54, 22.25, 19.45, 15.46, 13.81. HRMS (EI) calcd. for $C_{39}H_{43}N_9O_8$ (M+H)$^+$ 766.33128, found 766.32746. Purity: 96% (LCMS).

4-((1-butyl-3-(4-(3-(4-(3-((2-(2,6-dioxopiperidin-3-yl)-1,3-dioxoisoindolin-5-yl)amino)propyl)-1H-1,2,3-triazol-1-yl)propoxy)phenyl)ureido)methyl)-N-hydroxybenzamide 12r (m=3, n=3, C5 position, 24% yield): $^1$H NMR (400 MHz, DMSO): δ 0.79-0.89 (m, 3H), 1.23-1.31 (m, 4H), 1.39-1.52 (m, 2H), 1.83-2.06 (m, 3H), 2.16-2.30 (m, 2H), 2.66-2.78 (m, 1H), 2.81-2.96 (m, 1H), 2.96-3.06 (m, 4H), 3.22 (m, 1H), 3.35 (br, 1H), 3.47-3.64 (m, 1H), 3.90 (br, 2H), 4.47 (br, 2H), 4.60 (br, 2H), 5.02 (br, 1H), 6.73-6.89 (m, 3H), 6.92-7.09 (m, 1H), 7.24-7.41 (m, 5H), 7.47-7.60 (m, 1H), 7.72 (br, 2H), 7.93 (s, 1H), 8.30 (s, 1H), 10.47-11.35 (m, 2H). $^{13}$C NMR (100 MHz, DMSO): δ 172.81, 170.17, 167.69, 167.15, 155.47, 154.45, 153.56, 146.27, 142.45, 134.18, 133.72, 131.36, 127.01, 126.96, 125.07, 122.06, 121.98, 115.84, 114.15, 72.54, 69.78, 64.63, 63.05, 54.94, 49.00, 48.62, 46.36, 46.06, 45.27, 30.99, 29.99, 29.61, 28.02, 22.57, 22.25, 19.46, 13.81, 8.44. HRMS (EI) calcd. for $C_{40}H_{45}N_9O_8$ (M+H)$^+$ 780.34693, found 780.34262. Purity: 95% (LCMS).

4-((1-butyl-3-(4-(4-(4-(3-((2-(2,6-dioxopiperidin-3-yl)-1,3-dioxoisoindolin-5-yl)amino)propyl)-1H-1,2,3-triazol-1-yl)butoxy)phenyl)ureido)methyl)-N-hydroxybenzamide 12s (m=3, n=4, C5 position, 14% yield): $^1$H NMR (400 MHz, DMSO): δ 0.81-0.90 (m, 3H), 1.19-1.27 (m, 4H), 1.47 (br, 2H), 1.64 (br, 4H), 1.86-2.00 (m, 4H), 2.68-2.76 (m, 2H), 2.81-2.93 (m, 1H), 3.22-3.29 (m, 4H), 3.87-3.96 (m, 2H), 4.34-4.41 (m, 2H), 4.59 (br, 2H), 4.99-5.07 (m, 1H), 6.75-6.88 (m, 3H), 6.95 (br, 1H), 7.25-7.38 (m, 5H), 7.52-7.59 (m, 1H), 7.66-7.75 (m, 2H), 7.91 (s, 1H), 8.22 (s, 1H), 9.00 (br, 1H), 10.89-11.33 (m, 2H). $^{13}$C NMR (100 MHz, DMSO): δ 172.80, 170.16, 167.68, 167.14, 155.46, 154.42, 153.77, 146.22, 142.44, 134.21, 133.45, 128.72, 127.72, 126.97, 125.09, 122.01, 121.87, 115.90, 114.08, 69.78, 66.88, 63.07, 54.91, 50.42, 48.92, 48.62, 46.04, 41.89, 30.98, 29.97, 28.04, 26.57, 26.01, 25.78, 25.13, 22.56, 22.24, 19.45. HRMS (EI) calcd. for $C_{41}H_{47}N_9O_8$ (M+H)$^+$ 793.35476, found 794.36226. Purity: 93% (LCMS).

Following the procedure to prepare 12a-s, compound 13 was obtained by the same method as white solid in 93% yield.

Methyl 4-((1-butyl-3-(4-((5-(4-(((2-(2,6-dioxopiperidin-3-yl)-1,3-dioxoisoindolin-4-yl)amino)methyl)-1H-1,2,3-triazol-1-yl)pentyl)oxy)phenyl)ureido)methyl)benzoate 13

$^1$H NMR (400 MHz, DMSO-d$_6$): δ 0.86 (t, J=7.3 Hz, 3H), 1.24-1.30 (m, 2H), 1.31-1.39 (m, 2H), 1.42-1.54 (m, 2H), 1.63-1.75 (m, 2H), 1.80-1.91 (m, 2H), 2.00-2.08 (m, 1H), 2.55-2.64 (m, 1H), 2.82-2.95 (m, 1H), 3.29 (t, J=7.6 Hz, 2H), 3.63 (s, 1H), 3.84 (s, 1H), 3.86-3.89 (m, 1H), 4.35 (t, J=7.0 Hz, 2H), 4.58-4.65 (m, 3H), 5.07 (dd, J=12.9, 5.4 Hz, 1H), 5.60 (s, 1H), 6.72-6.85 (m, 2H), 7.02-7.11 (m, 2H), 7.16 (d, J=8.6 Hz, 1H), 7.27-7.35 (m, 3H), 7.40 (d, J=8.1 Hz, 2H), 7.56 (dd, J=8.5, 7.1 Hz, 1H), 7.94 (d, J=8.1 Hz, 2H), 8.03 (s, 1H), 8.24 (s, 1H), 11.11 (s, 1H). $^{13}$C NMR (100 MHz, DMSO): δ 172.78, 170.05, 168.76, 167.26, 166.09, 155.46, 153.91, 145.83, 145.01, 144.41, 143.69, 136.21, 136.09, 133.32, 132.11, 129.30, 128.72, 128.19, 128.02, 127.71, 127.30, 124.17, 122.75, 122.08, 117.61, 114.03, 110.89, 109.69, 67.30, 59.75, 52.71, 52.04, 49.25, 49.11, 48.57, 46.94, 46.19, 37.70, 30.99, 30.00, 29.46, 28.10, 22.55, 22.15, 19.45, 13.79. HRMS (EI) calcd. for $C_{41}H_{46}N_8O_8$ (M+H)$^+$ 779.35169, found 779.34748. Purity: >98% (LCMS).

To a solution of 4a (60 mg, 0.16 mmol) in DMF (2 ml) was added Cs$_2$CO$_3$ (80 mg, 0.24 mmol) and CH$_3$I (15 μL, 0.24 mmol) at room temperature. The resulting mixture was stirred overnight. Upon completion as evidenced by TLC, the reaction was quenched by H$_2$O, then extracted with ethyl acetate (10 mL×3). The combined organic layers were washed with brine (20 mL), dried over anhydrous sodium sulfate, and concentrated under reduced pressure. The residue was purified by silica gel flash column chromatography (eluted with 25% ethyl acetate in hexane) to afford compound 14 (44%) as a yellow solid.

2-(1-methyl-2,6-dioxopiperidin-3-yl)-4-(prop-2-yn-1-yl)isoindoline-1,3-dione 14

$^1$H NMR (400 MHz, CDCl$_3$): δ 2.05-2.16 (m, 1H), 2.24-2.33 (m, 1H), 2.68-2.82 (m, 2H), 2.88-3.03 (m, 1H), 3.20 (s, 1H), 4.08 (dd, J=6.1, 2.5 Hz, 2H), 4.86-4.98 (m, 1H), 6.44 (t, J=6.0 Hz, 1H), 7.01 (d, J=8.5 Hz, 1H), 7.18 (d, J=7.1 Hz, 1H), 7.52-7.60 (m, 1H). $^{13}$C NMR (100 MHz, CDCl$_3$): δ 171.35, 169.52, 169.04, 167.71, 145.59, 136.17, 132.58, 117.20, 112.75, 111.59, 79.30, 72.26, 49.82, 32.41, 32.03, 27.37, 22.20.
LC-MS(ESI) m/z (M+H)$^+$: 326.1; calcd for $C_{21}H_{26}N_6O_4$ (M+H)$^+$: 326.1.

Following the procedure to prepare 12a-s, compound 15 was obtained by the same method as yellow solid in 70% yield.

4-((1-butyl-3-(4-((5-(4-(((2-(1-methyl-2,6-dioxopiperidin-3-yl)-1,3-dioxoisoindolin-4-yl)amino) methyl)-1H-1,2,3-triazol-1-yl)pentyl)oxy)phenyl) ureido)methyl)-N-hydroxybenzamide 15

$^1$H NMR (400 MHz, DMSO-$d_6$): δ 0.66-0.96 (m, 3H), 1.18-1.52 (m, 6H), 1.62-1.76 (m, 2H), 1.77-1.92 (m, 2H), 1.97-2.11 (m, 1H), 2.51-2.63 (m, 2H), 2.69-3.83 (m, 1H), 3.02 (s, 3H), 3.14-3.49 (m, 3H), 3.71-4.00 (m, 2H), 4.21-4.41 (m, 2H), 4.46-4.81 (m, 3H), 5.01-5.28 (m, 1H), 6.57-6.94 (m, 2H), 6.98-8.32 (m, 10H). $^{13}$C NMR (100 MHz, DMSO): δ 171.78, 169.79, 168.74, 167.23, 155.40, 153.86, 145.86, 144.38, 136.13, 133.33, 132.09, 128.71, 127.70, 122.77, 122.00, 117.65, 114.01, 110.92, 109.65, 67.28, 49.24, 49.13, 37.69, 31.10, 29.92, 29.46, 28.09, 26.57, 22.55, 21.37, 19.41, 13.76. HRMS (EI) calcd. for $C_{41}H_{47}N_9O_8$ (M+H)$^+$ 794.36258, found 794.35934. Purity: 98% (LCMS).

Chemical Reagent for Biology and Antibodies.

Janus Green B (201677) and Resazurin sodium salt (R7017) were purchased from Sigma-Aldrich (St. Louis, Mo., USA). Pomalidomide (S1567), thalidomide (S1193), lenalidomide (S1029), MG132 (S2619), and bortezomib (S1013) were purchased from Selleckchem (Houston, Tex., USA). SAHA (Ser. No. 10/009,929) was purchased from Cayman Chemical (Ann Arbor, Mich., USA). Antibodies against HDACs, IKZF1, IKZF3, Ac-α-Tubulin (K40), Histone-3, Ac-Histone-3 (K9), Caspase-3, PARP and anti-mouse- and anti-rabbit HRP-linked antibodies were purchased from Cell Signaling Technology (CST; Danvers, Mass., USA). Antibodies against α-Tubulin and β-Actin were purchased from R&D Systems, Inc. (Minneapolis, Minn., USA).

Cell Lines and Culture Methods.

Cell lines were purchased from American Type Culture Collection (ATCC, Manassas, Va., USA) unless otherwise noted. Hela and HepG2 cells were cultured in DMEM medium (1 g/L glucose) (Corning Life Sciences, Tewksbury, Mass., USA) supplemented with 10% FBS and 1% penicillin/streptomycin. A375, A431 and MCF-7 cells were cultured in DMEM medium (4.5 g/L glucose; Corning) supplemented with 10% FBS and 1% penicillin/streptomycin. MM1S, RPMI8226, A375, RS4;11 and Jurkat cells were cultured in RPMI-1640 medium (Corning) supplemented with 10% FBS, 1% sodium pyruvate, and 1% penicillin/streptomycin, 10 mM HEPES. All cell lines were grown at 37° C. in a humidified 5% $CO_2$ atmosphere.

In-Cell ELISA Assay.

MM1S cells were harvested and plated with 5×10$^5$ cells in 100 μL media per well 96-wells plate. After overnight seeding, 25 μL media containing 5× dosing concentration of the compounds or vehicle was added to each well. After 6-hour treatment at 37° C. in a humidified 5% $CO_2$ atmosphere, cells were fixed by adding 125 μL 8% formaldehyde in TBS buffer (137 mM NaCl, 25 mM Tris, 2.7 mM potassium chloride, pH 7.6) and incubated at room temperature (RT) for 15 minutes. Removal of fixing solution was followed by once rinse and twice washes with TBS-T washing buffer (137 mM NaCl, 20 mM Tris, 0.1% Tween, pH 7.6). Cells were then permeabilized by adding 100 μL 0.1% Triton-X in TBS and incubated at RT for 15 minutes. Removal of permeabilizing solution was followed by once rinse and once wash with TBS-T. Cellular endogenous peroxidases were quenched by adding 100 μL 1% $H_2O_2$ in TBS and incubation at RT for 20 minutes. Removal of quenching solution was followed by once rinse and once wash with TBS-T. Non-specific binding sites were blocked by adding 200 L 5% BSA in TBS-T (with 0.02% $NaN_3$) and incubation at 4° C. overnight. Removal of blocking solution was followed by adding 50 μL primary antibody solution (HDAC6 Rabbit mAb, CST #7558, 1:1000 in 5% BSA in TBS-T with 0.02% $NaN_3$) and incubation at RT for 2 hours. Two or more wells treated with DMSO or untreated were added blocking solution without antibody as background control. Removal of primary antibody solution was followed by once rinse and three times washes with TBS-T. Secondary antibody solution (Anti-rabbit IgG, HRP-linked Antibody, CST #7074, 1:2000 in 1% BSA in TBS-T) was added into cells and incubated at RT for 1 hour. Removal of secondary antibody solution was followed by once rinse and four times washes with TBS-T. TMB substrates (BioLegend, Inc., San Diego, Calif., USA, catalog no. 421101) were premixed, added into cells and incubated in dark at RT for 20 minutes. Stop solution (2N $H_2SO_4$ in dd$H_2O$) was added into reaction mixture and incubated at RT for 5 minutes with gentle shaking. The optical density (OD) of each well was read at 450 nm and 570 nm by FLUOstar Omega microplate reader (BMG LabTech, Cary, N.C., USA). ELISA OD was obtained by subtracting the $OD_{570}$ from $OD_{450}$. Normalization of ELISA OD to cell number was processed by Janus Green Stain. The normalized signal (NS) was calculated by followed formula:

$$NS = \frac{ELISA \text{ OD of sample} - ELISA \text{ OD of background control}}{Janus \text{ Green OD}}$$

The relative HDAC6 expression was calculated by divide NS of compound treated well by average NS of vehicle/DMSO treated wells and marked as "relative HDAC6 expression % of vehicle".

Immunoblot.

When the cells reached 90% confluence, they were harvested and plated 1×10$^6$ cells per well in 6-well plate. After overnight seeding, the cells were treated with a solution of compounds or vehicle in culture medium. The culture medium was removed after treatment and then washed twice with cold PBS. To obtain whole cell lysate, all cells were treated with RIPA lysis buffer (25 mM Tris, pH 7-8, 150 mM NaCl, 0.1% SDS, 0.5% sodium deoxycholate, 1% Triton X-100, protease inhibitor cocktail (Roche, 1 tablet per 10 mL) and 1 mM PMSF) on ice for 10 minutes. Supernatant was collected after spinning down at 16,000 g at 4° C. for 15 minutes. Protein concentration was measured by using the Pierce BCA protein assay (Thermo Fisher Scientific). About 10-40 μg of total protein was mixed with 4× Laemmli Loading Dye (250 mM Tris, pH 6.8, 40% glycerol, 5% SDS, 0.005% bromophenol blue, 4% BME) and heated at 95-100° C. for 5 minutes. The heated sample was then subjected to 7.5-12% SDS-PAGE and transferred to PVDF membrane (Bio-Rad,). The membrane was blocked in 5% non-fat milk (Bio-rad) in TBS-T washing buffer (137 mM NaCl, 20 mM Tris, 0.1% Tween) and then incubated with primary antibodies at 4° C. overnight. The membrane was washed 3 times with TBS-T, incubated with secondary horseradish peroxidase (HRP) linked antibodies for 1 hour, then washed 3 more times with TBS-T. Clarity ECL substrate (Bio-Rad Laboratories, Hercules, Calif., USA) was incubated with membrane for 5 minutes. The Immunoblot was generated by ChemiDoc MP Imaging Systems (Bio-Rad) and analyzed by Image J software (only available for download online at https://imagej.net/Downloads). A band intensity bar graph was generated, and the curve was fitted using "log(inhibitor) vs. response (three parameters)" using GraphPad Prism software (GraphPad Software, San Diego, Calif., USA).

Cell Viability Assay.

MM1S cells were harvested and plated with $1\times10^5$ cells in 400 μL media per well in 96-well plate. After overnight seeding, 25 μL media containing 5× dosing concentration of the compounds or vehicle was added to each well. After 72-hour treatment at 37° C. in a humidified 5% $CO_2$ atmosphere, 12.5 μL 10× resazurin solution (1 mg/mL) was added to each well. Then cells were incubated at 37° C. overnight. The optical density was read at 570 nm and 600 nm by plate reader.

The relative viability (RV) was measured by followed formula:

$$RV = \frac{117216 \times OD_{570} \text{ of sample} - 80586 \times OD_{600} \text{ of sample}}{117216 \times OD_{570} \text{ of vehicle} - 80586 \times OD_{600} \text{ of vehicle}}$$

The bar graph was generated using GraphPad Prism software.

Real-Time Quantitative Reverse Transcription PCR.

After treatment, cells were harvested and washed with cold PBS twice. Total RNA was extracted by GeneJET RNA Purification Kit (Thermo Scientific, Waltham, Mass., USA, catalog no. K0731) following manufacture protocol. The concentration of RNA was measured by Plate Reader. Total RNA at normalized concentration was subjected to reverse transcription to generate cDNA library by High-Capacity cDNA Reverse Transcription Kit (Applied Biosystems, Foster City, Calif., USA). 10 ng cDNA was mixed with primer sets and PowerUP SYBR Green Master Mix (Applied Biosystems) in 96-well optical PCR plate. Real-time PCR and fluorescent signal were processed using QuantStudio 7 Flex Real-Time PCR System (Life Technologies Corporation, Carlsbad, Calif., USA). Fast-cycling mode (50° C., 2 minutes, hold; 95° C., 2 minutes, hold; 95° C., 1 second, then, 60° C., 30 seconds, 40 cycles) was performed and followed with melt curve stage (1.6° C./second to 95° C., 15 seconds; 1.6° C./second to 60° C., 1 minute; 0.15° C./second to 95° C., 15 seconds). $C_t$ value at automatically selected threshold was reported and calculated by $2^{-\Delta\Delta C_t}$ method. (Livak, K. J.; Schmittgen, T. D. "Analysis of Relative Gene Expression Data Using Real-Time Quantitative PCR and the 2 C T Method" METHODS 2001, 25, 402-408. The bar graph was generated and by GraphPad Prism.

Statistical Analysis.

All statistical analysis was done using GraphPad Prism software. Statistical significance was analyzed by performing one-way or two-way ANOVA analysis of variance. Multiple group comparisons with vehicle or compound-treated group were followed Dunnett correction. Not significant (ns) P>0.05, *P≤0.05, P≤0.01, P≤0.001, **P≤0.0001.

Part 2:

An additional HDAC6 degrader 1 (see below) was made by tethering a HDAC inhibitor and pomalidomide to recruit cereblon (CRBN) E3 ligase. Although the non-selective inhibitor 1 can bind to all 11 isoforms of HDACs, the resulting degrader selectively induced the degradation of HDAC6. Based on this, a next-generation family of HDAC6 degraders was made using Nexturstat A (Next-A) as the ligand of protein of interest. Nexturstat A is 4-[[butyl[(phenylamino)carbonyl]amino]methyl]-N-hydroxy-benzamide, CAS Number 1403783-31-2:

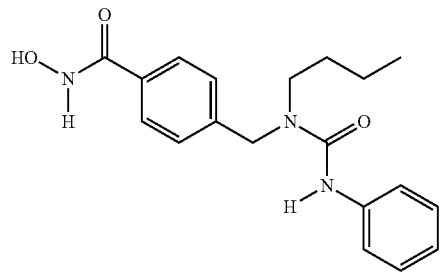 [SMILES: CCCCN(Cc1ccc(C(=O)NO)cc1)C(=O)Nc1ccccc1]

It is available commercially from several sources, including Cayman Chemical Company, Ann Arbor, Mich., USA.) Among the compounds prepared, compound 2 (below) showed the highest potency for the degradation of HDAC6. It also possessed promising anti-myeloma activity due to synergistic effects of HDAC6 degradation/inhibition and the degradation of IKZF1/3. The IKZFs are not physiologically relevant substrates of CRBN; but the binding of IMiDs such as pomalidomide to CRBN can induce the degradation of IKZFs—so called new-substrates. However, the degradation of IKZFs is not always desired and the pomalidomide moiety has several other potential substrates in addition to IKZFs. The putative number of E3 ligases in the human genome is over 600. However, only inhibitor of apoptosis protein (IAP), Von Hippel-Lindau tumor suppressor protein (VHL) and CRBN together with their ligands are widely exploited for the development of PROTACs for the degradation of various protein targets. VHL is part of the VBC E3 ubiquitin complex.

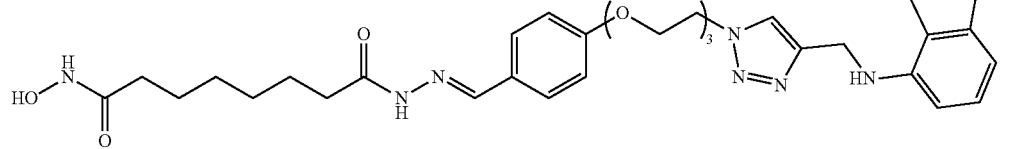

1

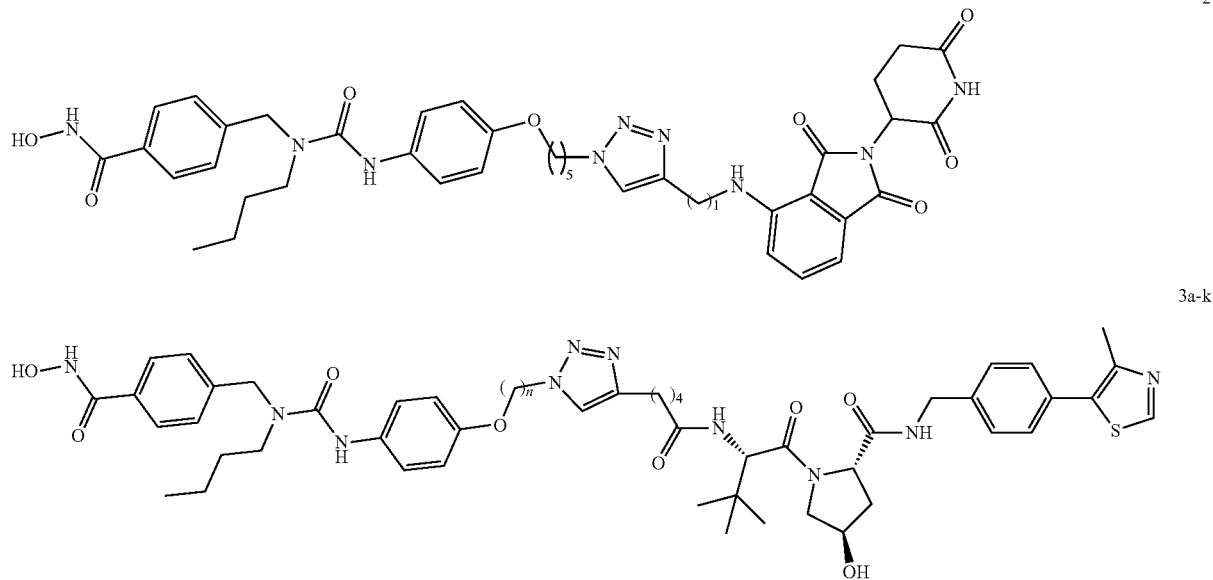

3a: n = 2; 3b: n = 3; 3c: n = 4; 3d: n = 5; 3e: n = 6; 3f: n = 7; 3g: n = 8; n = 9; 3i: n = 0; 3j: n = 11; 3k: n = 12.

Figure 15:
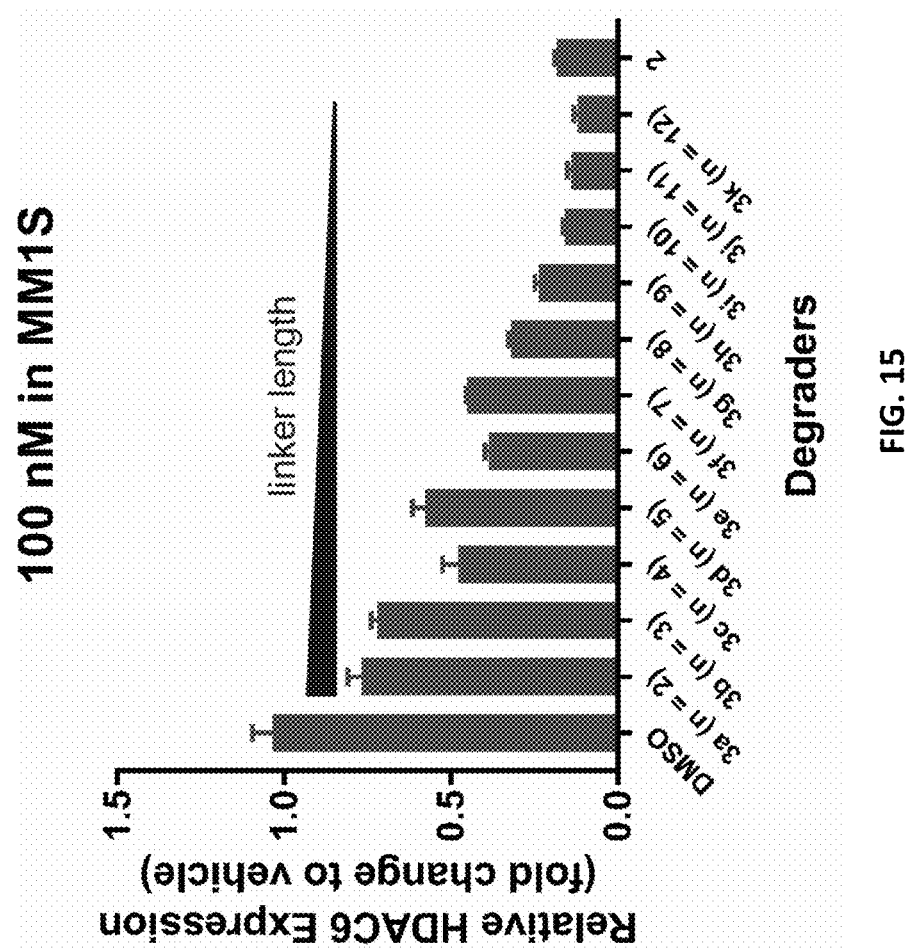
FIG. 15 is a histogram depicting relative HDAC6 expression as a function of linker length for compounds 3a through 3k as described in the Examples section, Part 2. Human MM1S cells were treated with 100 nM degraders for 6 hours and analyzed by in-cell ELISA assay.
Figure 16:
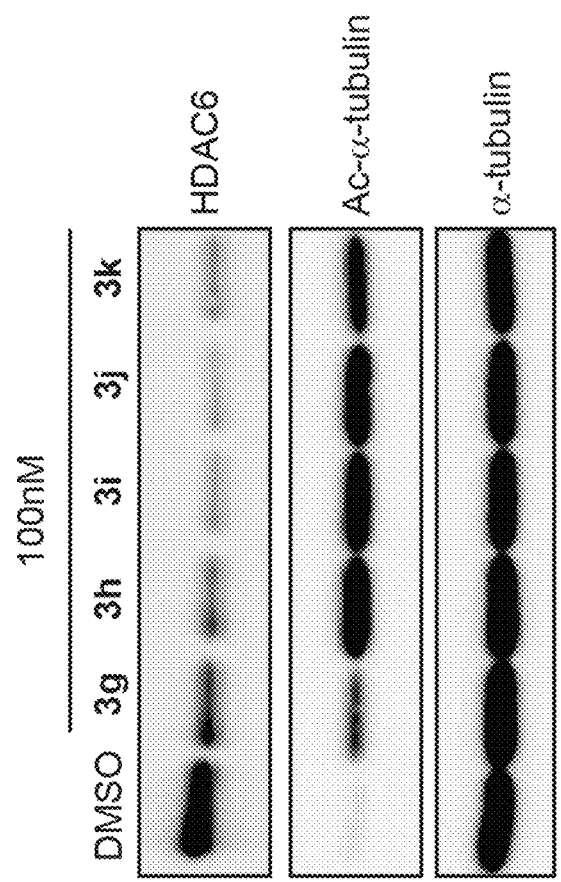
FIG. 16 is a western blot of selected candidate compounds having longer linkers. MM1S cells were treated with 100 nM degraders for 6 hours and analyzed by western blot.

To examine the feasibility of recruiting VHL E3 ligase to degrade HDAC6, several series of compounds were made with different linkers between Next-A and VHL ligand VHL-1.39 Among them, the eleven compounds 3a-k showed promising activity. See FIGS. 15 and 16. FIG. 15 shows relative HDAC6 expression as a function of linker length for compounds 3a through 3k. Here, Human MM1S cells were treated with 100 nM degraders for 6 hours and analyzed by in-cell ELISA assay. FIG. 16 is a western blot of selected candidate compounds having longer linkers. MM1S cells were treated with 100 nM degraders for 6 hours and analyzed by western blot.

Within this series of compounds, the number methylene units (n) between Next-A and the triazole ring ranged from 2 to 12. There are four methylene units between the triazole and the VHL ligand. These compounds were designated the "n+4" series.

The activity of all eleven "n+4" VHL-based potential degraders to suppress HDAC6 expression was tested at 100 nM and compared to CRBN degrader 2 in MM1S cells. The resulting cells were analyzed for HDAC6 expression by in-cell ELISA (FIG. 15). A clear trend was observed of increased potency as the linker length increased from compound 3a (n=2) to compound 3k (n=12). The three most potent compounds, 3i, 3j and 3k, induced the similar level of degradation compared to degrader 2, indicating that this new class of degraders achieves efficient depletion of HDAC6. Western blot analysis was used to confirm the ELISA results (FIG. 16). Degraders 3 g through 3k downregulated HDAC6 in a linker-length-dependent manner at 100 nM. It was also observed that degraders 3h through 3j increased more acetylated tubulin than others.

Figure 17:
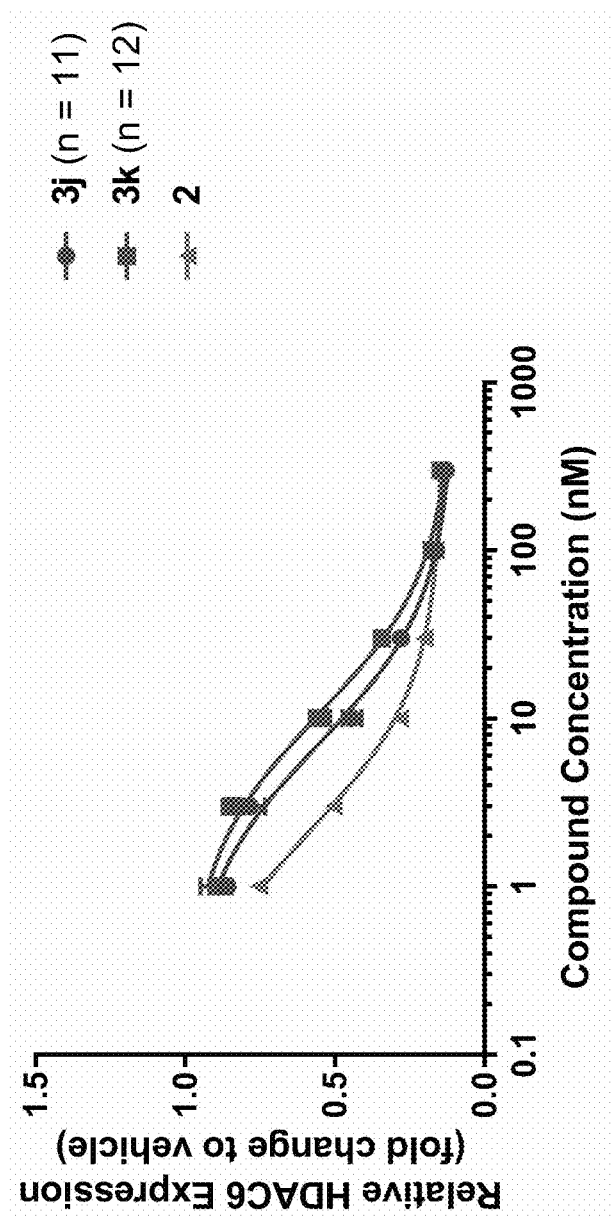
FIG. 17 is a dose-response curve for degraders 3j (n=1), 3k (n=12) and 2, at concentrations from 1 nM to 300 nM for 4 h in MM1S. See the Examples, Part 2.

To examine the efficiency of degraders further, a dose-response study of 3j, 3k and 2 was performed at concentrations ranging from 1 nM to 3 μM for 6 h in MM1S cells. The results are shown in FIG. 17. The $DC_{50}$ obtained for 2 was 2.2 nM. Degraders 3j and 3k were less potent in terms of $DC_{50}$. Both of them, however, showed larger $D_{max}$ (89.5%) than that of 2 (85.6%). It requires more degraders based on VHL-ligands to achieve similar degradation level of HDAC6 comparing to degraders derived from CRBN ligands. But degraders containing VHL-ligand depleted more HDAC6 than degraders derived from CRBN ligands at higher concentrations.

Degrader 3j was chosen for further studies based on its dose response, mechanism, and selectivity. MM1S cells were treated with this degrader at concentrations ranging from 1 nM to 30 μM for 4 h and analyzed them by western blot (data not shown. HDAC6 was degraded remarkably at as low as 10 nM of the degrader and the maximal effect was reached around 100 nM, which was consistent with in-cell ELSIA results. PROTACs often become less effective at higher concentrations because the formation of more two-binary complexes (E3-PROTAC and Protein of Interest-PROTAC) than that of ternary complex (E3-PROTAC-Protein of Interest). This phenomenon is often referred to as the "hook effect." See Douglass et al. (supra). "Hook effects" for HDAC6 degrader 3j was observed at 3 μM or higher concentrations. The acetylation level of tubulin was dose-dependent and reached the maximal effect around 1 μM of concentration. The effect on the expression other HDACs was minimal. In addition, obvious degradation of IKZFs was not seen, which was often degraded when thalidomide analogues were used as the E3 ubiquitin ligase recruiting ligands (data not shown).

When HDAC6 selective degraders 3j and 2 and HDAC6 selective inhibitor Next-A were compared with pan-HDAC inhibitor SAHA at different concentrations, selective increase of acetylated tubulin over acetylated histone was confirmed for HDAC6 selective degraders. LC-MS/MS based proteomic profiling allowed us to examine the global protein expression change of MM1S cells under treatment of 3j. Protein was down-regulated with statistical significance (log 2(3j/vehicle)<−2) and confidence (−log[P]>1) was not observed among over 1000 proteins. The unchanged expression level of HDAC1 and HDAC2 is consistent with western blot results (data not shown). The results collectively show that degrader 3j is a selective chemical probe for the degradation of HDAC6.

To probe further the efficiency of degrading HDAC6, a time-course study was performed. Both 3j and 2 started to reduce HDAC6 expression at 30 minutes and reached maximal degradation around 4 h. Both 3j and 2 also induced the increase of tubulin acetylation as expected; but the latter was slightly more potent. All of the data indicate that degrader 3j, based on a VHL ligand, effectively degrades HDAC6 selectively in cellular assays. See FIG. 17 for the dose-response curve for 3j, 3k, and 2.

To gain more evidence that the VHL-based degraders suppress HDAC6 expression via the ubiquitination-proteasome pathway, a series of experiments was conducted by co-treating the HDAC6 degraders with competitive pathway inhibitors. MM1S cells pre-treated with proteasome inhibitor (MG132 and Bortezomib) showed no obvious HDAC6 degradation by 3j, showing that the proteolysis of HDAC6 occurred in the proteasome. Next-A abolished the effect of HDAC6 degradation by 3j by competitively binding to HDAC6. NAE inhibitor MLN 4924 can deactivate the E3 ligase activity and abolish the 3j-induced degradation. It also indicated that neddylation and E3 were required for VHL-based PROTACs. VHL-1 completely recovered the HDAC6 expression at 5 μM or above (data not shown), demonstrating that VHL E3 was required for efficient degradation by the VHL-ligand based degraders.

Figure 18:
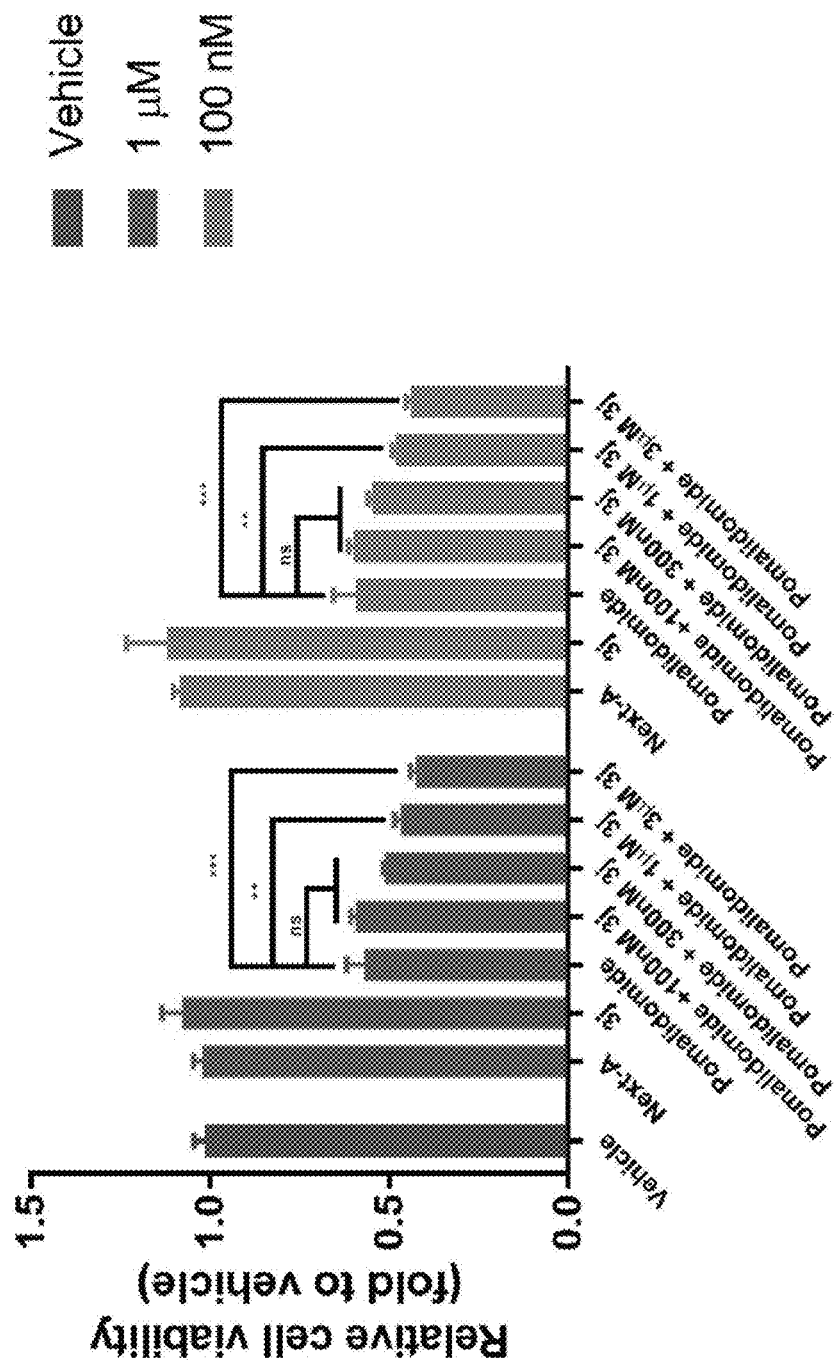
FIG. 18 is a histogram showing that HDAC6 degrader and IMiD inhibited MM1S growth synergistically. MM1S cells were treated for 72 h and cell proliferation was examined by AlarmaBlue-brand cell viability assay (ThermoFisher Scientific, Waltham, Mass., USA). Statistical significance was analyzed by one-way ANOVA. Not significant (ns) P>0.05, *P≤0.05, P≤0.01, *P≤0.001, ****P≤0.000

Degrader 2 alone has significant anti-proliferation effect by degrading both HDAC6 and IKZFs. Degrader 2 also showed higher anti-proliferation potency over pomalidomide alone, which is consistent with the synergistic effect observed for HDAC6 inhibitors and IMiDs. The single treatment of HDAC6 inhibitor, HDAC6 degrader 3j, IMiD (pomalidomide), and the combination of the two was compared in MM1S cells to evaluate cell viaility. The results are shown in FIG. 18. At 1 μM concentration, 3j or Next-A alone did not show any anti-proliferation effect for multiple myeloma. Pomalidomide suppressed ~50% proliferation at either 1 μM or 100 nM concentration. In the presence of pomalidomide, adding 1 μM or 3 μM of 3j further enhanced the anti-myeloma activity. The results confirmed that HDAC6 degradation and IKZF degradation work synergistically to inhibit the growth of multiple myeloma cells.

To explore the generality of 3j for the degradation of HDAC6, its effect on HDAC6 in other human cell lines including HEK293T, U87MG, A549, and MCF-7 was tested. Across all cell lines, HDAC6 was depleted in a dose-dependent manner, though the potency varies in these cell lines, which may be due to either the different expression levels of VHL E3 ligase or different re-synthesis rates of HDAC6 in these cell lines. (Data not shown).

Figure 19:
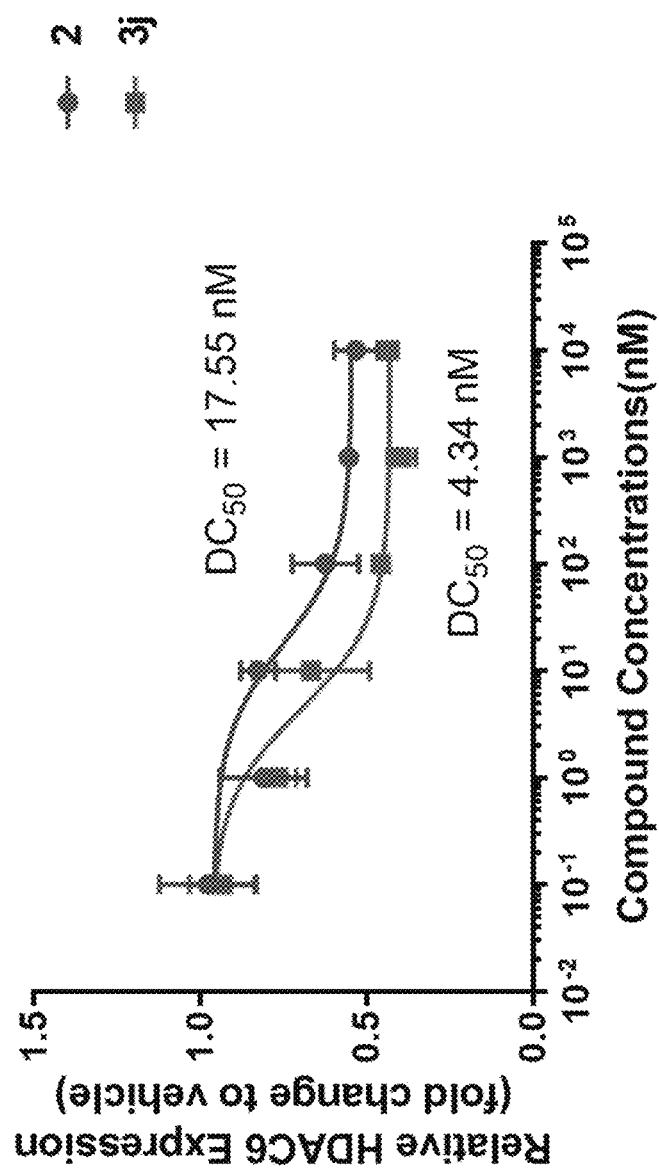
FIG. 19 is a dose-response curve for HDAC6 expression as a function of concentration for compounds 2 and 3j from Part 2 of the Example section.

The degradation efficiency of HDAC6 induced by 2 and 3j in mice immortalized cell line 4935 was also tested using western blot and in-cell ELISA. In concentrations ranging from 10 nM to 10 μM, VHL-based degrader 3j induced more HDAC6 degradation and tubulin acetylation than CRBN-based degrader 2 (data not shown). ELISA results also showed that 3j was more potent than 2 and their calculated $DC_{50}$'s were about 4 nM and 17 nM, respectively. See FIG. 19. The maximal degradation percentage for HDAC6 induced by 3j is 56.8%, which is better than 45.3% of $D_{max}$ induced by compound 2. The data indicated that the relative potency of different PROTACs may vary among different species. The VHL E3 ligase-based degrader 3j may have advantages over CRBN-based degrader 2 in animal studies using mice as the model system.

Disclosed herein is a new class of HDAC6 degraders that studies indicate function by recruiting VHL instead of CRBN as the E3 ubiquitin ligase. The linker length required for optimal VHL-ligand based degraders is generally longer than that of CRBN-ligand based degraders. Compound 3j was identified as the most potent candidate among this class of HDAC6 degraders. It is slightly less efficient for the degradation of HDAC6 at low concentrations than that of 2. But 3j had higher maximal degradation at high concentrations than 2. Mechanistic studies demonstrated that 3j targeted HDAC6 for proteasomal degradation. Compound 3j didn't induce the degradation of IKZF1/3, which were often the targets of previous CRBN-ligand based de-graders. The VHL-based degrader 3j is also less sensitive to the species difference than the CRBN-based degrader 2. The potency, selectivity, and reduced species dependence underscore the utility of 3j as a specific chemical probe for the degradation of HDAC6 to study HDAC6-related biological pathways.

What is claimed is:

1. A compound comprising a histone deacetylase 6 ("HDAC6")-selective inhibitor covalently bonded to a linker, covalently bonded to an E3 ubiquitin ligase ligand:

wherein:
the HDAC6-selective inhibitor is selected from the group consisting of:

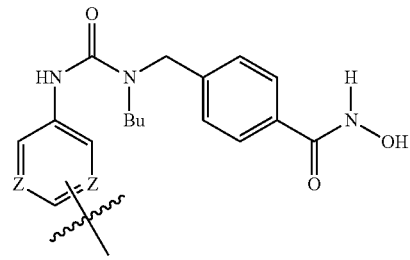

wherein each Z is independently selected from —N— or —(CH)—;
the linker is a $C_1$-$C_{12}$ linear or branched alkylene, alkenylene, or alkynylene, —O—$(CH_2)_m$—, or —NH—$(CH_2)_m$, wherein "m" is an integer of from 1 to 12; and
the E3 ubiquitin ligase ligand is selected from:

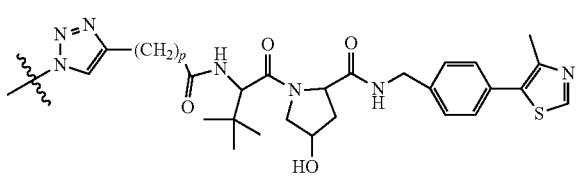

wherein "p" is an integer of from 1 to 12; and
salts thereof.

2. The compound of claim 1, wherein the linker is $C_1$-$C_{12}$ linear or branched alkylene, alkenylene, or alkynylene.

3. The compound of claim 2, wherein each Z is —N—.

4. The compound of claim 2, wherein each Z is —(CH)—.

5. The compound of claim 1, wherein the linker is —O—$(CH_2)_m$—.

6. The compound of claim 5, wherein each Z is —N—.

7. The compound of claim 5, wherein each Z is —(CH)—.

8. The compound of claim 1, wherein the linker is —NH—$(CH_2)_m$.

9. The compound of claim 8, wherein each Z is —N—.

10. The compound of claim 8, wherein each Z is —(CH)—.

11. The compound of claim 1, wherein the HDAC6-selective inhibitor is:
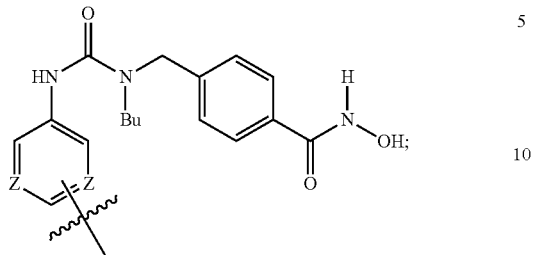
the linker is —O—(CH$_2$)$_m$—; and
the E3 ubiquitin ligase ligand is:
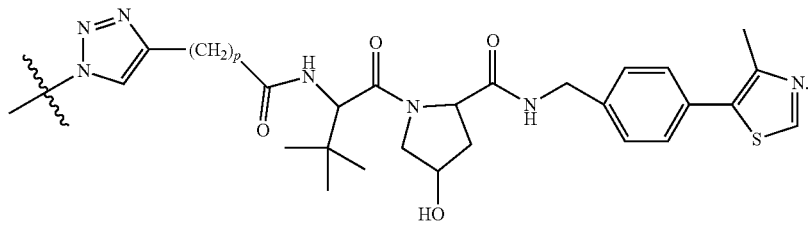
12. The compound of claim 11, wherein each Z is —N—.
13. The compound of claim 11, wherein each Z is —(CH)—.
14. The compound of claim 11, wherein "p" is 3, 4, or 5.
* * * * *